(12) United States Patent
Yamaguchi et al.

(10) Patent No.: US 8,460,851 B2
(45) Date of Patent: *Jun. 11, 2013

(54) SALT AND PHOTORESIST COMPOSITION CONTAINING THE SAME

(75) Inventors: Satoshi Yamaguchi, Kawachinagano (JP); Koji Ichikawa, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 177 days.

This patent is subject to a terminal disclaimer.

(21) Appl. No.: 12/985,838

(22) Filed: Jan. 6, 2011

(65) Prior Publication Data

US 2011/0171576 A1 Jul. 14, 2011

(30) Foreign Application Priority Data

Jan. 14, 2010 (JP) .................................. 2010-006121
May 27, 2010 (JP) .................................. 2010-121137

(51) Int. Cl.
*G03F 7/004* (2006.01)
*G03F 7/039* (2006.01)
*G03F 7/20* (2006.01)
*G03F 7/30* (2006.01)
*G03F 7/38* (2006.01)

(52) U.S. Cl.
USPC ........ 430/270.1; 430/311; 430/325; 430/326; 430/330; 430/910; 430/920; 430/921; 430/925; 544/158; 544/170; 544/178; 546/248; 546/346; 546/348; 548/215; 548/573; 548/574; 548/950; 548/968

(58) Field of Classification Search
None
See application file for complete search history.

(56) References Cited

U.S. PATENT DOCUMENTS

| | | | |
|---|---|---|---|
| 6,200,728 B1 | 3/2001 | Cameron et al. | |
| 6,203,965 B1 | 3/2001 | Cameron et al. | |
| 6,803,169 B2 | 10/2004 | Cameron et al. | |
| 8,236,842 B2 * | 8/2012 | Yoshida et al. | ................ 514/397 |
| 2002/0102491 A1 | 8/2002 | Kodama et al. | |
| 2006/0194982 A1 | 8/2006 | Harada et al. | |
| 2010/0081088 A1 * | 4/2010 | Kawaue et al. | ............ 430/285.1 |

FOREIGN PATENT DOCUMENTS

JP 7-333851 A 12/1995

* cited by examiner

*Primary Examiner* — Sin J. Lee
(74) *Attorney, Agent, or Firm* — Birch, Stewart, Kolasch & Birch, LLP

(57) ABSTRACT

A salt represented by the formula (I):

$$Z^{1\oplus} \quad {}^{\ominus}O_3S \underset{Q^2}{\overset{Q^1}{\underset{|}{\overset{|}{C}}}} L^1 \underset{}{\overset{}{N}} W^1 \qquad (I)$$

wherein $Q^1$ and $Q^2$ each independently represent a fluorine atom or a C1-C6 perfluoroalkyl group, $L^1$ represents *—CO—O—$L^a$- or *—CH$_2$—O—$L^b$-, * represents a binding position to —C($Q^1$)($Q^2$)-, $L^a$ and $L^b$ independently represent a C1-C15 divalent saturated hydrocarbon group in which one or more —CH$_2$— can be replaced by —O— or —CO—, ring $W^1$ represents a C2-C36 nitrogen-containing heterocyclic group in which one or more —CH$_2$— can be replaced by —O—, and $Z^{1\oplus}$ represents an organic counter ion.

8 Claims, No Drawings

SALT AND PHOTORESIST COMPOSITION CONTAINING THE SAME

This nonprovisional application claims priority under 35 U.S.C. §119(a) on Patent Application No. 2010-006121 filed in JAPAN on Jan. 14, 2010 and on Patent Application No. 2010-121137 filed in JAPAN on May 27, 2010, the entire contents of which are hereby incorporated by reference.

FIELD OF THE INVENTION

The present invention relates to a salt and a photoresist composition containing the same.

BACKGROUND OF THE INVENTION

A chemically amplified positive photoresist composition used for semiconductor microfabrication employing a lithography process contains an acid generator comprising a compound generating an acid by irradiation.

US 2002/0102491 A1 discloses a salt represented by the following formula:

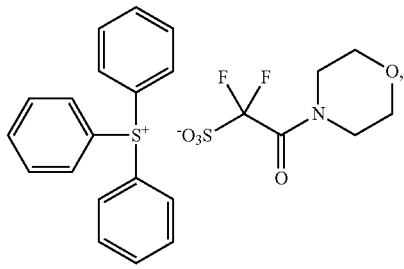

and a photoresist composition containing the same as an acid generator.

SUMMARY OF THE INVENTION

An object of the present invention is to provide a novel salt and a photoresist composition containing the same.

The present invention relates to the followings:

<1> A salt represented by the formula (I):

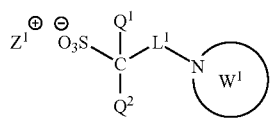

wherein $Q^1$ and $Q^2$ each independently represent a fluorine atom or a C1-C6 perfluoroalkyl group, $L^1$ represents *—CO—O-$L^a$- or *—CH$_2$—O-$L^b$-, * represents a binding position to —C($Q^1$)($Q^2$)-, $L^a$ and $L^b$ independently represent a C1-C15 divalent saturated hydrocarbon group in which one or more —CH$_2$— can be replaced by —O— or —CO—, ring $W^1$ represents a C2-C36 nitrogen-containing heterocyclic group in which one or more —CH$_2$— can be replaced by —O—, and $Z^{1\oplus}$ represents an organic counter ion;

<2> The salt according to <1>, wherein $L^1$ represents *—CO—O-$L^a$-;

<3> The salt according to <1> or <2>, wherein $Z^{1\oplus}$ is a triarylsulfonium cation;

<4> An acid generator comprising the salt according to <1>, <2> or <3>;

<5> A photoresist composition comprising the acid generator according to <4> and a resin;

<6> The photoresist composition according to <5>, wherein the resin comprises a structural unit having an acid-labile group, being insoluble or poorly soluble in an aqueous alkali solution but becoming soluble in an aqueous alkali solution by the action of an acid;

<7> The photoresist composition according to <5> or <6>, which further contains a basic compound;

<8> A process for producing a photoresist pattern comprising the following steps (1) to (5):

(1) a step of applying the photoresist composition according to <5>, <6> or <7> on a substrate,
(2) a step of forming a photoresist film by conducting drying,
(3) a step of exposing the photoresist film to radiation,
(4) a step of baking the exposed photoresist film, and
(5) a step of developing the baked photoresist film with an alkaline developer, thereby forming a photoresist pattern.

DESCRIPTION OF PREFERRED EMBODIMENTS

The salt of the present invention is represented by the formula (I):

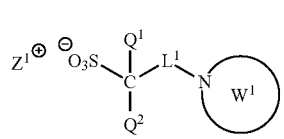

wherein $Q^1$ and $Q^2$ each independently represent a fluorine atom or a C1-C6 perfluoroalkyl group, $L^1$ represents *—CO—O-$L^a$- or *—CH$_2$—O-$L^b$-, * represents a binding position to —C($Q^1$)($Q^2$)-, $L^a$ and $L^b$ independently represent a C1-C15 divalent saturated hydrocarbon group in which one or more —CH$_2$— can be replaced by —O— or —CO—, ring $W^1$ represents a C2-C36 nitrogen-containing heterocyclic group in which one or more —CH$_2$— can be replaced by —O—, and $Z^{1\oplus}$ represents an organic counter ion (hereinafter, simply referred to as SALT (I)).

Examples of the C1-C6 perfluoroalkyl group include a trifluoromethyl group, a pentafluoroethyl group, a heptafluoropropyl group, a nonafluorobutyl group, an undecafluoropentyl group and a tridecafluorohexyl group, and a trifluoromethyl group is preferable. $Q^1$ and $Q^2$ each independently preferably represent a fluorine atom or a trifluoromethyl group, and $Q^1$ and $Q^2$ are more preferably fluorine atoms.

$L^1$ is preferably *—CO—O-$L^a$-.

Examples of the C1-C15 divalent saturated hydrocarbon group include a C1-C17 linear alkylene group such as a methylene group, an ethylene group, a propane-1,3-diyl group, a propane-1,2-diyl group, a butane-1,4-diyl group, a butane-1,3-diyl group, a pentane-1,5-diyl group, a hexane-1,6-diyl group, a heptane-1,7-diyl group, an octane-1,8-diyl group, a nonane-1,9-diyl group, a decane-1,10-diyl group, a undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group and a heptadecane-1,17-diyl group; a C2-C17 branched alkylene group such as a 1-methyl-1,3-propylene group, a 2-methyl-1,3-propylene group, a 2-methyl-1,2-propylene group, a 1-methyl-1,4-butylene group, and a 2-methyl-1,4-butylene group; a divalent monocyclic saturated hydrocarbon group such as a cyclobutane-1,3-diyl group, a cyclopentane-1,3-diyl group, a cyclohexane-1,2-diyl group, a 1-methylcyclohexane-1,2-diyl group, a cyclohexane-1,4-diyl group, a cyclooctane-1,2-diyl group and a cyclooctane-1,5-diyl group; a divalent polycyclic saturated hydrocarbon group such as a norbornane-2,3-diyl group, a norbornane-1,4-diyl group, a norbornane-2,5-diyl group, an adamantane-1,2-diyl group, an adamantane-1,5-diyl group and an adamantane-2,6-diyl group; and a group formed by combining two or more groups selected from the group consisting of the above-mentioned groups.

Examples of *—CO—O-$L^a$- in which one or more —$CH_2$— are replaced by —O— or —CO— include *—CO—O-$L^c$-CO—O-$L^d$- in which $L^c$ and $L^d$ independently represent a C1-C12 saturated hydrocarbon group, with the proviso that total carbon number of $L^c$ and $L^d$ is 1 to 13.

Examples of *—$CH_2$—O-$L^b$- in which one or more —$CH_2$— are replaced by —O— or —CO— include *—$CH_2$—O—CO-$L^e$- in which $L^e$ represents a C1-C14 saturated hydrocarbon group.

Examples of *—CO—O-$L^a$-include *—CO—O—$CH_2$—, *—CO—O—$CH_2$—$CH_2$—, *—CO—O—$(CH_2)_3$—$CH_2$—, *—CO—O—$(CH_2)_5$—$CH_2$—, *—CO—O—$(CH_2)_7$—$CH_2$—, *—CO—O—$(CH_2)_9$—$CH_2$—, *—CO—O—$(CH_2)_{11}$—$CH_2$, *—CO—O—$CH_2$—CO—O—$CH_2$, *—CO—O—$(CH_2)_2$—CO—O—$CH_2$—, *—CO—O— $(CH_2)_3$—CO—O—$CH_2$—, *—CO—O—$(CH_2)_4$—CO—O—$CH_2$—*—CO—O— $(CH_2)_6$—CO—O—$CH_2$—, *—CO—O—$(CH_2)_8$—CO—O—$CH_2$—, *—CO—O—$CH_2$—CO—O—$(CH_2)_2$—, *—CO—O—$CH_2$—CO—O— $(CH_2)_4$—, *—CO—O—$CH_2$—CO—O—$(CH_2)_6$—, *—CO—O— $CH_2$—CO—O— $(CH_2)_8$—, *—CO—O—$CH_2$—CO—O—$(CH_2)_{12}$—, *—CO—O—$CH_2$—CH($CH_3$)—CO—O—$(CH_2)_8$—, *—CO—O—$CH_2$—C($CH_3$)$_2$—CO—O—$(CH_2)_8$—, and the followings.

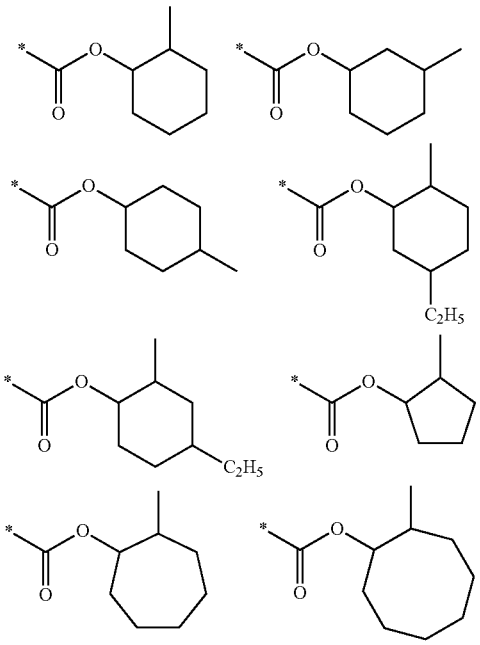

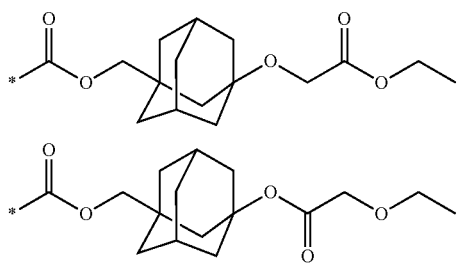

Examples of *—$CH_2$—O-$L^b$-include the followings.

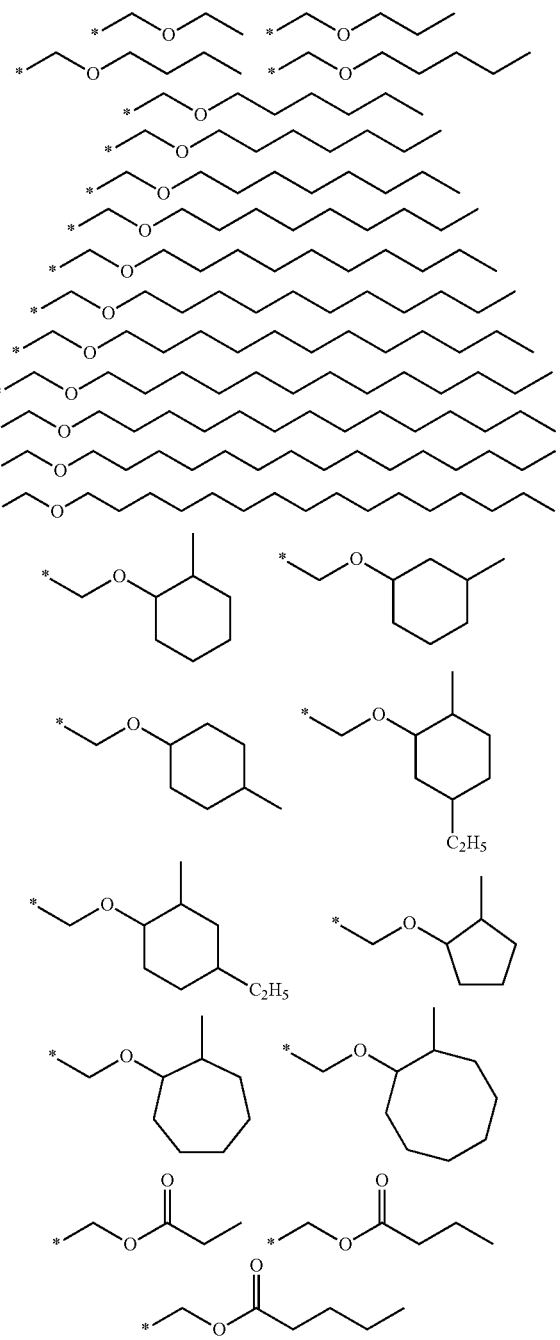

-continued

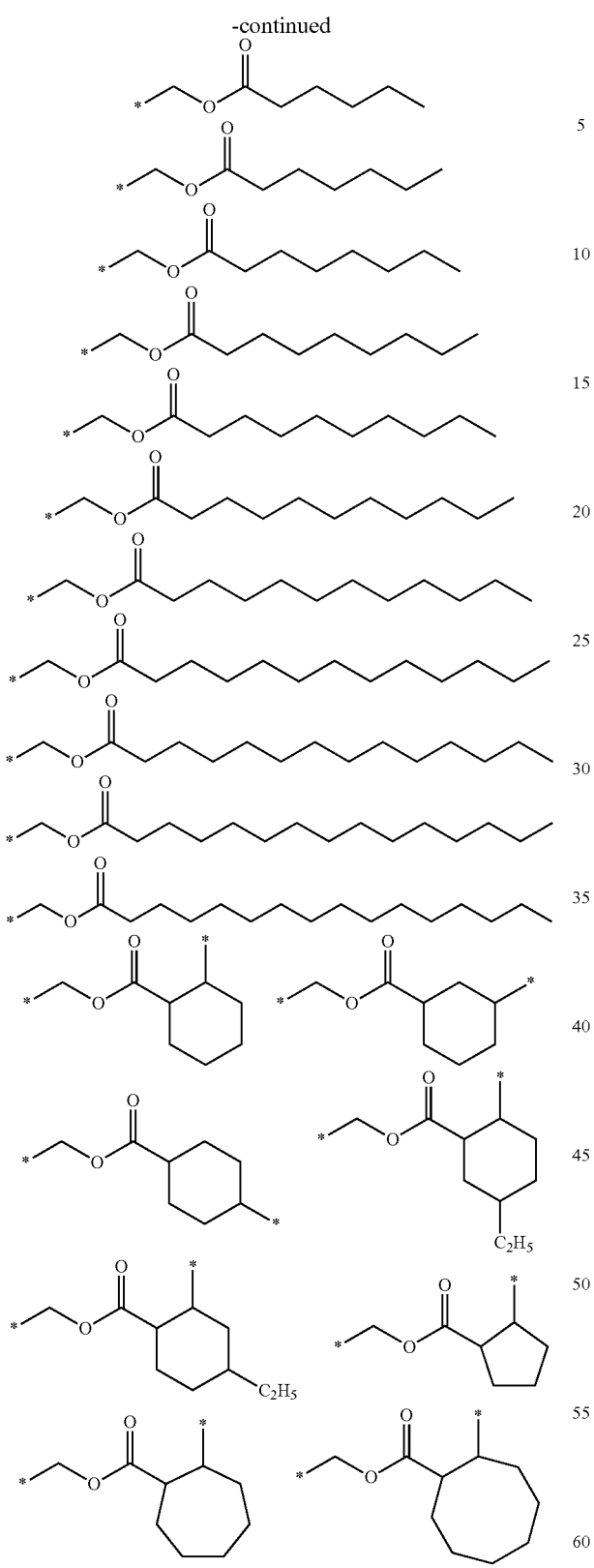

Ring W¹ represents a C2-C36 nitrogen-containing heterocyclic group and one or more —CH₂— in the heterocyclic group can be replaced by —O—. The heterocyclic group may be a heteroaromatic group, and may be a heterocyclic group having no aromaticity. The heterocyclic group may be a monocyclic and may be a polycyclic. The heterocyclic group is preferably a heterocyclic group having no aromaticity.

Examples of the group represented by the formula:

include the following groups, and preferred are the groups represented by the formulae (W1), (W2) and (W3).

(W1)
(W2)
(W3)
(W4)
(W5)
(W6)
(W7)
(W8)

Examples of SALT (I) include the followings.

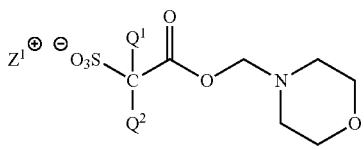

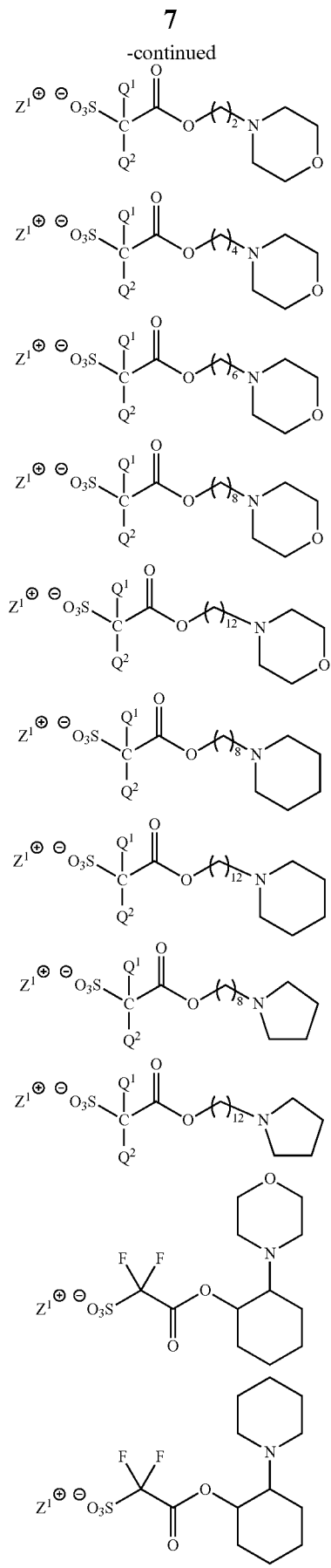
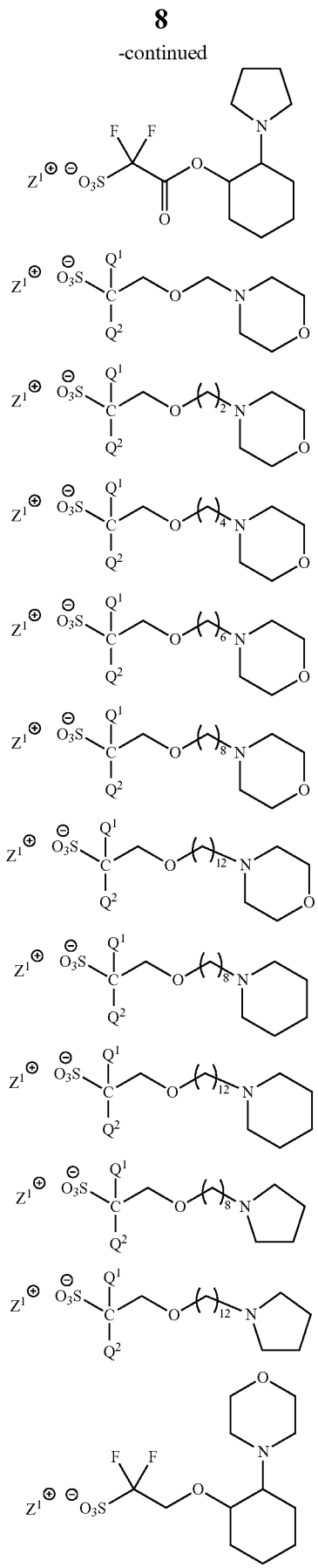

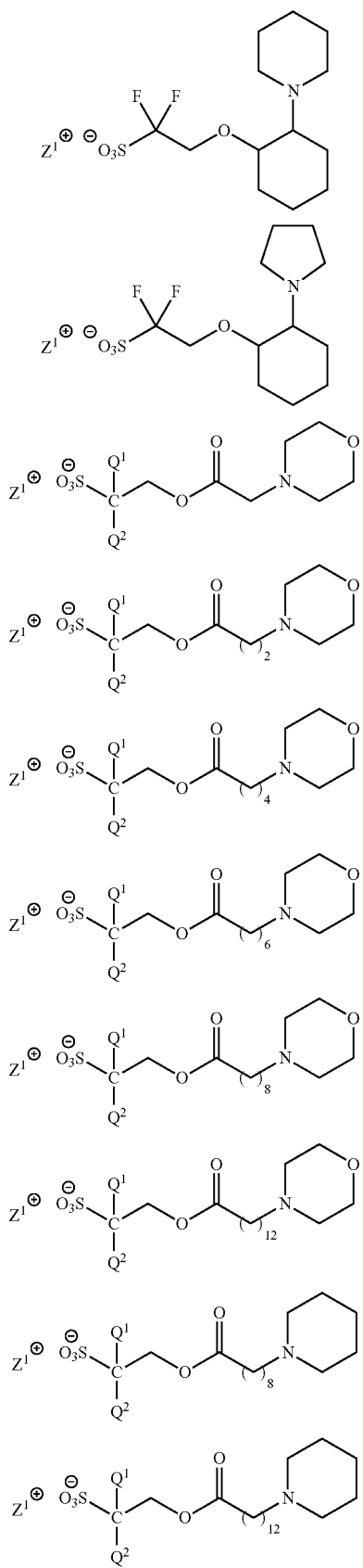

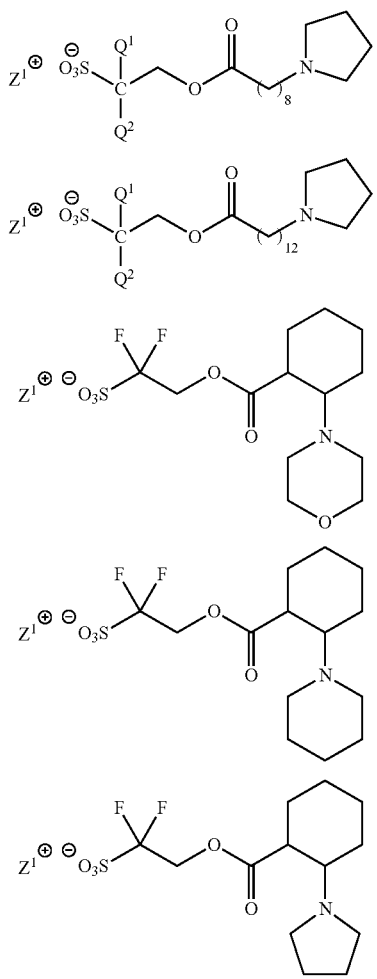

Examples of the counter ion represented by $Z^{1\oplus}$ include an onium cation such as a sulfonium cation, an iodonium cation, an ammonium cation, a benzothiazolium cation and a phosphonium cation, and a sulfonium cation and an iodonium cation are preferable, and an arylsulfonium cation is more preferable, and triarylsulfonium cation is especially preferable.

Preferable examples of the cation part represented by $Z^{1\oplus}$ include the cations represented by the formulae (Z1) to (Z4):

(Z1)

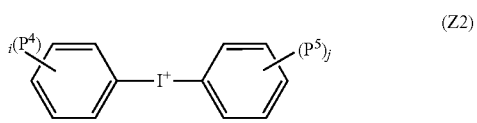
(Z2)

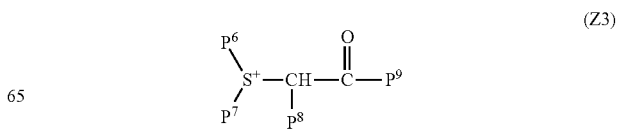
(Z3)

-continued

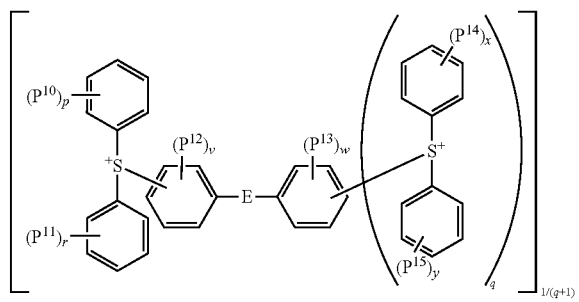

(Z4)

wherein $P^a$, $P^b$ and $P^c$ independently represent a C1-C30 aliphatic hydrocarbon group which can have one or more substituents selected from the group consisting of a hydroxyl group, a C1-C12 alkoxy group and a C6-C18 aromatic hydrocarbon group, a C3-C36 saturated cyclic hydrocarbon group which can have one or more substituents selected from the group consisting of a halogen atom, a C2-C4 acyl group and a glycidyloxy group, or a C6-C18 aromatic hydrocarbon group which can have one or more substituents selected from the group consisting of a halogen atom, a hydroxyl group, a C1-C36 aliphatic hydrocarbon group, a C3-C36 saturated cyclic hydrocarbon group or a C1-C12 alkoxy group, $P^4$ and $P^5$ are independently in each occurrence a hydroxyl group, a C1-C12 aliphatic hydrocarbon group or a C1-C12 alkoxy group, and j independently represents an integer of 0 to 5, $P^6$ and $P^7$ independently represent a C1-C36 aliphatic hydrocarbon group or a C3-C36 saturated cyclic hydrocarbon group, or $P^6$ and $P^7$ are bonded to form a C2-C11 divalent acyclic hydrocarbon group which forms a ring together with $S^+$, and one or more —CH$_2$— in the divalent acyclic hydrocarbon group may be replaced by —CO—, —O— or —S—, and $P^8$ represents a hydrogen atom, a 01-036 aliphatic hydrocarbon group, a C3-C36 saturated cyclic hydrocarbon group or a C6-C18 aromatic hydrocarbon group, $P^9$ represents a C1-C12 aliphatic hydrocarbon group, a C6-C18 saturated cyclic hydrocarbon group or a C6-C18 aromatic hydrocarbon group and the aromatic hydrocarbon group can have one or more substituents selected from the group consisting of a C1-C12 aliphatic hydrocarbon group, a C1-C12 alkoxy group, a C3-C18 saturated cyclic hydrocarbon group and an C2-C13 acyloxy group, or $P^8$ and $P^9$ are bonded each other to form a C1-C10 divalent acyclic hydrocarbon group which forms a 2-oxocycloalkyl group together with —CHCO— to which $P^8$ and $P^9$ are bonded, and one or more —CH$_2$— in the divalent acyclic hydrocarbon group may be replaced by —CO—, —O— or —S—, and $P^{10}$, $P^{11}$, $P^{12}$, $P^{13}$, $P^{14}$ and $P^{15}$ independently represents a hydroxyl group, a C1-C12 aliphatic hydrocarbon group or a C1-C12 alkoxy group, E represents —S— or —O— and p, r, x and y independently represents an integer of 0 to 5, v and w independently represents an integer of 0 to 4, and q represents 0 or 1.

The aliphatic hydrocarbon group represented by $P^a$ to $P^c$ has preferably 1 to 12 carbon atoms. The saturated cyclic hydrocarbon group represented by $P^a$ to $P^c$ has preferably 3 to 18 carbon atoms and more preferably 4 to 12 carbon atoms.

Examples of the aliphatic hydrocarbon group include an alkyl group such as a methyl group, an ethyl group, a propyl group, an isopropyl group, a butyl group, a sec-butyl group, a tert-butyl group, a 1-methylpropyl group, a 2,2-dimethylpropyl group, a 1-ethylpropyl group, a 1-methylbutyl group, a 2-methylbutyl group, a 3-methylbutyl group, a 1-propylbutyl group, a pentyl group, a 1-methylpentyl group, a hexyl group, a 1,4-dimethylhexyl group, a heptyl group, a 1-methylheptyl group, a 2-ethylhexyl group, an octyl group, a methyloctyl group, a nonyl group, a methylnonyl group, a decyl group, an undecyl group and a dodecyl group.

The saturated cyclic hydrocarbon group may be monocyclic or polycyclic, and examples of the monocyclic saturated hydrocarbon group include a cycloalkyl group such as a cyclopentyl group, a cyclohexyl group, a methylcyclohexyl group, a dimethylcyclohexyl group, a cycloheptyl group and a cyclooctyl group. Examples of the polycyclic saturated hydrocarbon group include a decahydronaphthyl group, an adamantyl group, a norbornyl group, a methylnorbornyl group and the followings.

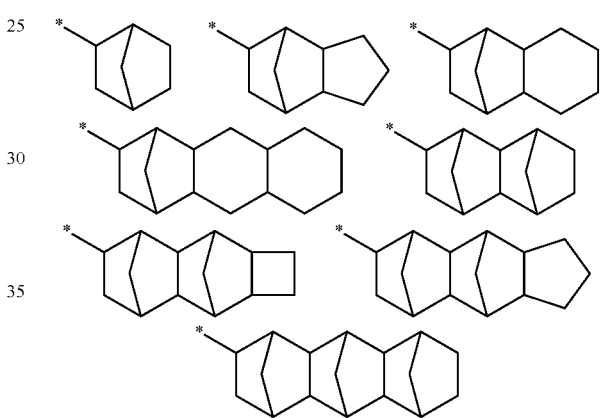

Examples of the aromatic hydrocarbon group include an aryl group such as a phenyl group, a naphthyl group, an anthryl group, a p-methylphenyl group, a p-tert-butylphenyl group, a p-adamantylphenyl group, a tolyl group, a xylyl group, a cumyl group, a mesityl group, a biphenyl group, a phenanthryl group, a 2,6-diethylphenyl group and a 2-methyl-6-ethylphenyl group.

Examples of the halogen atom include a fluorine atom, a bromine atom, a chlorine atom and an iodine atom. Examples of the C1-C12 alkyl group include a methyl group, an ethyl group, a propyl group, a butyl group, a pentyl group, a hexyl group, a heptyl group, an octyl group, a nonyl group, a decyl group, an undecyl group and a dodecyl group. Examples of the C1-C12 alkoxy group include a methoxy group, an ethoxy group, a propoxy group, a butoxy group, a pentyloxy group, a hexyloxy group, a heptyloxy group, an octyloxy group, a nonyloxy group, a decyloxy group, an undecyloxy group and a dodecyloxy group. Examples of the C2-C4 acyl group include an acetyl group, a propionyl group and a butyryl group. Examples of the C2-C13 acyloxy group include an acetyloxy group, a propionyloxy group, a butyryloxy group, an isopropylcarbonyloxy group, a sec-butylcarbonyloxy group, a tert-butylcarbonyloxy group, a pentylcarbonyloxy group, a hexylcarbonyloxy group, an octylcarboyloxy group and a 2-ethylhexylcarbonyloxy group. Examples of the C6-C12 aryl group include a phenyl group and a naphthyl group. Examples of the C7-C21 aralkyl group include a benzyl group, a phenethyl group, a phenylpropyl group, a trityl group, a naphthylmethyl group and a naphthylethyl group.

Preferable examples of the aliphatic hydrocarbon group include a methyl group, an ethyl group, a propyl group, an isopropyl group, a butyl group, a sec-butyl group, a tert-butyl group, a pentyl group, a hexyl group, an octyl group and a 2-ethylhexyl group. Preferable examples of the saturated cyclic hydrocarbon group include a cyclopropyl group, a cyclobutyl group, a cyclopentyl group, a cyclohexyl group, a cycloheptyl group, a cyclodecyl group, a 2-alkyl-2-adamantyl group, a 1-(1-adamantyl)-1-alkyl group and an isobornyl group. Preferable examples of the aromatic group include a phenyl group, a 4-methylphenyl group, a 4-ethylphenyl group, a 4-tert-butylphenyl group, a 4-cyclohexylphenyl group, a 4-methoxyphenyl group, a biphenyl group and a naphthyl group. Examples of the aliphatic hydrocarbon group having an aromatic hydrocarbon group include a benzyl group. Examples of the alkoxy group include a methoxy group, an ethoxy group, a propoxy group, an isopropoxy group, a butoxy group, a sec-butoxy group, a tert-butoxy group, a pentyloxy group, a hexyloxy group, a heptyloxy group, an octyloxy group, a 2-ethylhexyloxy group, a nonyloxy group, a decyloxy group, an undecyloxy group and a dodecyloxy group.

Examples of the C3-C12 divalent acyclic hydrocarbon group formed by bonding $P^6$ and $P^7$ include a trimethylene group, a tetramethylene group and a pentamethylene group. Examples of the ring group formed together with $S^+$ and the divalent acyclic hydrocarbon group include a thiolan-1-ium ring (tetrahydrothiphenium ring), a thian-1-ium ring and a 1,4-oxathian-4-ium ring. A C3-C7 divalent acyclic hydrocarbon group is preferable.

Examples of the C1-C10 divalent acyclic hydrocarbon group formed by bonding $P^8$ and $P^9$ include a methylene group, an ethylene group, a trimethylene group, a tetramethylene group and a pentamethylene group and examples of the ring group include the followings.

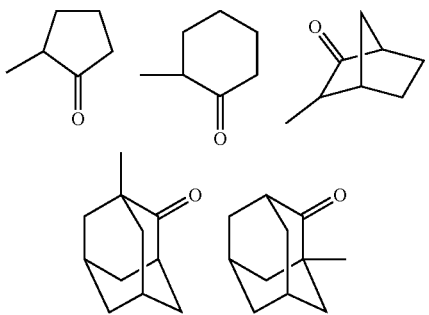

Among the above-mentioned cations, preferred is the cation represented by the formula (Z1), and more preferred is the cation represented by the formula (Z5), and especially preferred is a triphenylsulfonium cation.

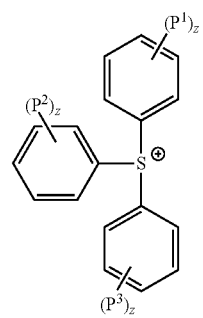

(Z5)

wherein $P^1$, $P^2$ and $P^3$ are independently in each occurrence a halogen atom, a hydroxyl group, a C10-C36 aliphatic hydrocarbon group, a C3-C36 saturated cyclic hydrocarbon group or a C1-C12 alkoxy group, and one or more hydrogen atoms in the aliphatic hydrocarbon group can be replaced by a hydroxyl group, a C1-C12 alkoxy group or a C6-C18 aromatic hydrocarbon group, one or more hydrogen atoms of the saturated cyclic hydrocarbon group can be replaced by a halogen atom, a C2-C4 acyl group or a glycidyloxy group, and z is independently in each occurrence an integer of 0 to 5. The aliphatic hydrocarbon group preferably has 1 to 12 carbon atoms, and the saturated cyclic hydrocarbon group preferably has 4 to 36 carbon atoms, and it is preferred that z is independently in each occurrence 0 or 1. It is preferred that $P^1$, $P^2$ and $P^3$ are independently halogen atom (preferably a fluorine atom), a hydroxyl group, a C1-C12 alkyl group or a C1-C12 alkoxy group.

Examples of the cation represented by the formula (Z1) include the followings.

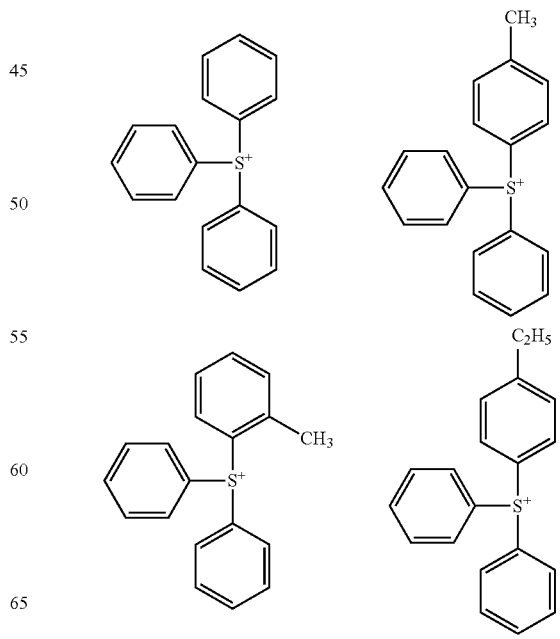

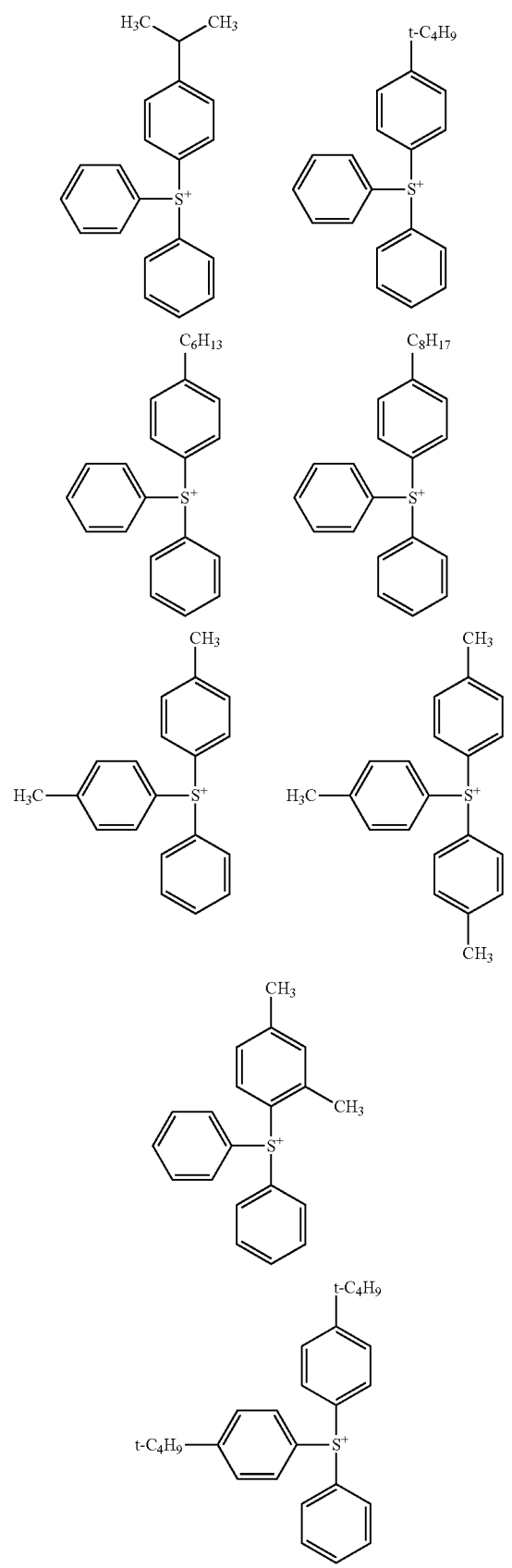

-continued
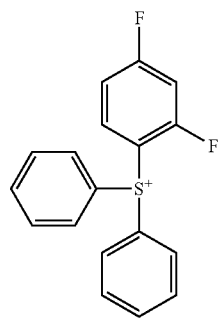
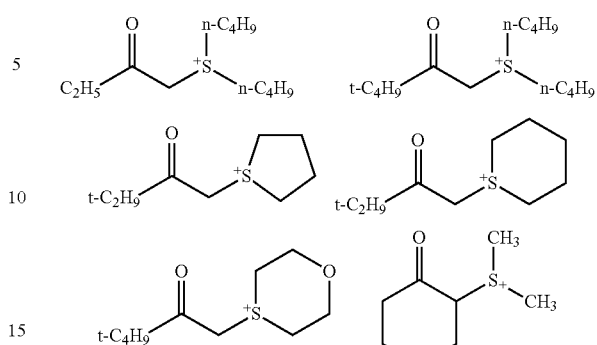
Examples of the cation represented by the formula (Z2) include the followings.
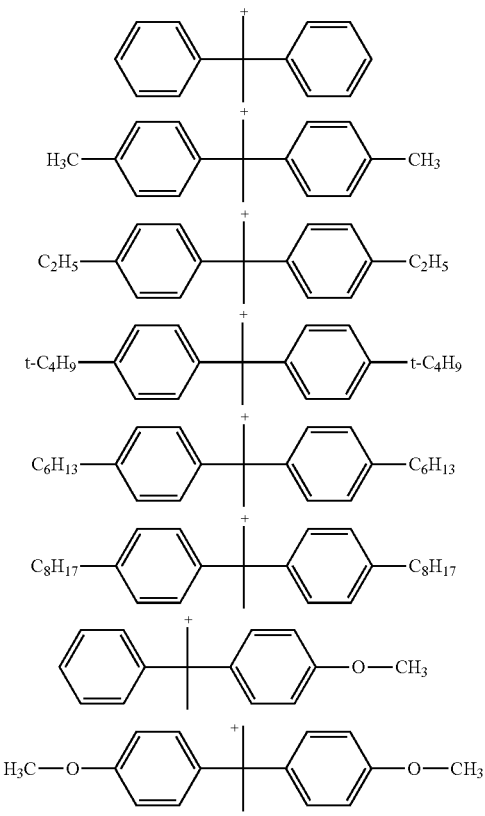
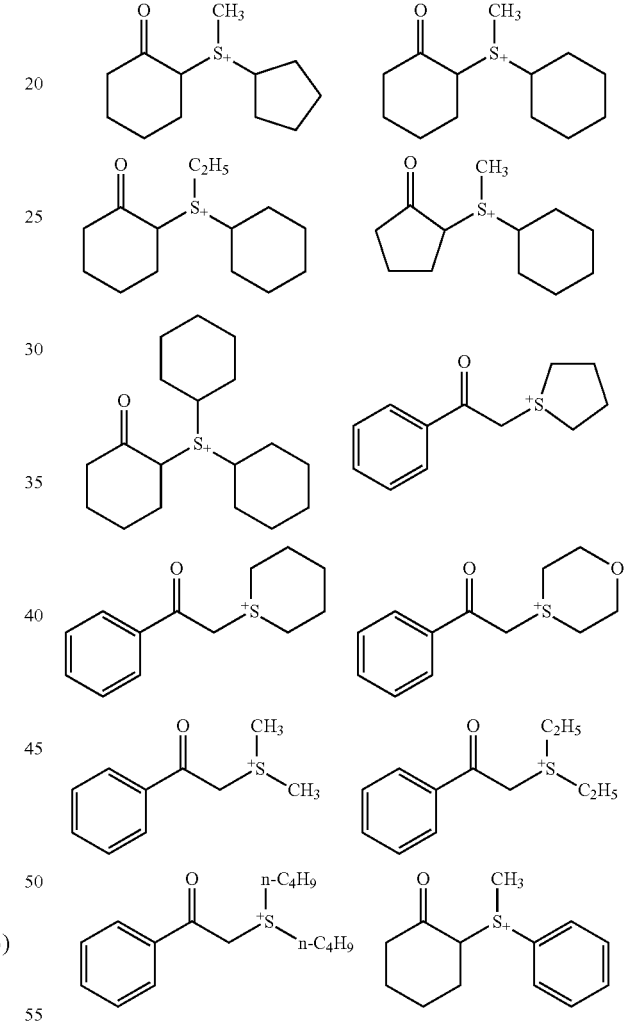
Examples of the cation represented by the formula (Z3) include the followings.
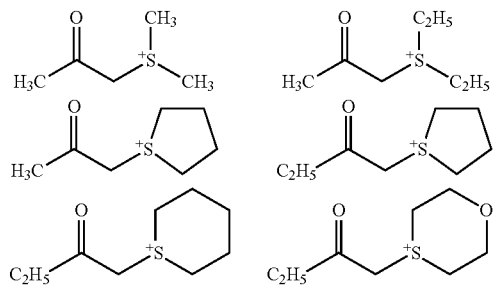
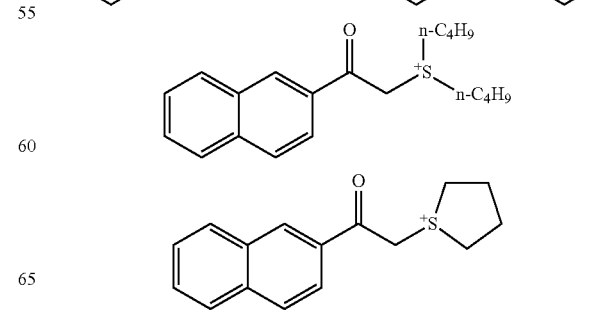

-continued
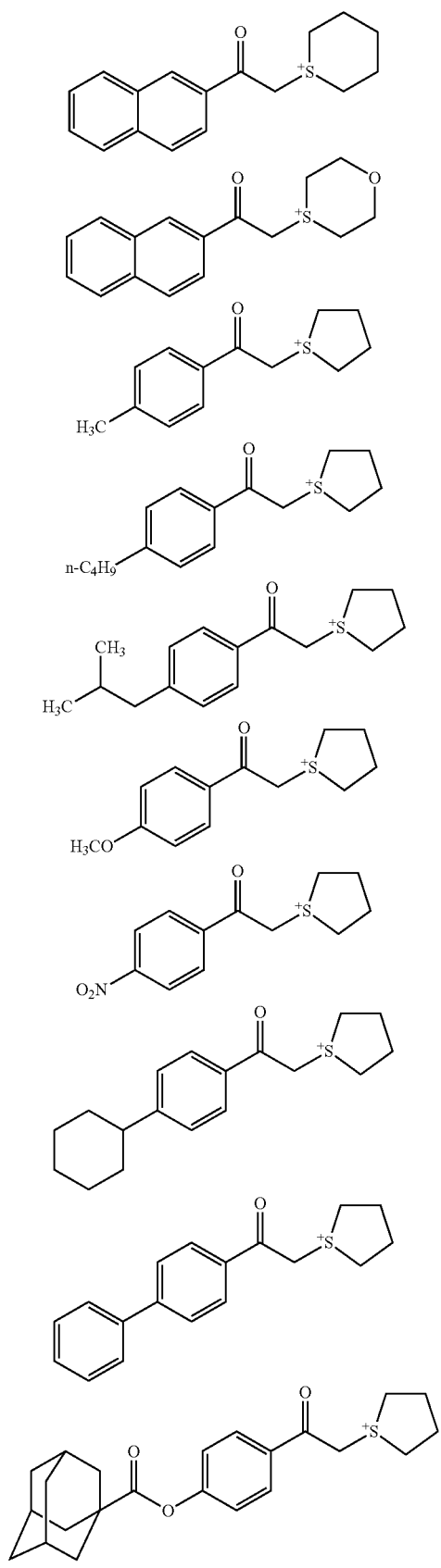
Examples of the cation represented by the formula (Z4) include the followings.
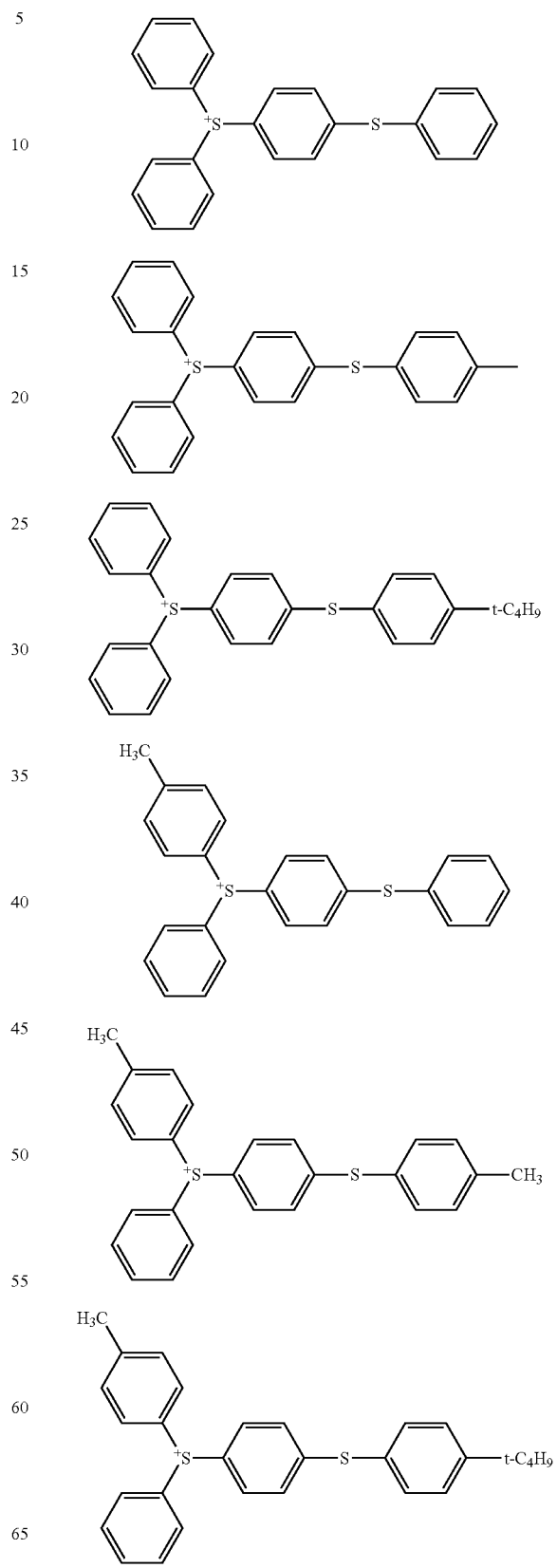

-continued
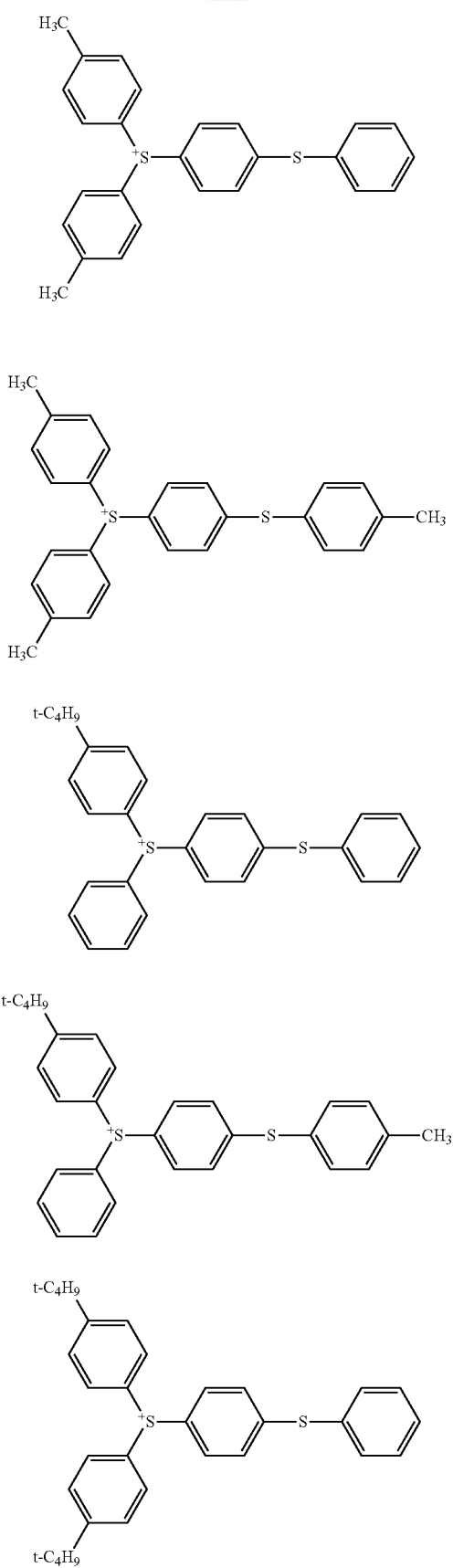
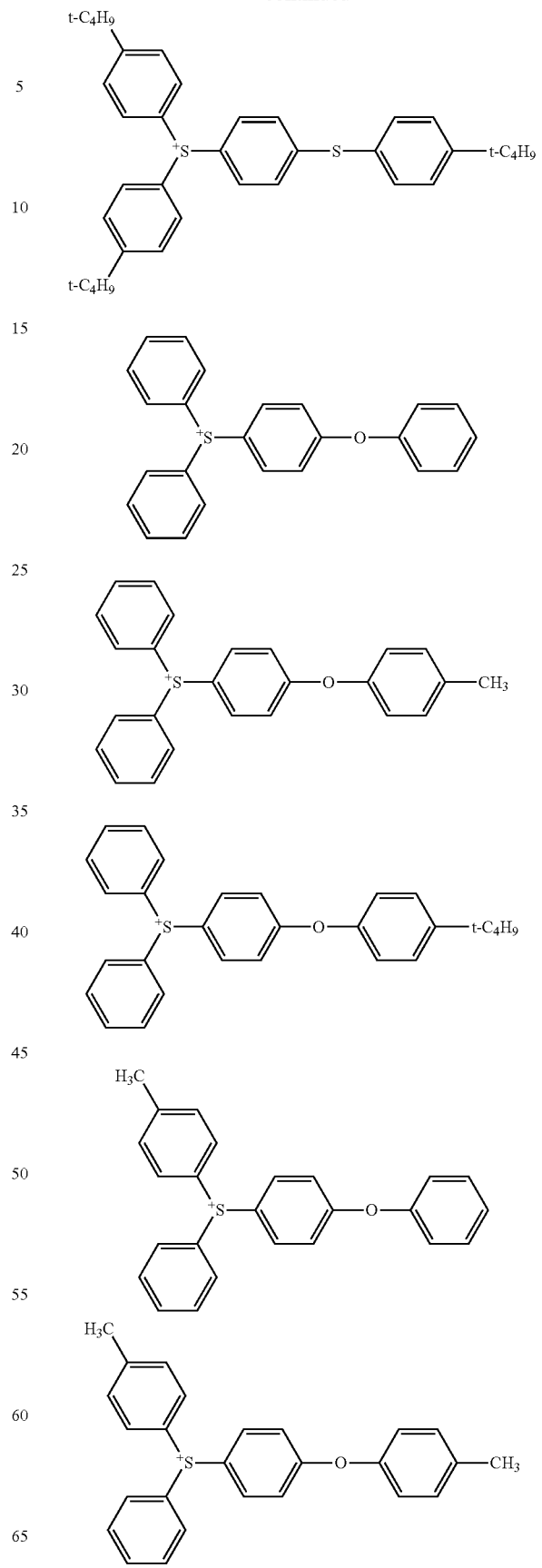

23
-continued
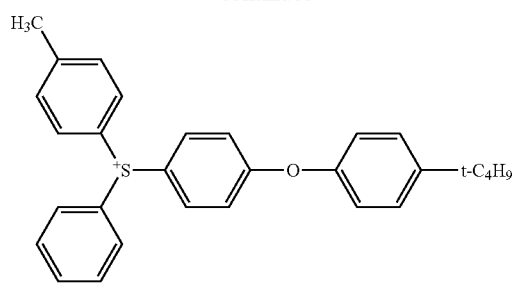
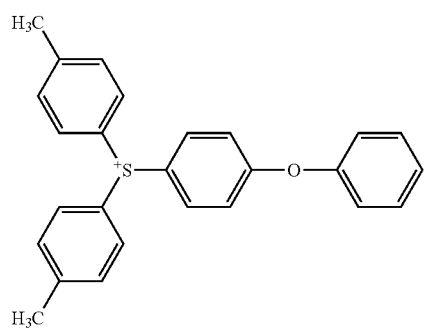
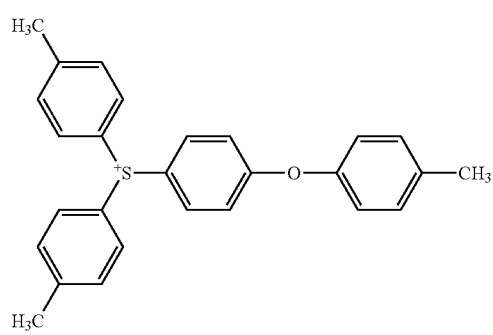
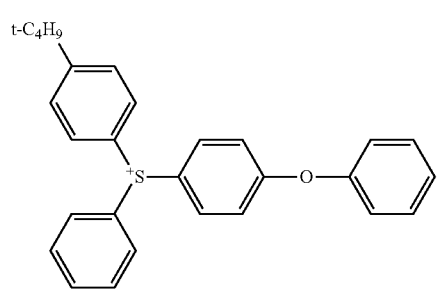
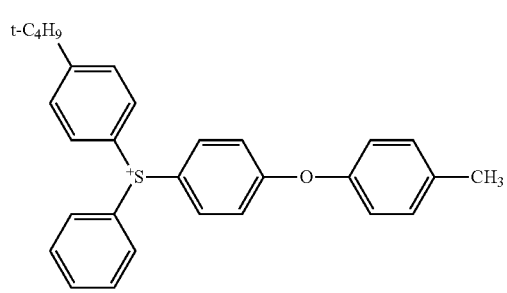
24
-continued
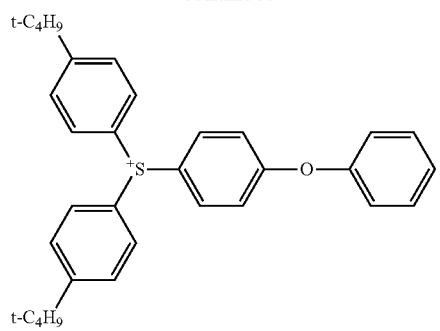
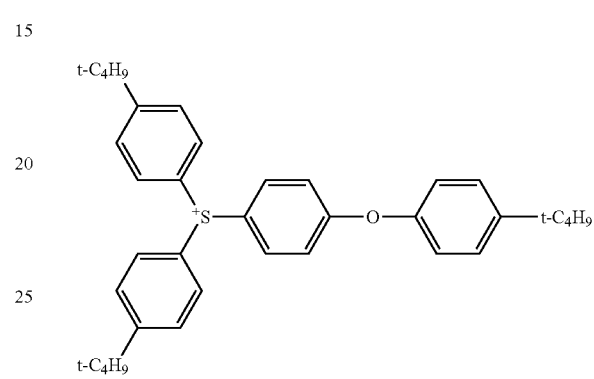
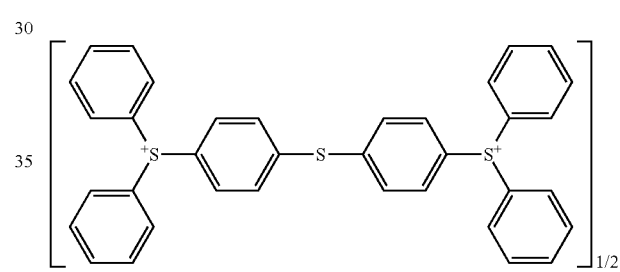
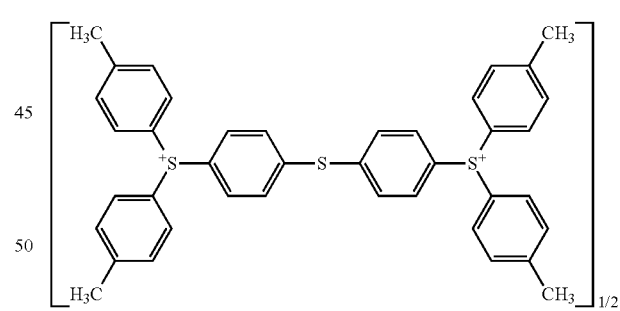
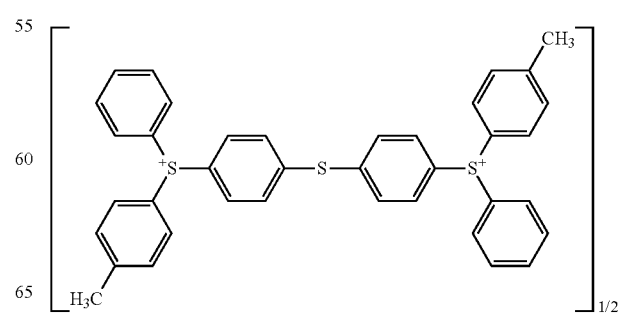

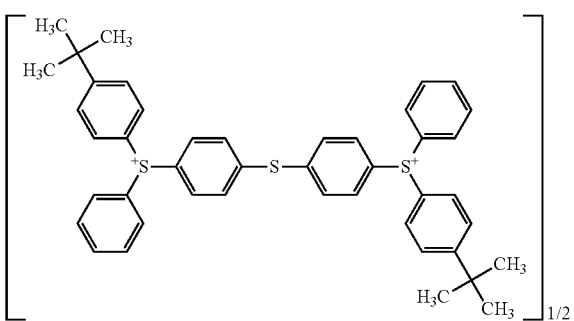
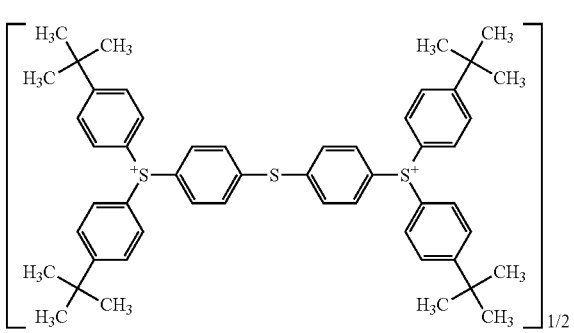
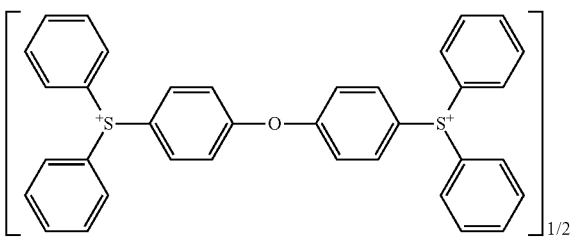
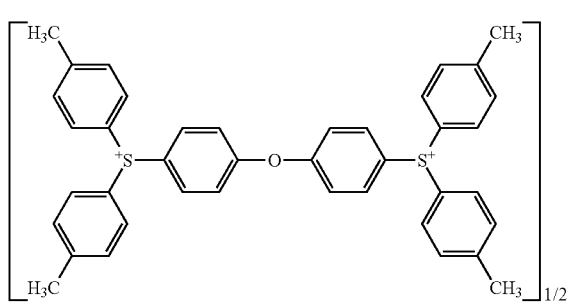
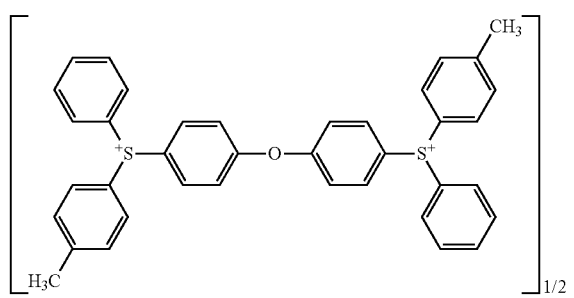
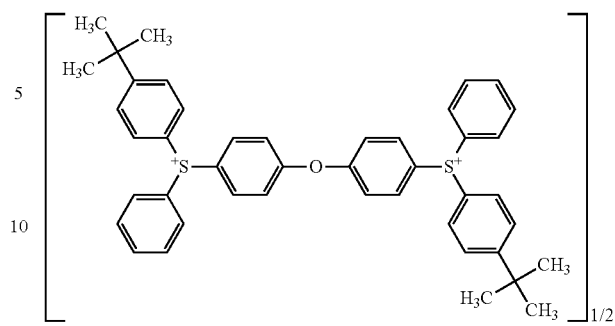
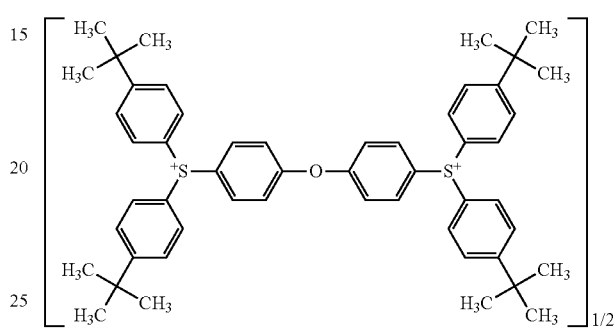
Examples of SALT (I) include a salt wherein the anion part is any one of the above-mentioned anion part and the cation part is any one of the above-mentioned cation part. Specific examples of SALT (I) include the followings.
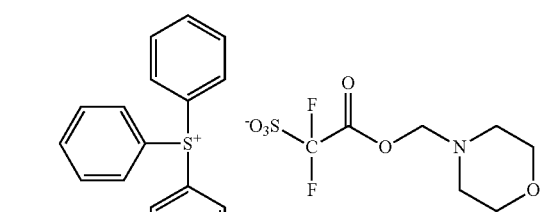
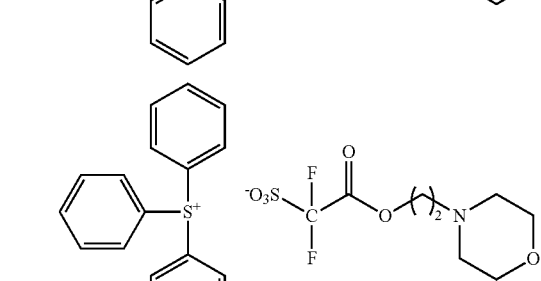
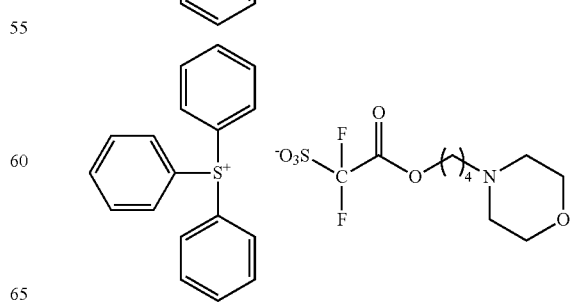

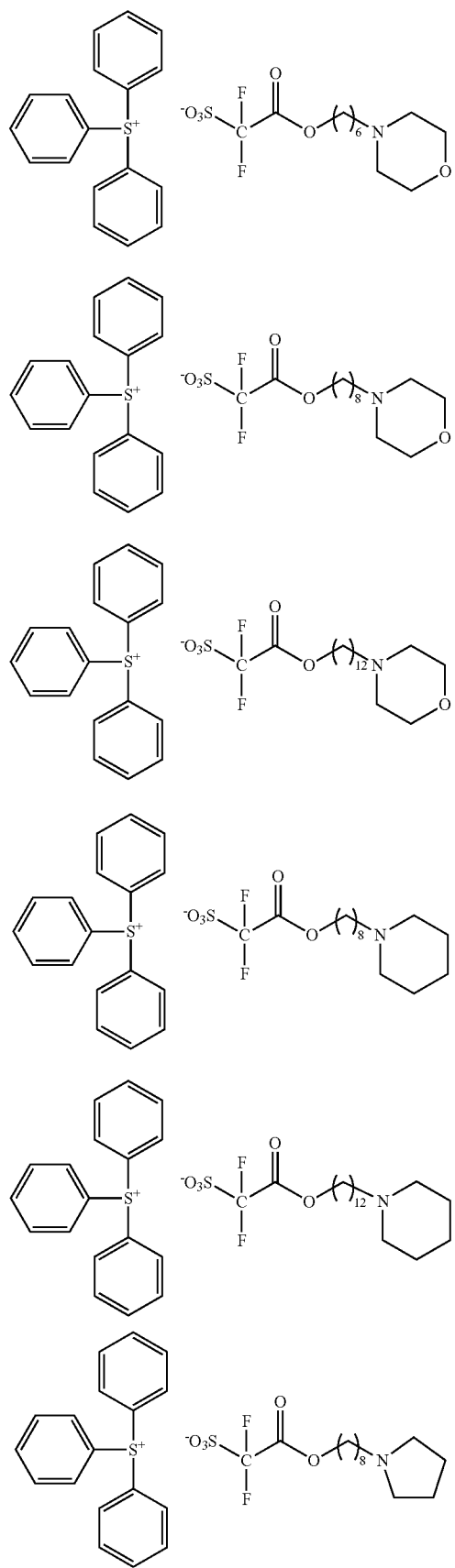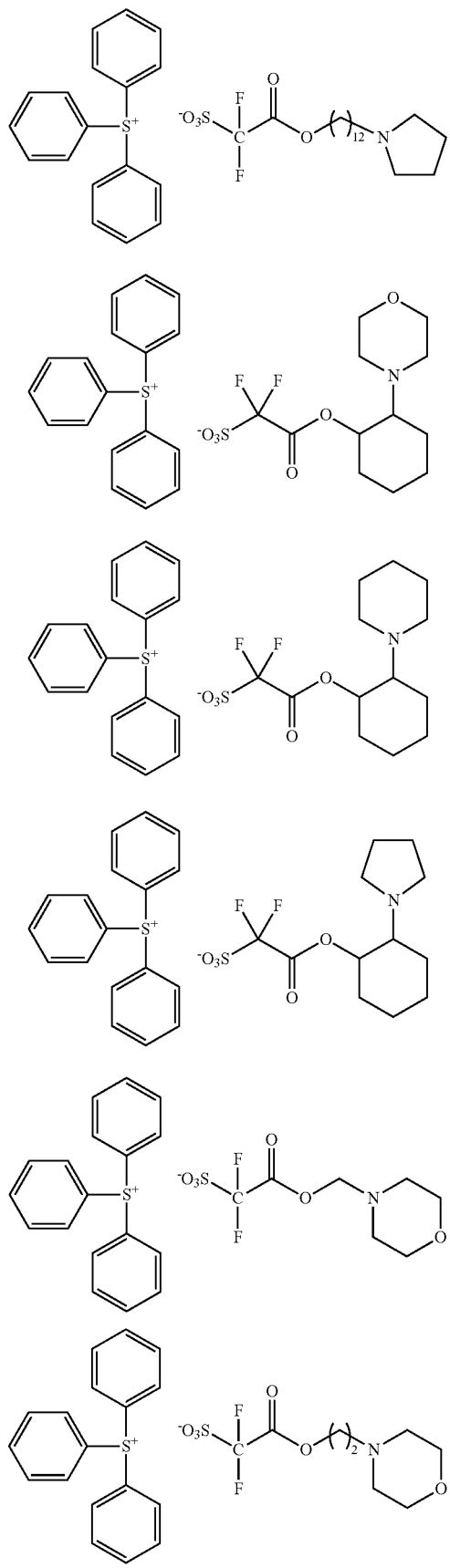

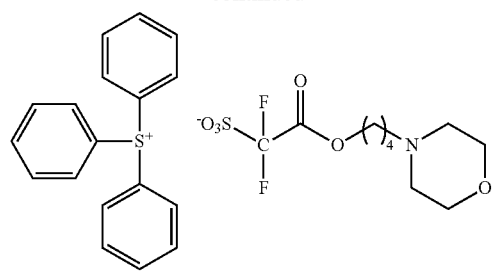
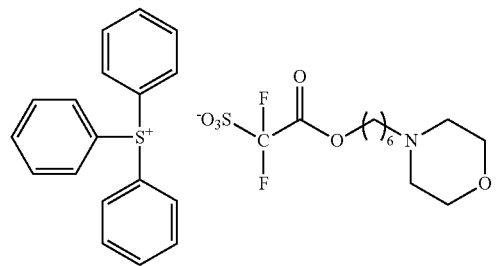
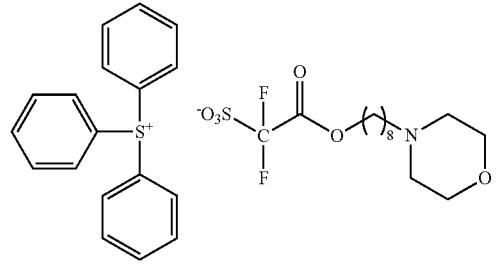
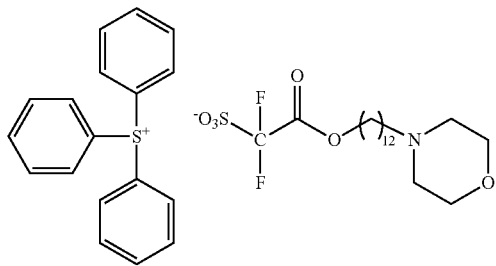
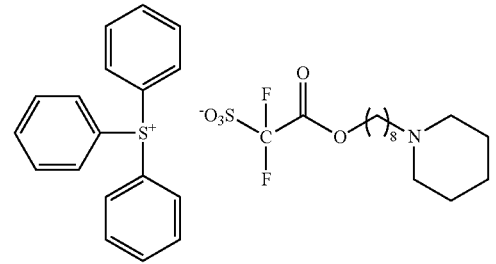
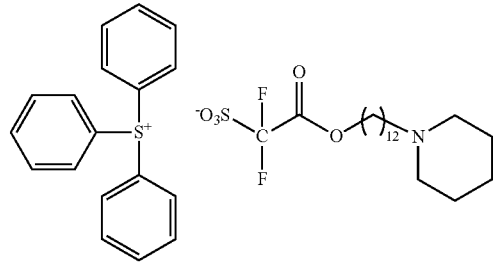
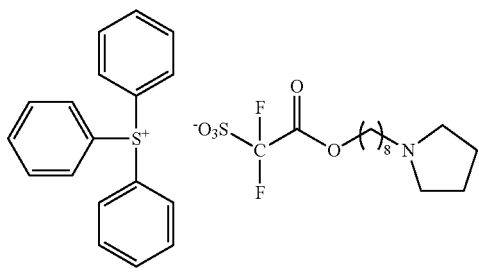
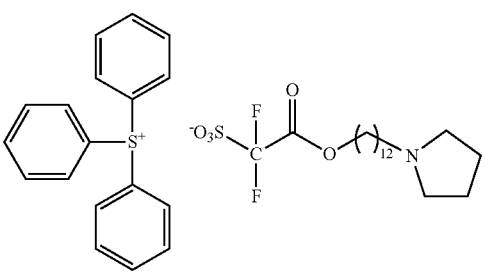
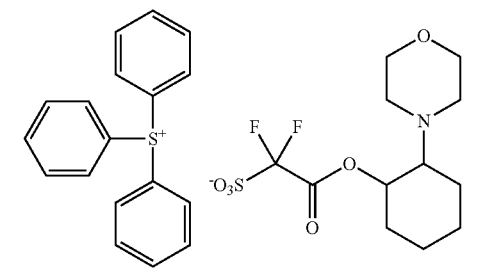
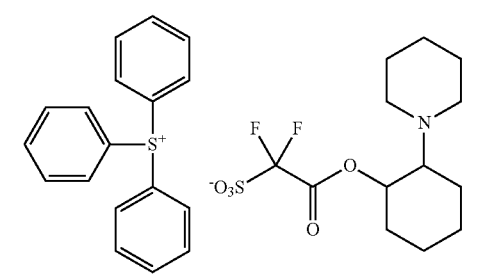
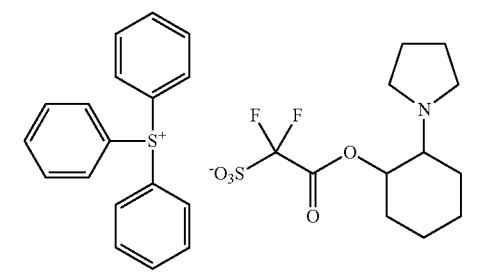
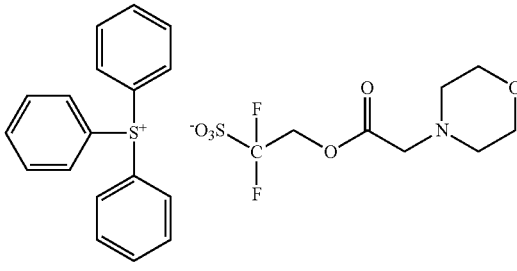

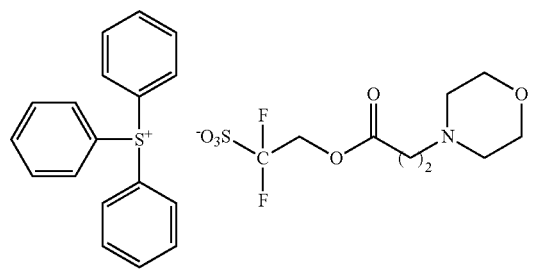
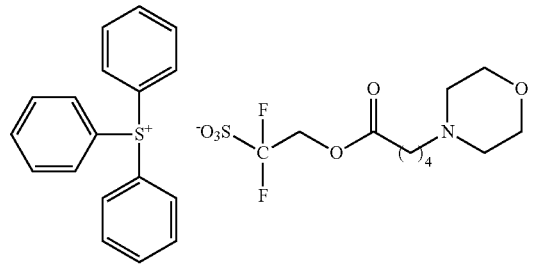
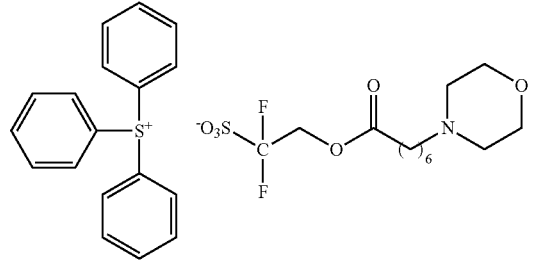
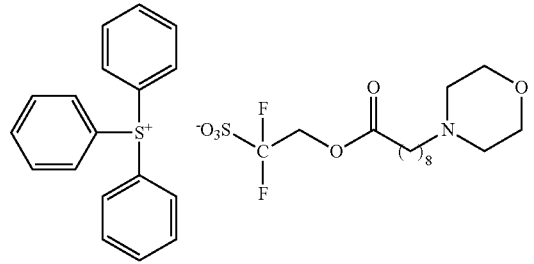
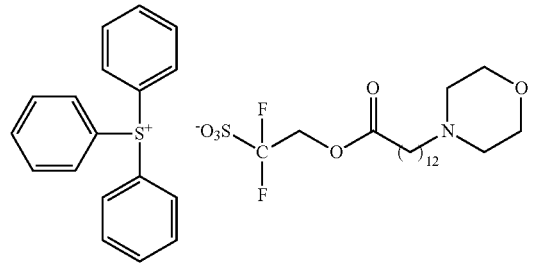
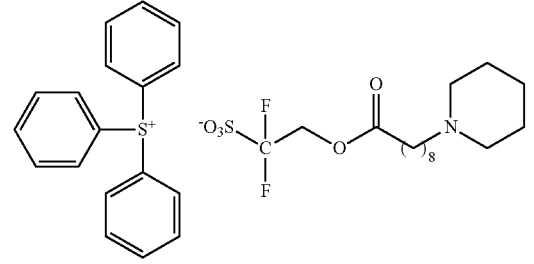
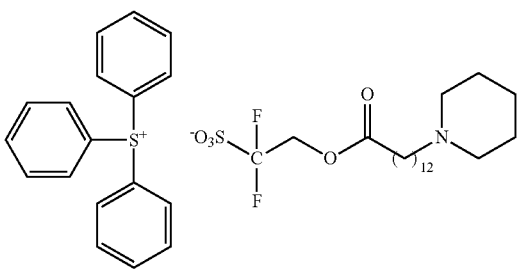
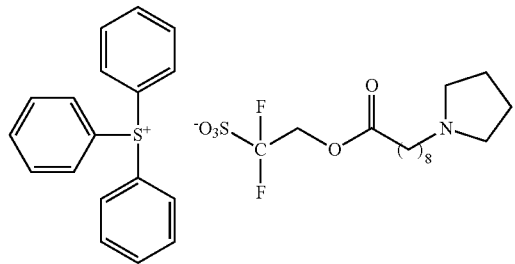
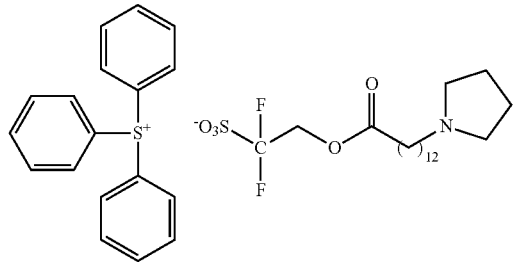
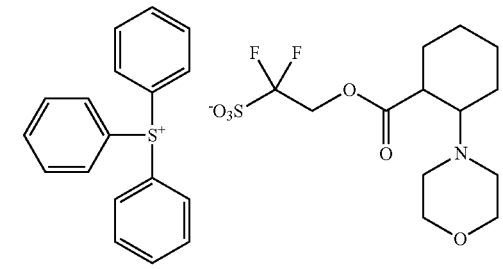
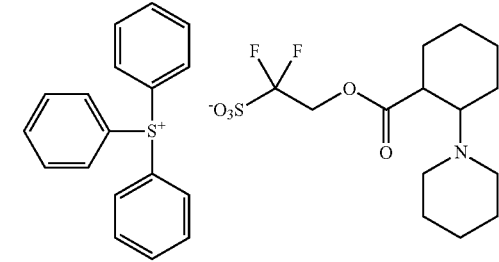
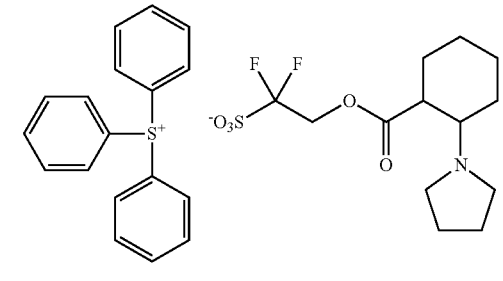

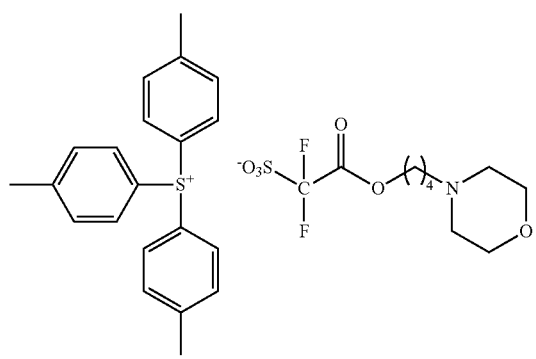
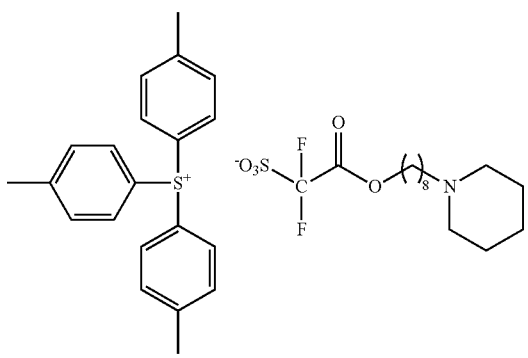

35
-continued
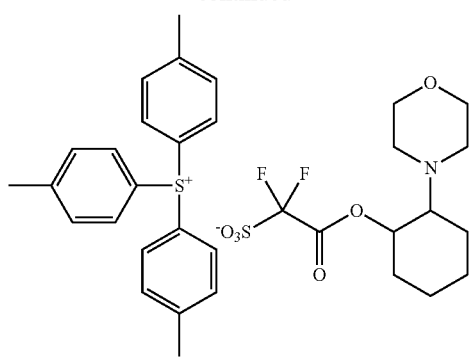
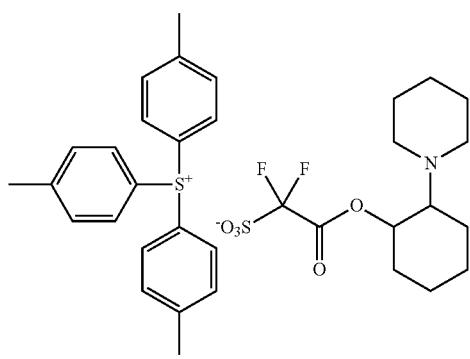
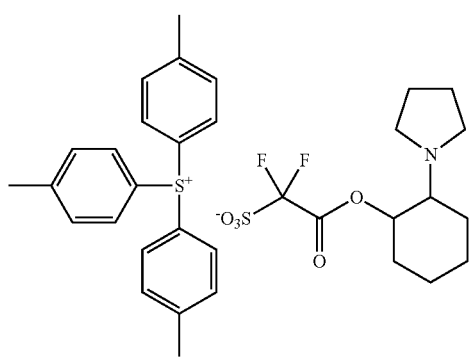
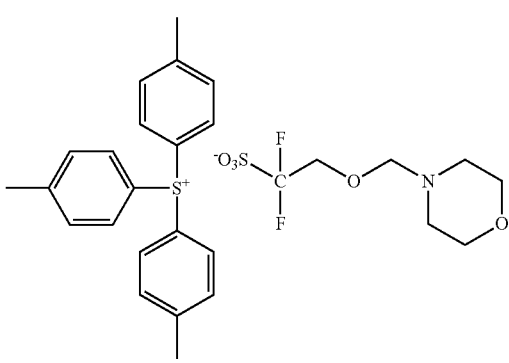
36
-continued
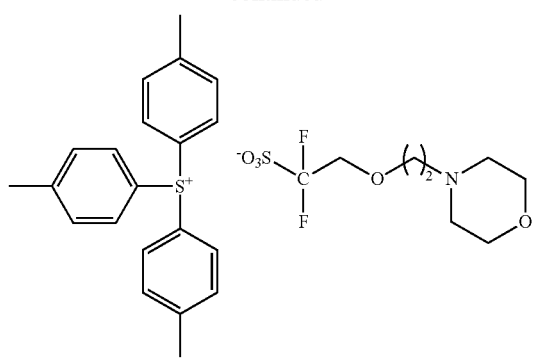
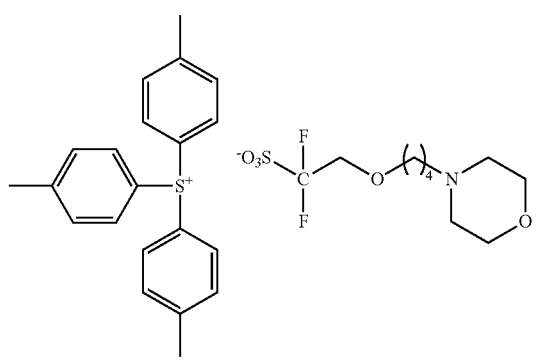
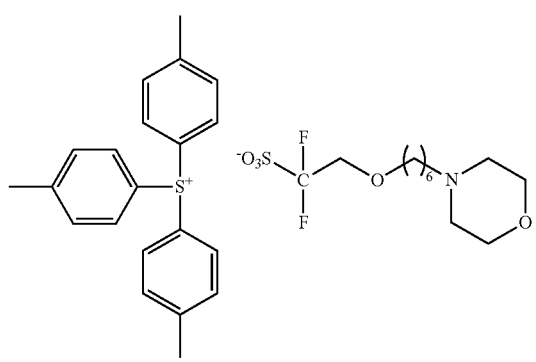
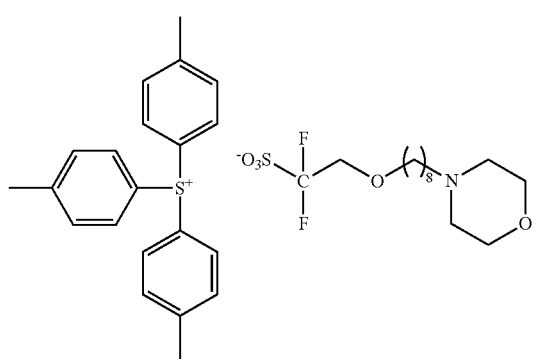

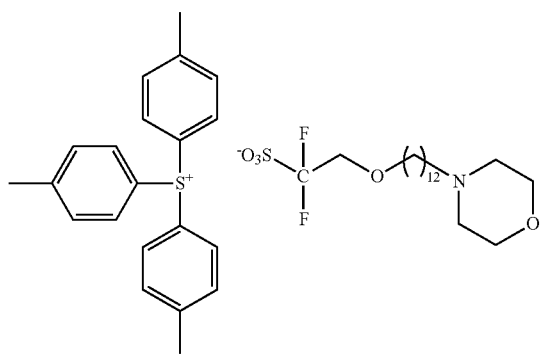
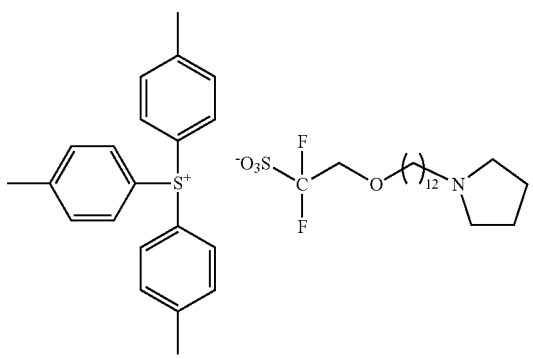
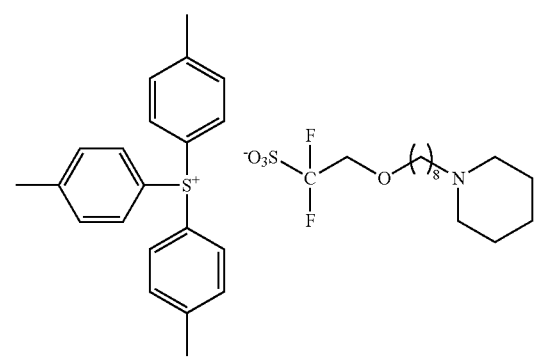
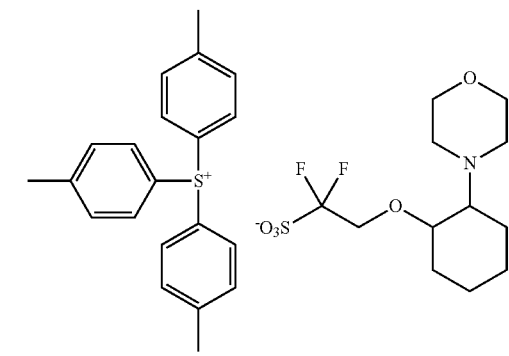
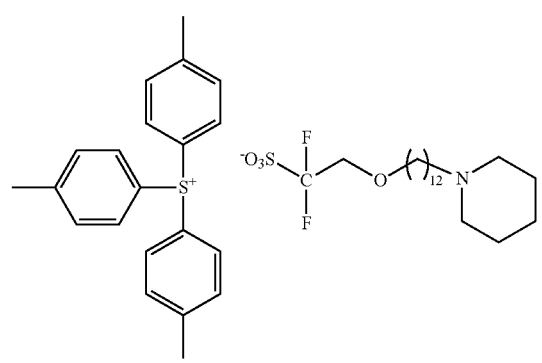
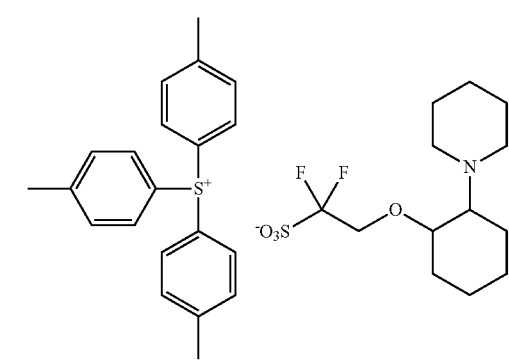
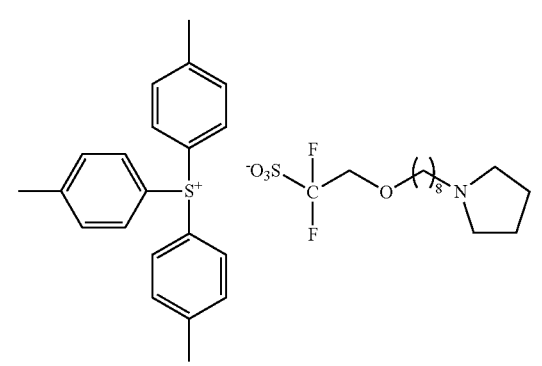
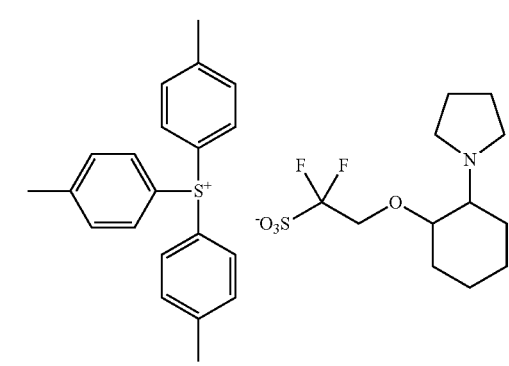

39
-continued
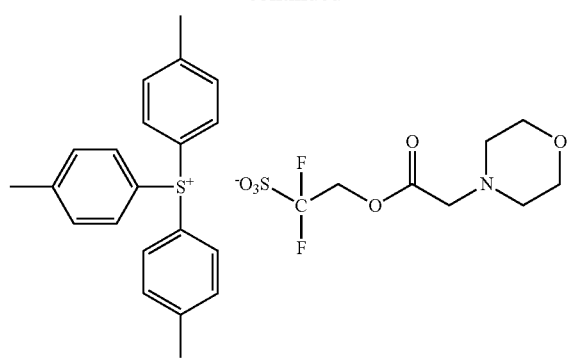
40
-continued
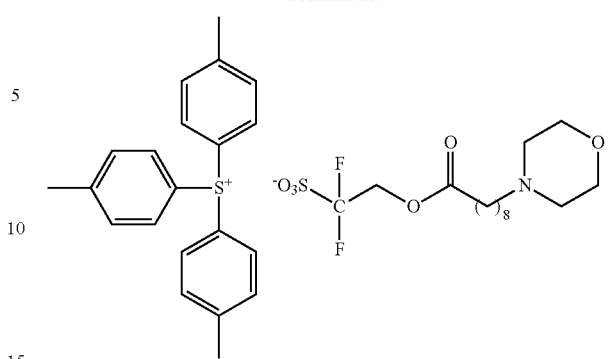
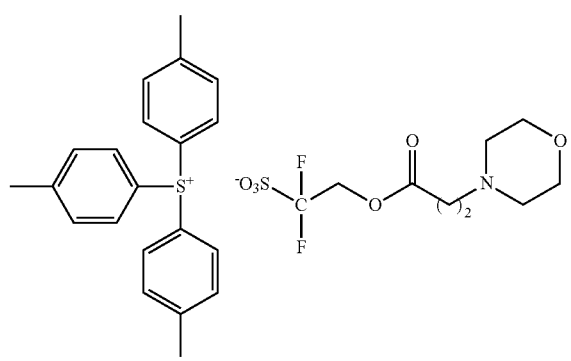
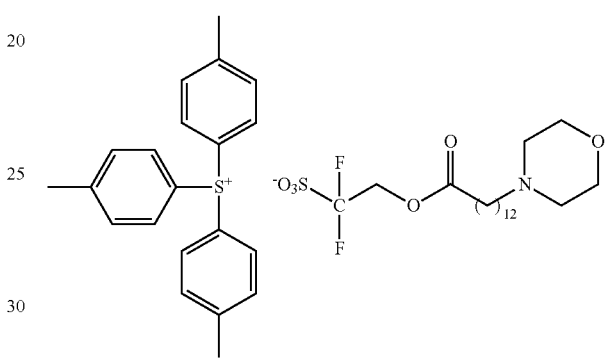
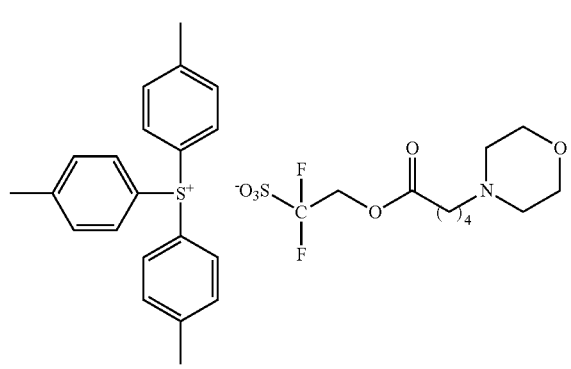
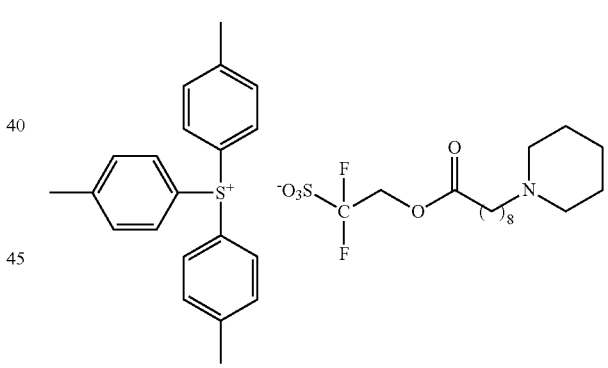
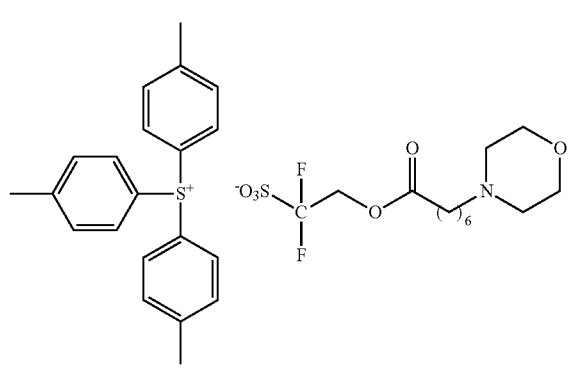
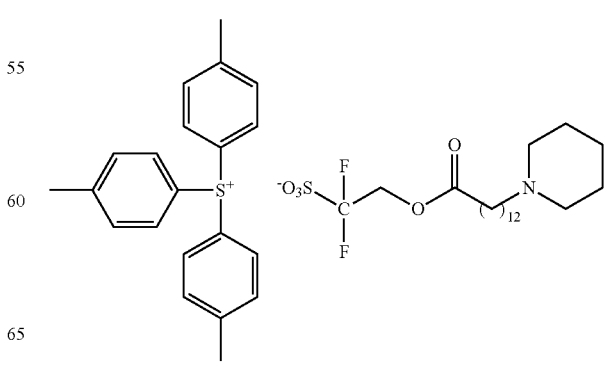

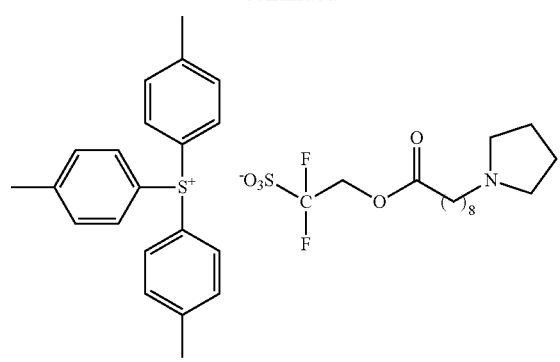
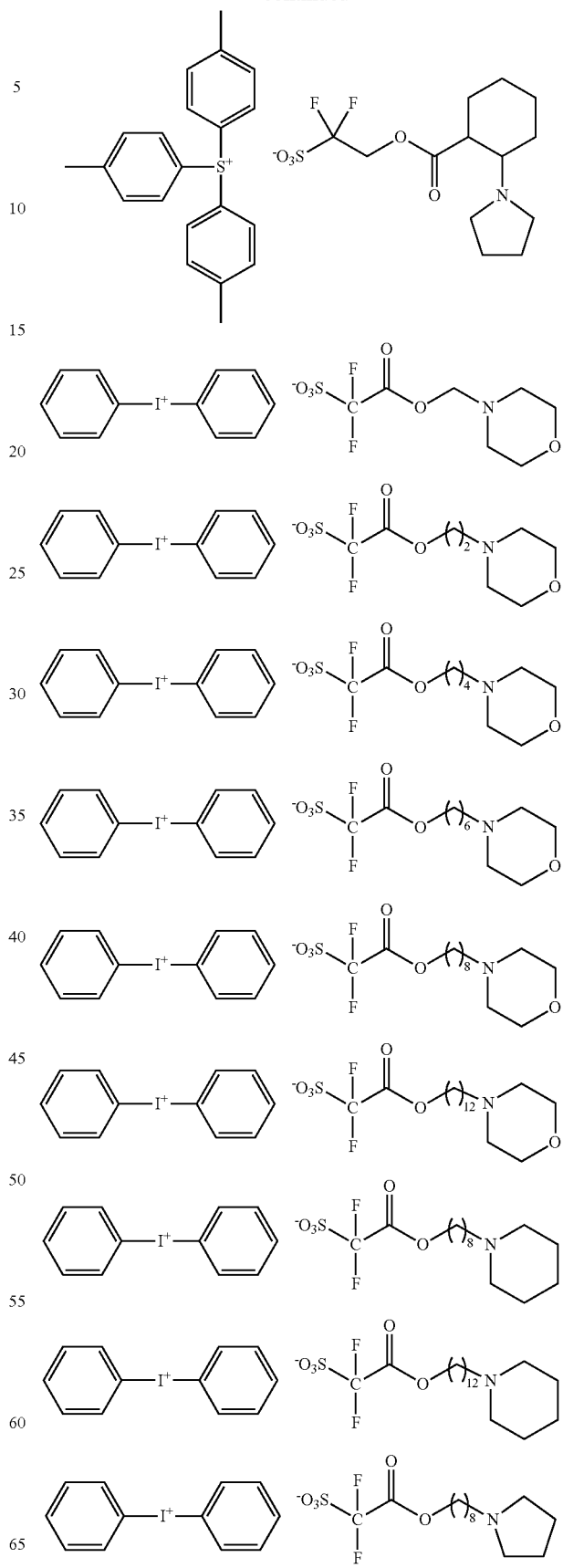

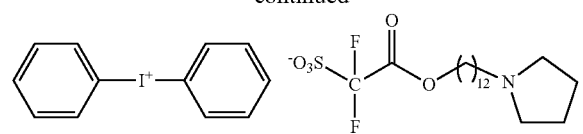
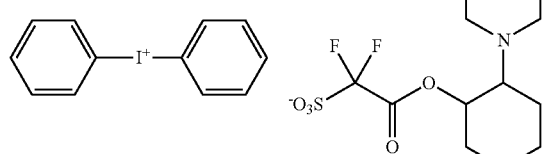
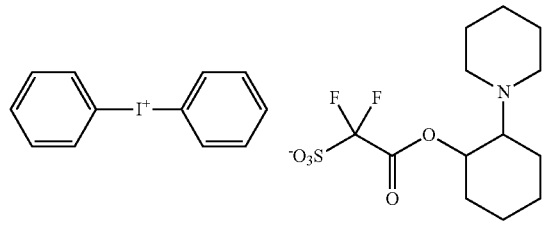
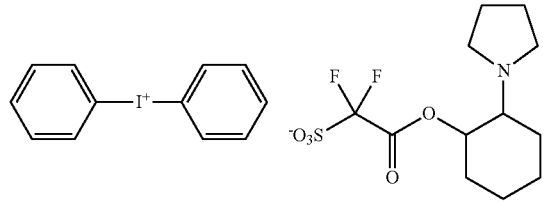
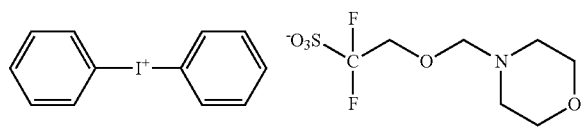
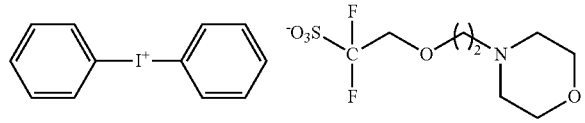
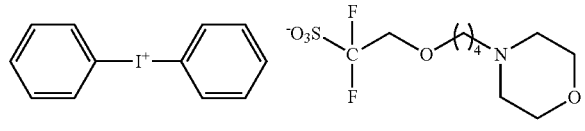
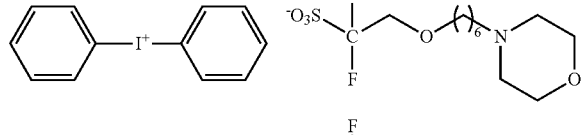
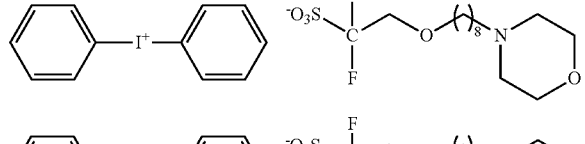
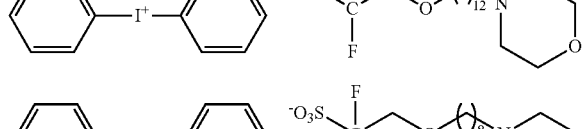
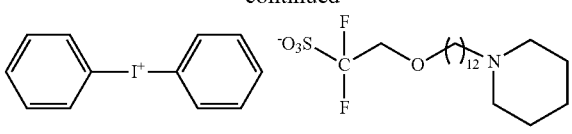
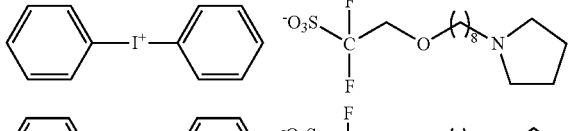
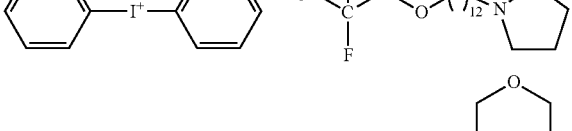
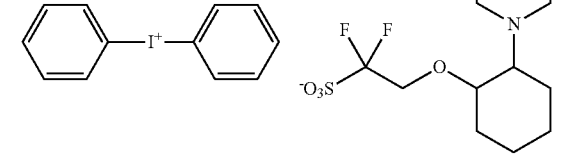
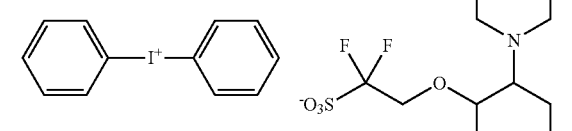
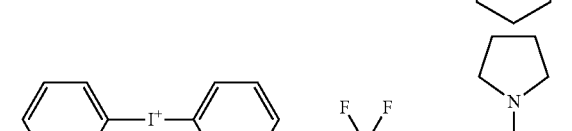
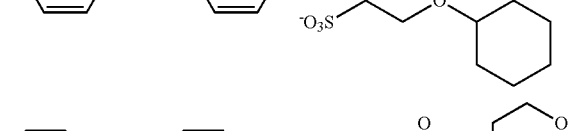
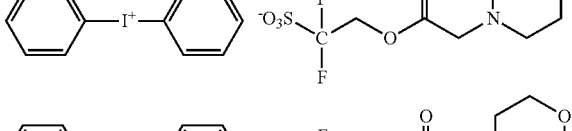
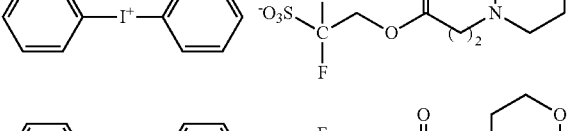
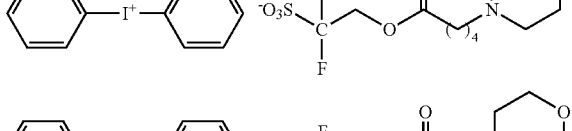
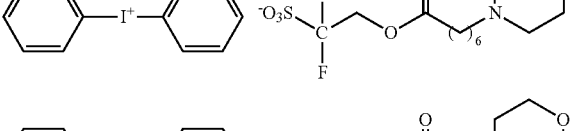
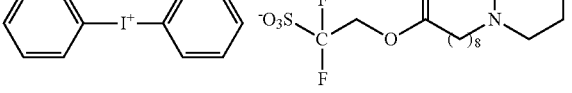
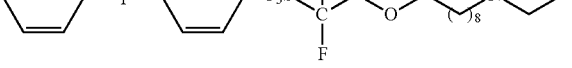

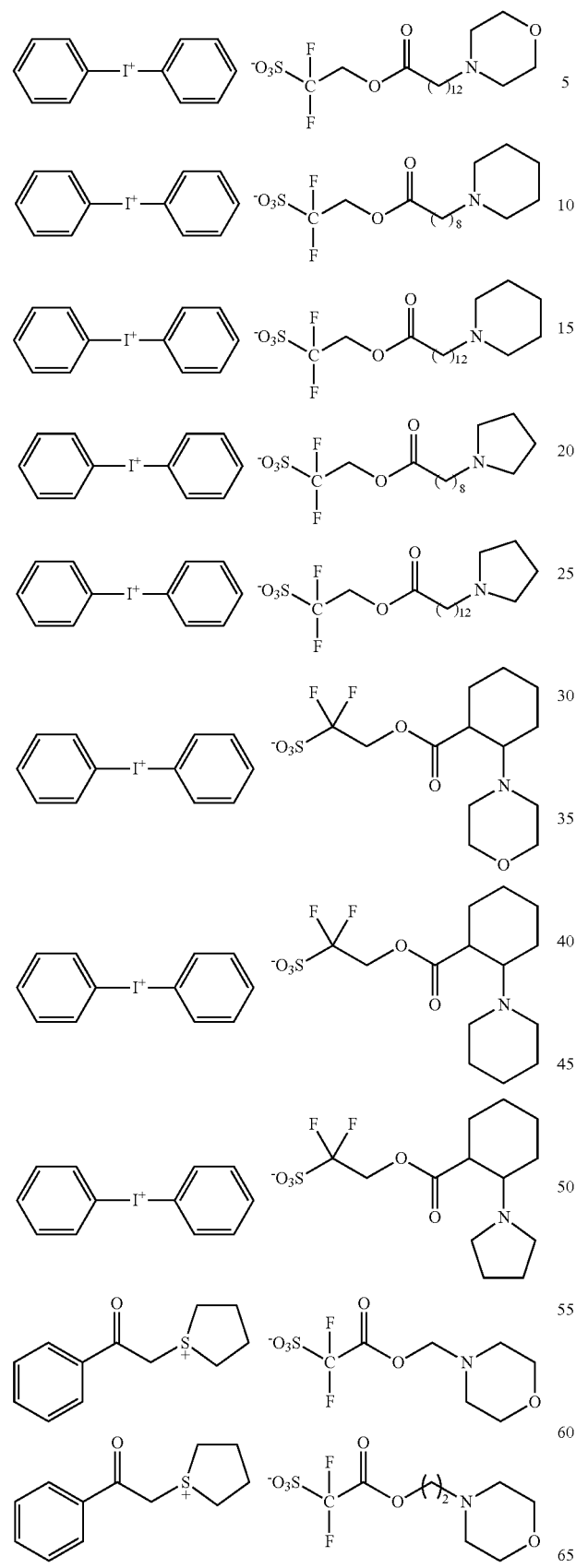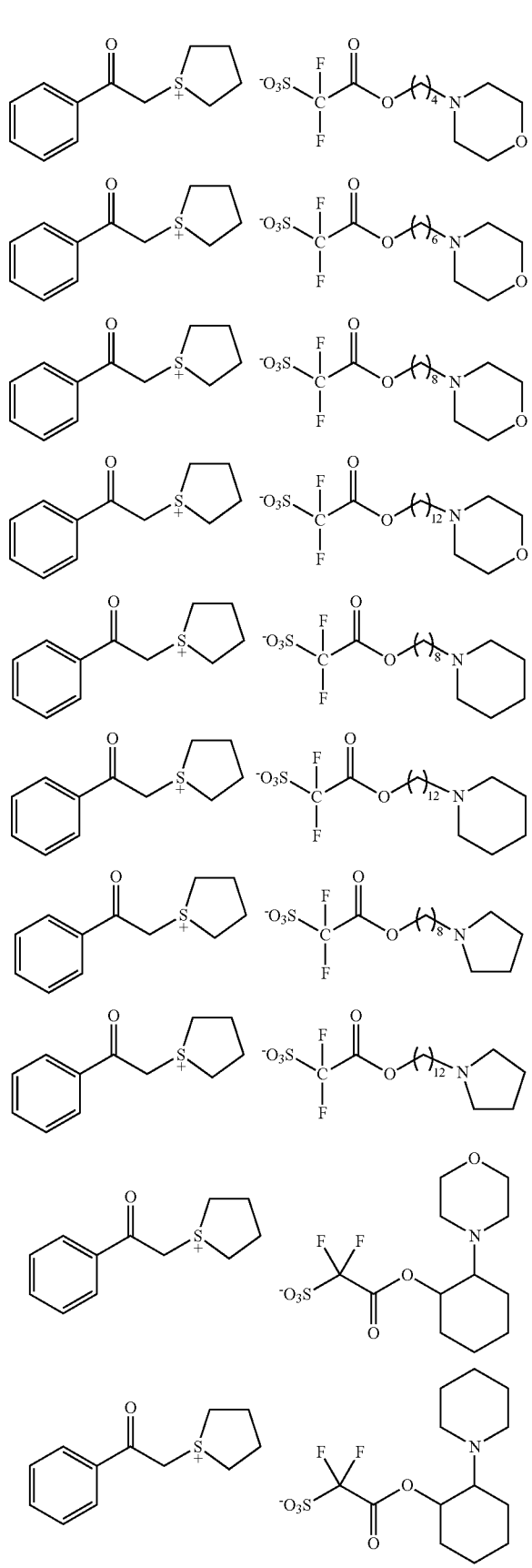

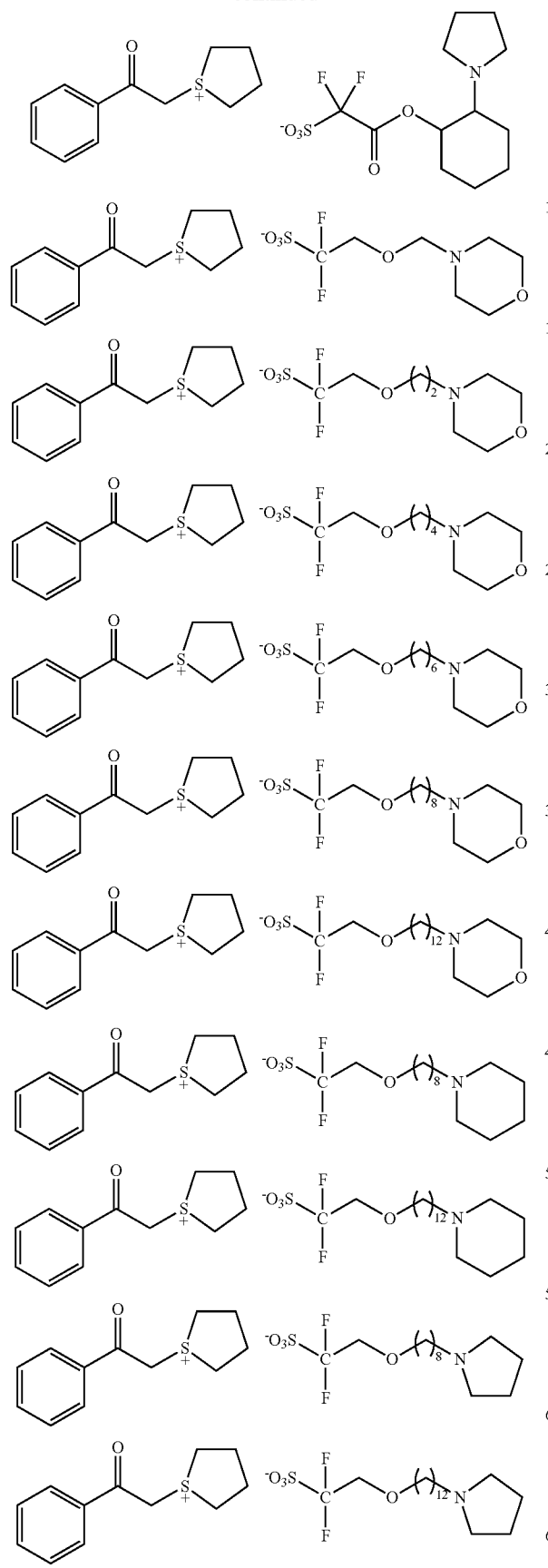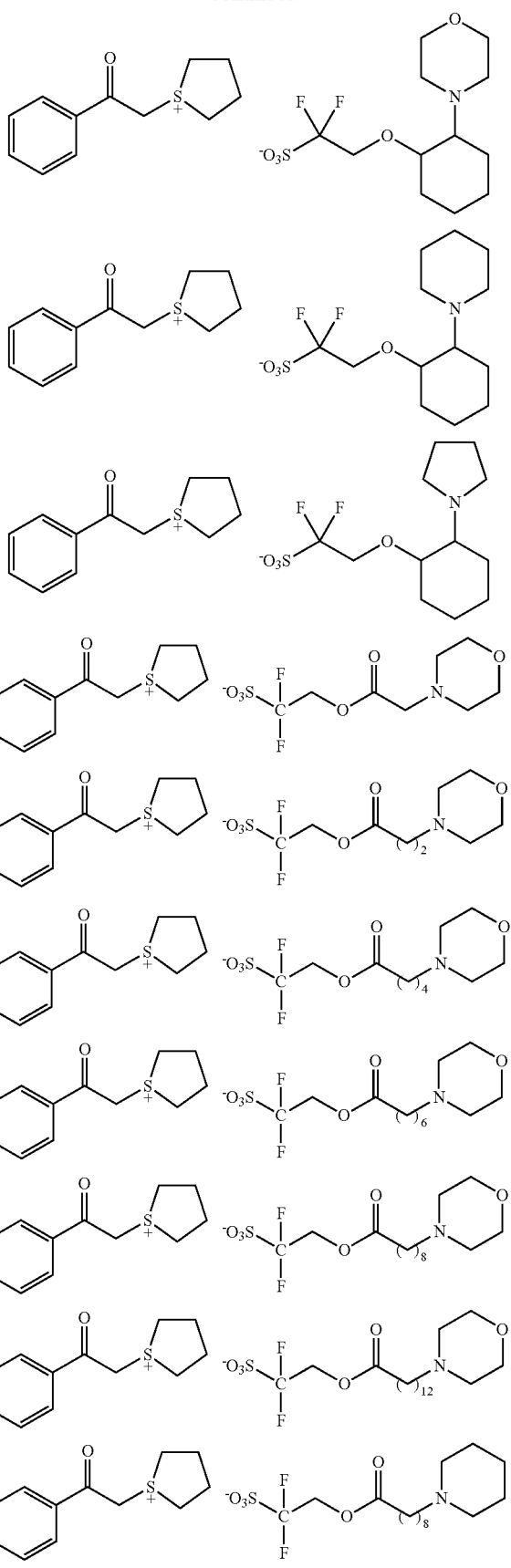

-continued

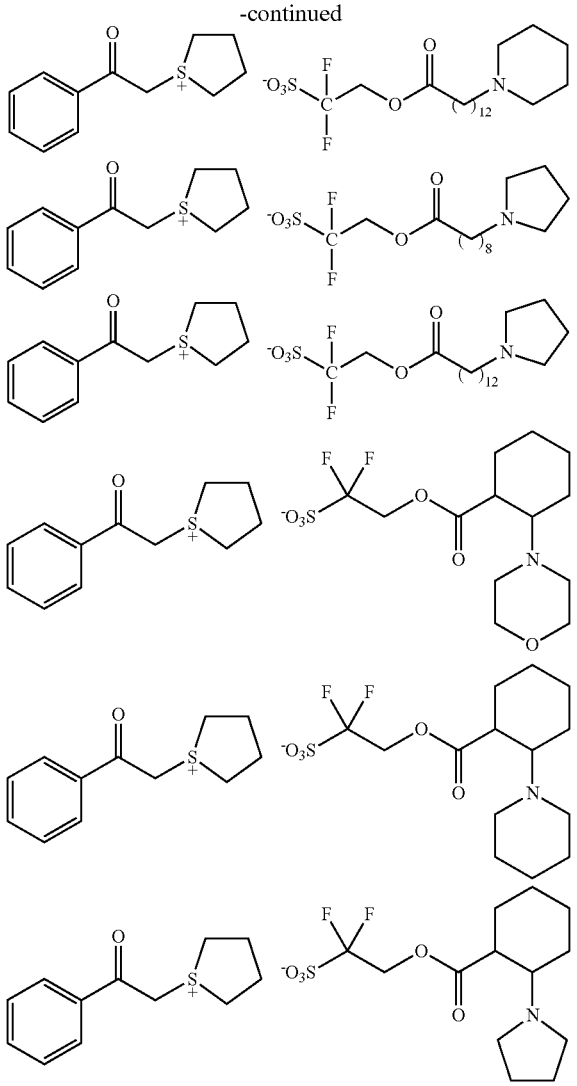

The process for producing SALT (I) will be illustrated.

For example, a salt represented by the formula (Ia) can be produced by reacting a compound represented by the formula (Ib) with a salt represented by the formula (Ic) in a solvent such as chloroform in the presence of a catalyst such as lithium amide.

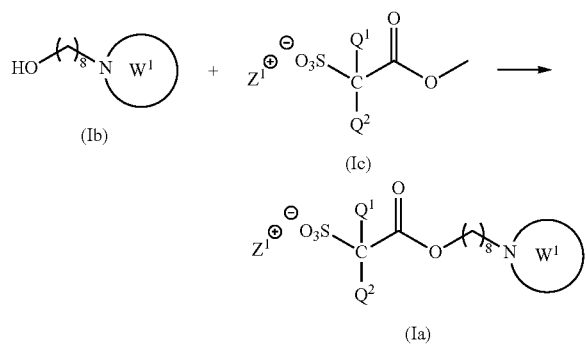

wherein ring $W^1$, $Q^1$, $Q^2$ and $Z^{1\oplus}$ are the same as defined above.

Examples of the compound represented by the formula (Ib) include 4-(8-hydroxyoctyl)morpholine and 4-(2-hydroxyethy)morpholine. The salt represented by the formula (Ic) can be produced according to the method described in JP 2008-13551 A.

For example, a salt represented by the formula (IIIa) can be produced by reacting a compound represented by the formula (IIIb) with a salt represented by the formula (IIIc) in a solvent such as chloroform.

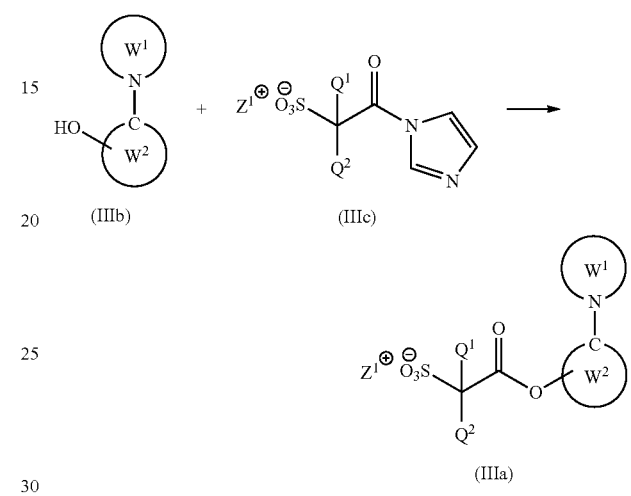

wherein ring $W^1$, $Q^1$, $Q^2$ and $Z^{16}$ are the same as defined above and ring $W^2$ represents a divalent saturated cyclic hydrocarbon group.

The compound represented by the formula (IIIb) can be produced by reacting a compound represented by the formula (IIId) with a compound represented by the formula (IIIe).

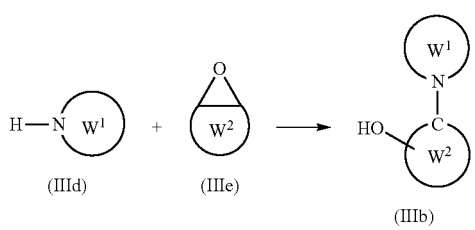

Examples of the compound represented by the formula (IIId) include morpholine, and examples of the compound represented by the formula (IIIe) include 1,2-epoxycyclohexane.

The compound represented by the formula (IIIc) can be produced by reacting a compound represented by the formula (IIIf) with a compound represented by the formula (IIIg).

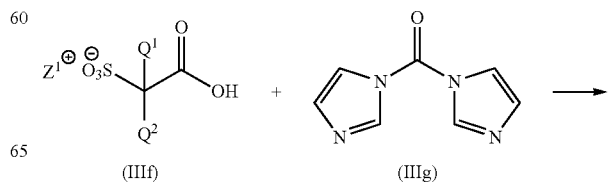

-continued

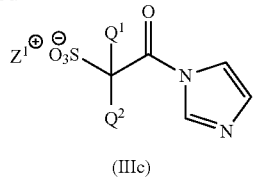

(IIIc)

The compound represented by the formula (IIf) can be produced according to the method described, for example, in JP 2008-13551 A.

The acid generator of the present invention comprises SALT (I). The acid generator of the present invention can contain two or more kinds of SALT (I). The acid generator of the present invention can contain one or more known acid generators in addition to SALT (I). The photoresist composition preferably contains SALT (I) and an acid generator other than SALT (I) as the acid generator.

The photoresist composition comprises the acid generator comprising SALT (I) and a resin.

The content of SALT (I) is usually 0.1 part by weight or more relative to 100 parts by weight of the resin and preferably 0.2 part by weight or more. The content of SALT (I) is usually 10 parts by weight or less relative to 100 parts by weight of the resin and preferably 5 parts by weight or less.

The acid generators other than SALT (I) that may be used include nonionic acid generators and ionic acid generators. Examples of the nonionic acid generator include organic halides, sulfonate esters such as 2-nitrobenzyl ester, aromatic sulfonate, oxime sulfonate, N-sulfonyloxyimide, sulfonyloxyketone and DNQ 4-sulfonate, and sulfones such as disulfone, ketosulfone and sulfonyldiazomethane. Examples of the ionic acid generator include onium salts such as a diazonium salt, a phosphonium salt, a sulfonium salt and an iodonium salt, and examples of the anion of the onium salt include sulfonic acid anion, sulfonylimide anion and sulfonylmethide anion.

Other examples of the acid generator include acid generators described in JP 63-26653A, JP 55-164824 A, JP 62-69263A, JP 63-146038 A, JP 63-163452 A, JP 62-153853 A, JP 63-146029 A, U.S. Pat. No. 3,779,778, U.S. Pat. No. 3,849,137, DE Patent No. 3914407 and EP Patent No. 126,712.

A fluorine-containing acid generator is preferable.

Preferable examples of the acid generator include a salt represented by the formula (II):

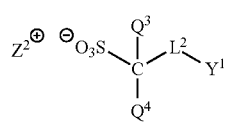

(II)

wherein $Q^3$ and $Q^4$ independently represent a fluorine atom or a C1-C6 perfluoroalkyl group,
$L^2$ represents a C1-C17 saturated divalent hydrocarbon group in which one or more —$CH_2$— can be replaced by —O— or —CO— and which can have one or more substituents,
$Y^1$ represents a C1-C36 aliphatic hydrocarbon group or a C3-C36 saturated cyclic hydrocarbon group, and the aliphatic hydrocarbon group and the saturated cyclic hydrocarbon group can have one or more substituents, and one or more —$CH_2$— in the aliphatic hydrocarbon group and the saturated cyclic hydrocarbon group can be replaced by —O—, —CO— or —$SO_2$—, and
$Z^{2\oplus}$ represents an organic cation.

Examples of the C1-C6 perfluoroalkyl group include the same as described above in $Q^1$ and $Q^2$. $Q^3$ and $Q^4$ independently preferably represent a fluorine atom or a trifluoromethyl group, and $Q^3$ and $Q^4$ are more preferably fluorine atoms.

Examples of the C1-C17 saturated divalent hydrocarbon group include a C1-C17 alkylene group and a divalent group having an alicyclic divalent hydrocarbon group. Examples of the alkylene group include a linear alkanediyl group such as a methylene group, an ethylene group, a propane-1,3-diyl group, a butane-1,4-diyl group, a pentane-1,5-diyl, a hexane-1,6-diyl group, a heptane-1,7-diyl group, an octane-1,8-diyl group, a nonane-1,9-diyl group, a decane-1,10-diyl group, an undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group and a heptadecane-1,17-diyl group, a branched chain alkanediyl group formed by replacing one or more hydrogen atom of the above-mentioned linear alkanediyl group by a C1-C4 alkyl group, and
a divalent group having an alicyclic divalent hydrocarbon group such as the following groups represented by the formulae ($X^1$-A) to ($X^1$-C):

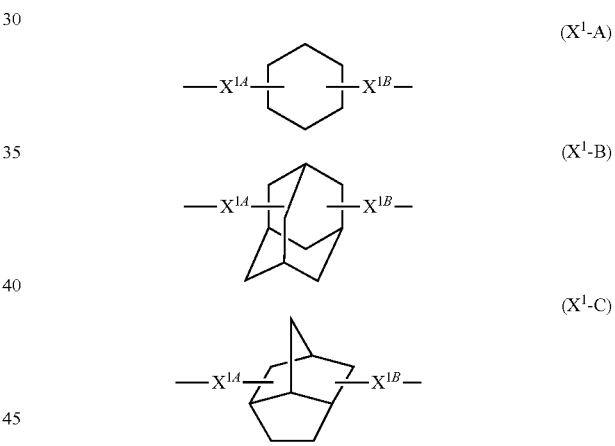

wherein $X^{1A}$ and $X^{1B}$ independently each represent a C1-C6 alkylene group which can have one or more substituents, with the proviso that total carbon number of the group represented by the formula ($X^1$-A), ($X^1$-B) or ($X^1$-C) is 1 to 17.

One or more —$CH_2$— in the C1-C6 alkylene group can be replaced by —O— or —CO—.

Examples of the C1-C17 saturated hydrocarbon group in which one or more —$CH_2$— are replaced by —O— or —CO— include *—CO—O-$L^d$-, *—CO—O-$L^f$-CO—O-$L^e$-, *-$L^g$-O—CO—, *-$L^i$-O-$L^h$-, *—CO—O-$L^j$-O— and *—CO—O-$L^m$-O-$L^k$-CO—O—, wherein $L^d$ represents a single bond or a C1-C15 saturated hydrocarbon group, $L^e$ represents a single bond or a C1-C12 saturated hydrocarbon group, $L^f$ represents a C1-C13 saturated hydrocarbon group, with the proviso that total carbon number of $L^e$ and $L^f$ is 1 to 13, $L^g$ represents a C1-C15 saturated hydrocarbon group, $L^h$ represents a C1-C15 saturated hydrocarbon group, $L^i$ represents a C1-C15 saturated hydrocarbon group, with the proviso that total carbon number of $L^h$ and $L^i$ is 1 to 16, $L^j$ represents a C1-C14 saturated hydrocarbon group, $L^k$ represents a C1-C11 saturated hydrocarbon group, $L^m$ represents a C1-C11 saturated hydrocarbon group, with the proviso that total carbon number of $L^k$ and $L^m$ is 1 to 12, and * represents a binding position to —C(Q³)(Q⁴)-. Among them, preferred is *—CO—O-$L^d$-, and more preferred is *—CO—O-$L^d$- in which $L^d$ is a single bond or —CH₂—.

Examples of *—CO—O-$L^d$-include *—CO—O— and *—CO—O—CH₂—. Examples of *—CO—O-$L^f$-CO—O-$L^e$-include *—CO—O—CH₂—CO—O—, *—CO—O—(CH₂)₂—CO—O—, *—CO—O— (CH₂)₃—CO—O—, *—CO—O— (CH₂)₄—CO—O—, *—CO—O—(CH₂)₆—CO—O—, *—CO—O—(CH₂)₈—CO—O—, *—CO—O—CH₂—CH(CH₃)—CO—O— and *—CO—O—CH₂—C(CH₃)₂—CO—O—. Examples of *-$L^g$-O—CO— include *—CH₂—O—CO—, *—(CH₂)₂—O—CO—, *—(CH₂)₃—O—CO—, *—(CH₂)₄—O—CO—, *—(CH₂)₆—O—CO— and *—(CH₂)₈—O—CO—. Examples of *-$L^i$-O-$L^h$-include *—CH₂—O—CH₂—. Examples of *—CO—O-$L^3$-O— include *—CO—O—CH₂—O—, *—CO—O—(CH₂)₂—O—, *—CO—O—(CH₂)₃—O—, *—CO—O— (CH₂)₄—O— and *—CO—O—(CH₂)₆—O—. Examples of *—CO—O-$L^m$-O-$L^k$-CO—O— include the followings.

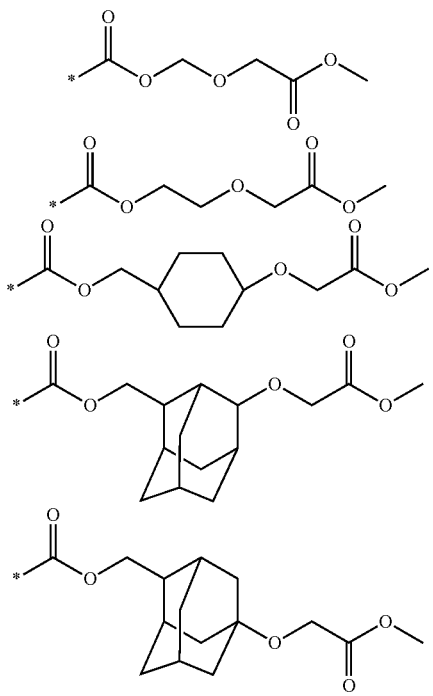

Examples of the substituent in $Y^1$ include a halogen atom excluding a fluorine atom, a hydroxyl group, an oxo group, a glycidyloxy group, a C2-C4 acyl group, a C1-C12 alkoxy group, a C2-C7 alkoxycarbonyl group, a C1-C12 aliphatic hydrocarbon group, a C1-C12 hydroxy-containing aliphatic hydrocarbon group, a C3-C16 saturated cyclic hydrocarbon group, a C6-C18 aromatic hydrocarbon group, a C7-C21 aralkyl group and —(CH₂)$_{j2}$—O—CO— in which $R^{b1}$ represents a C1-C16 aliphatic hydrocarbon group, a C3-C16 saturated cyclic hydrocarbon group or a C6-C18 aromatic hydrocarbon group and j2 represents an integer of 0 to 4. Examples of the halogen atom include a fluorine atom, a chlorine atom, a bromine atom and an iodine atom. Examples of the acyl group include an acetyl group and a propionyl group, and examples of the alkoxy group include a methoxy group, an ethoxy group, a propoxy group, an isopropoxy group and a butoxy group. Examples of the alkoxycarbonyl group include a methoxycarbonyl group, an ethoxycarbonyl group, a propoxycarbonyl group, an isopropoxycarbonyl group and a butoxycarbonyl group. Examples of the aliphatic hydrocarbon group include the same as described above. Examples of the hydroxyl-containing aliphatic hydrocarbon group include a hydroxymethyl group. Examples of the C3-C16 saturated cyclic hydrocarbon group include the same as described above, and examples of the aromatic hydrocarbon group include a phenyl group, a naphthyl group, an anthryl group, a p-methylphenyl group, a p-tert-butylphenyl group and a p-adamantylphenyl group. Examples of the aralkyl group include a benzyl group, a phenethyl group, a phenylpropyl group, a trityl group, a naphthylmethyl group and a naphthylethyl group.

Examples of the C1-C36 aliphatic hydrocarbon group represented by Y include a methyl group, an ethyl group, a propyl group, an isopropyl group, a butyl group, an isobutyl group, a sec-butyl group, a tert-butyl group, a pentyl group, a neopentyl group, a 1-methylbutyl group, a 2-methylbutyl group, a 1,2-dimethylpropyl group, a 1-ethylpropyl group, a hexyl group, a 1-methylpentyl group, a heptyl group, an octyl group, a 2-ethylhexyl group, a nonyl group, a decyl group, an undecyl group and a dodecyl group, and a C1-C6 alkyl group is preferable. Examples of the C3-C36 saturated cyclic hydrocarbon group represented by $Y^1$ include the groups represented by the formulae (Y1) to (Y26):

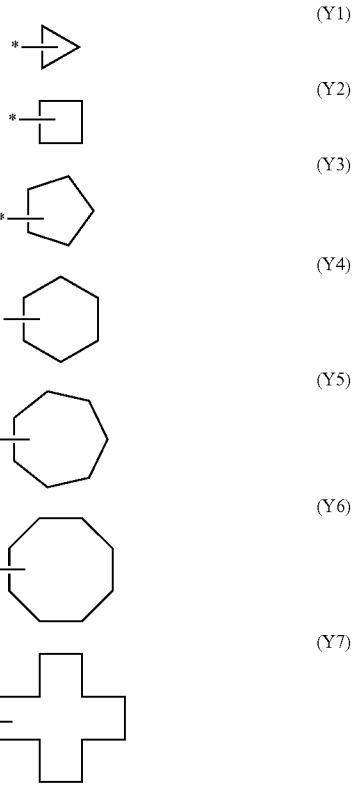

-continued
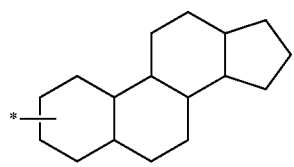 (Y8)
 (Y9)
 (Y10)
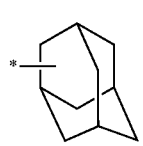 (Y11)
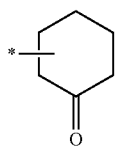 (Y12)
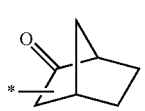 (Y13)
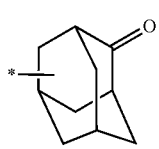 (Y14)
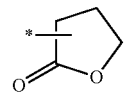 (Y15)
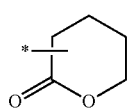 (Y16)
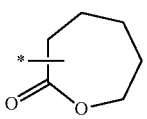 (Y17)
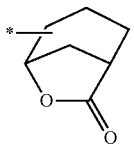 (Y18)
-continued
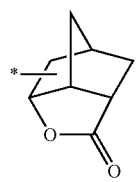 (Y19)
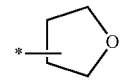 (Y20)
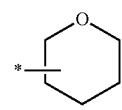 (Y21)
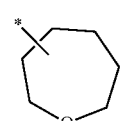 (Y22)
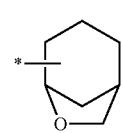 (Y23)
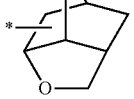 (Y24)
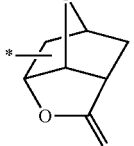 (Y25)
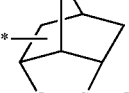 (Y26)
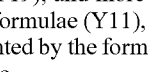
Among them, preferred are the groups represented by the formulae (Y1) to (Y19), and more preferred are the groups represented by the formulae (Y11), (Y14), (Y15) and (Y19). The groups represented by the formulae (Y11) and (Y14) are especially preferable.
Examples of $Y^1$ having one or more substituents include the followings:
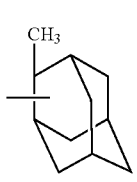 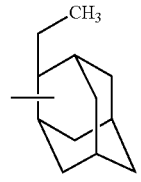 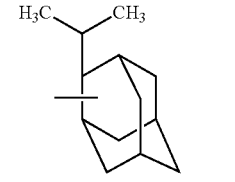

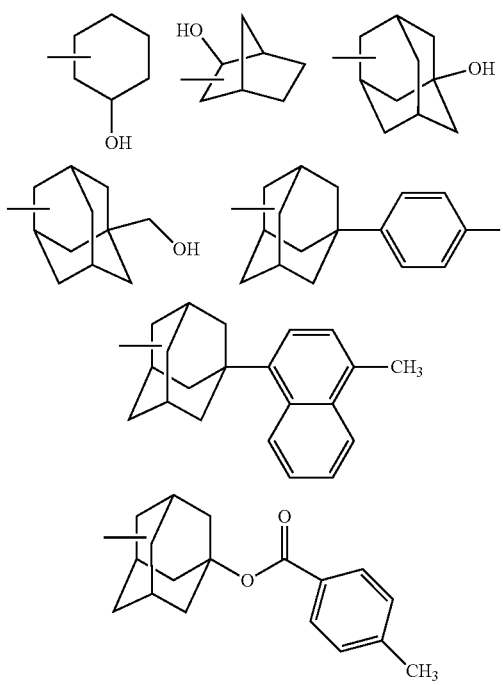

Y¹ is preferably an adamantyl group which can have one or more substituents, and is more preferably an adamantyl group or an oxoadamantyl group.

Preferable examples of the anion part of the acid generator other than SALT (I) include a salt represented by the formula (II) include the following anions represented by the formulae (IIa) to (IIi):

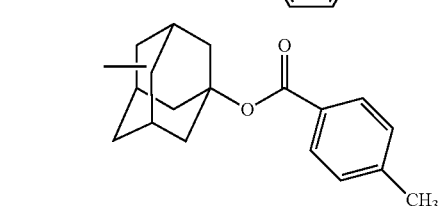
(IIa)

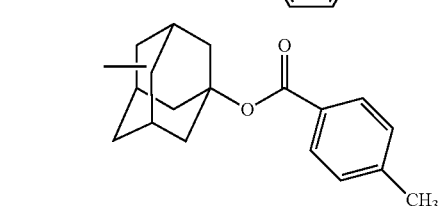
(IIb)

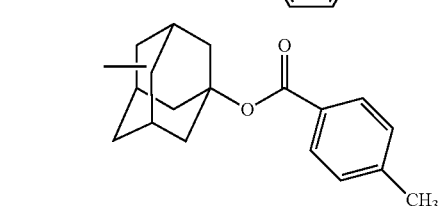
(IIc)

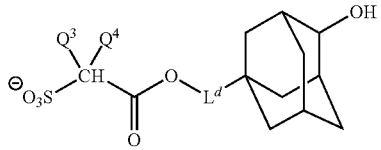
(IId)

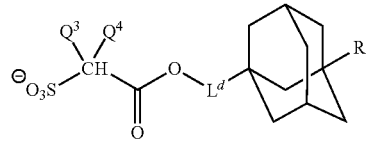
(IIe)

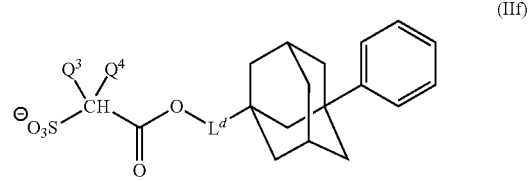
(IIf)

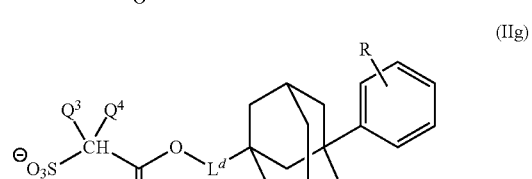
(IIg)

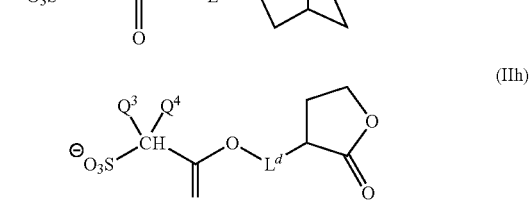
(IIh)

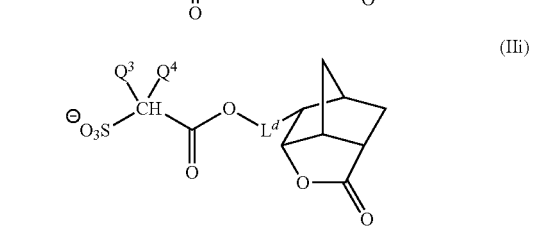
(IIi)

wherein $Q^3$, $Q^4$ and $L^d$ are the same as defined above, and R represents a C1-C4 aliphatic hydrocarbon group, and R is preferably a methyl group.

Examples of the anion part of the acid generator other than SALT (I) include the followings.

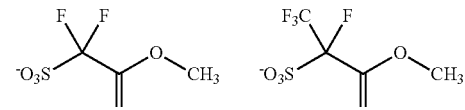

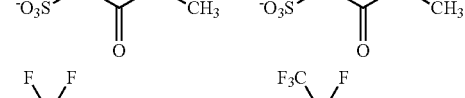

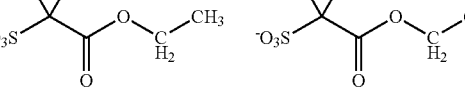

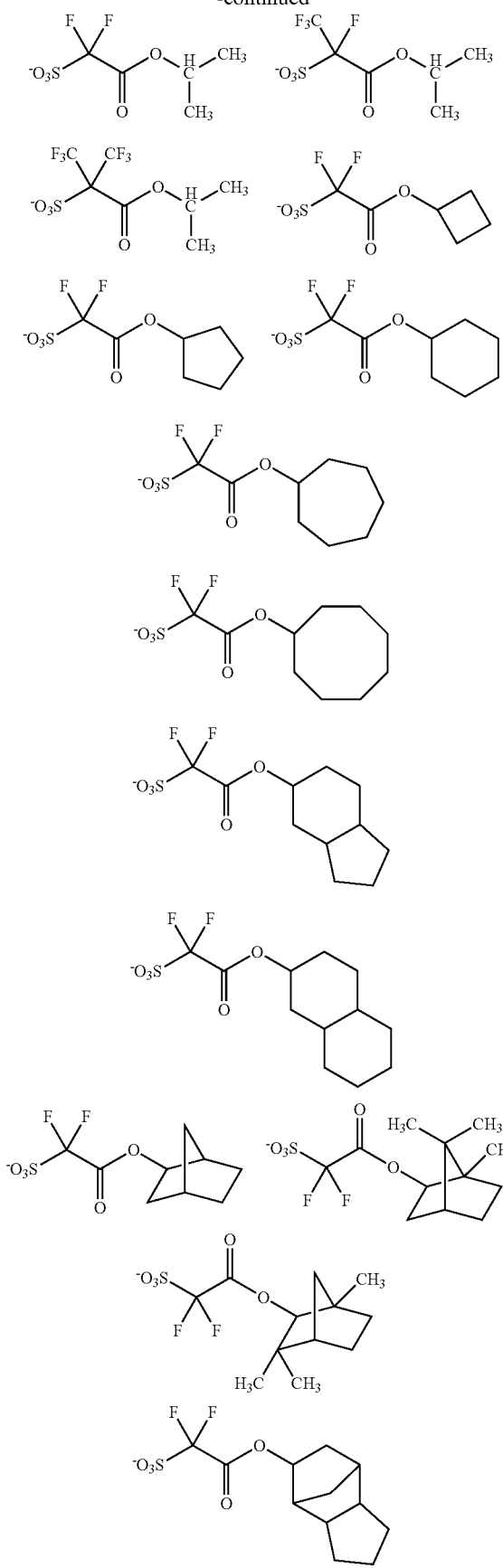

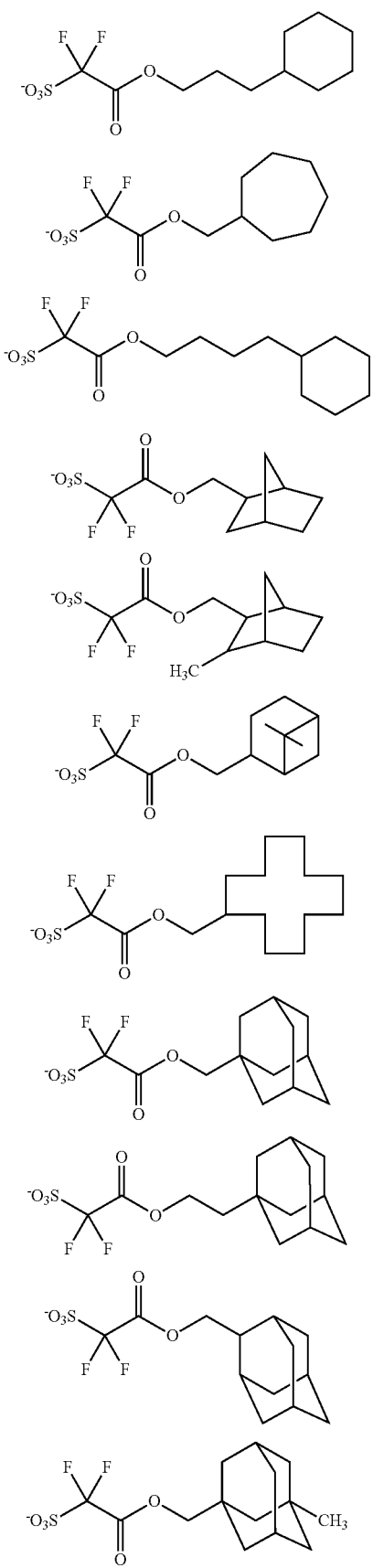
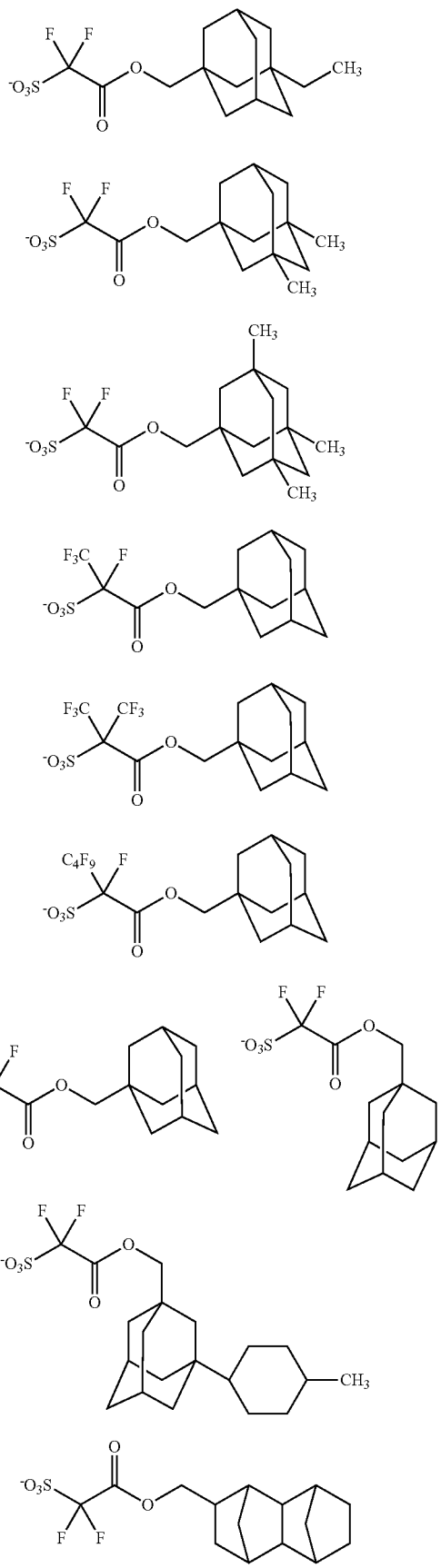

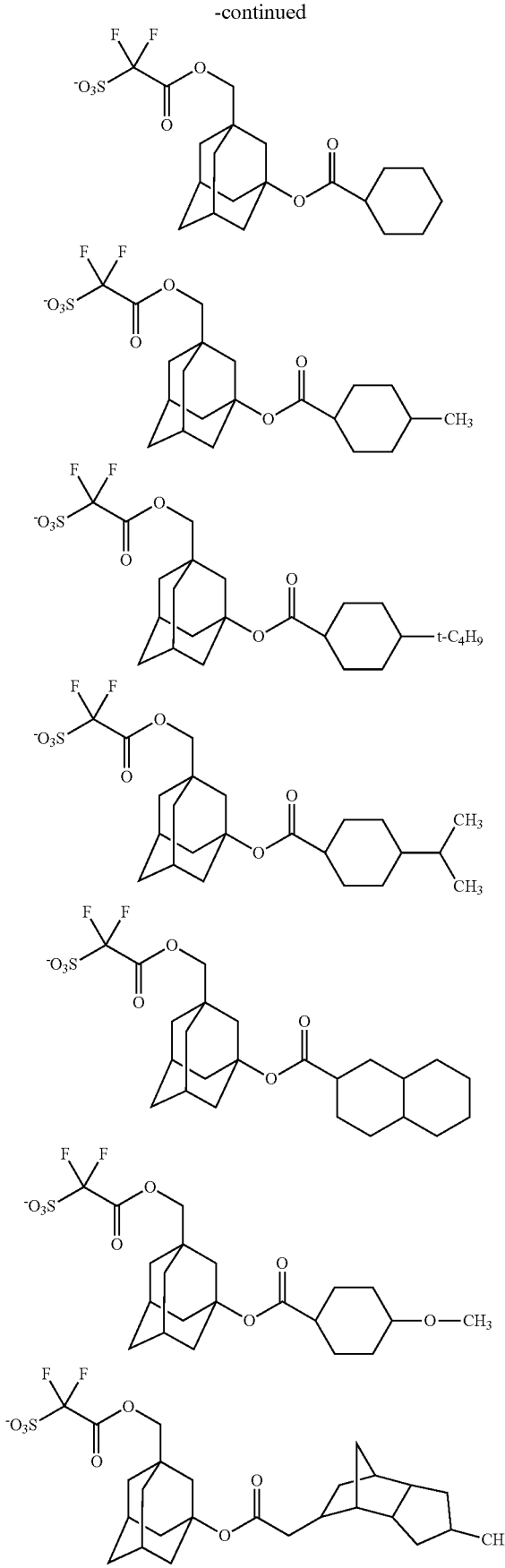
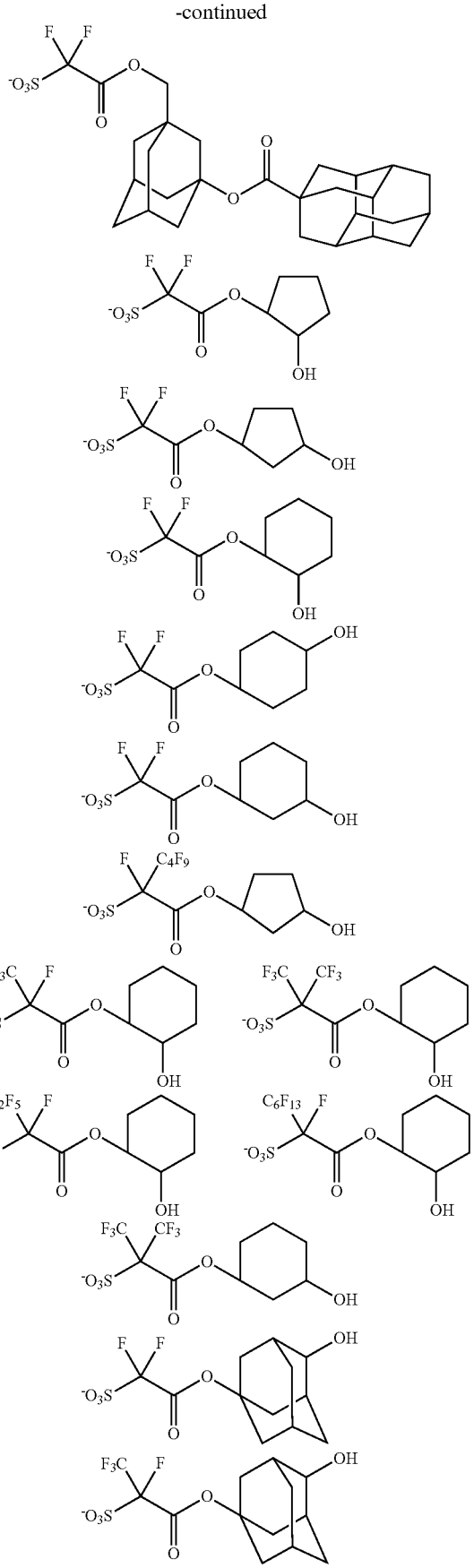

-continued
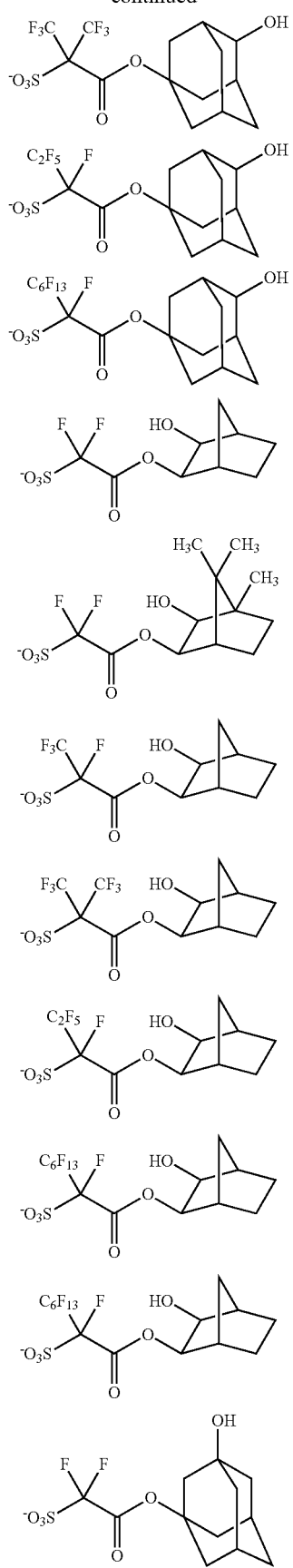
-continued
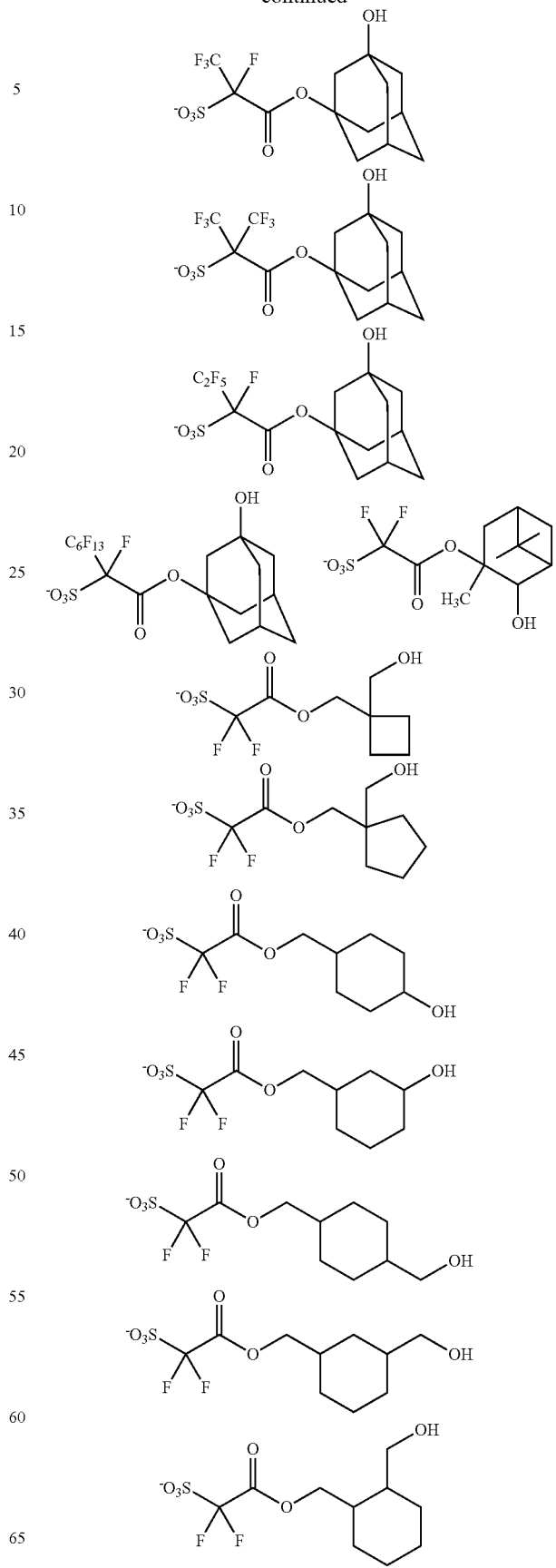

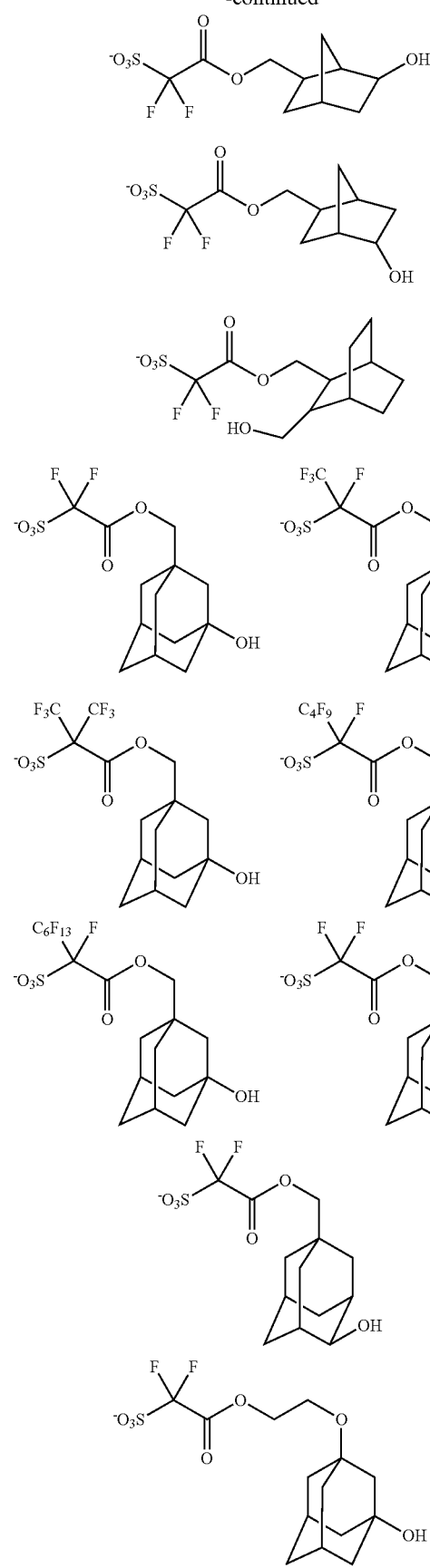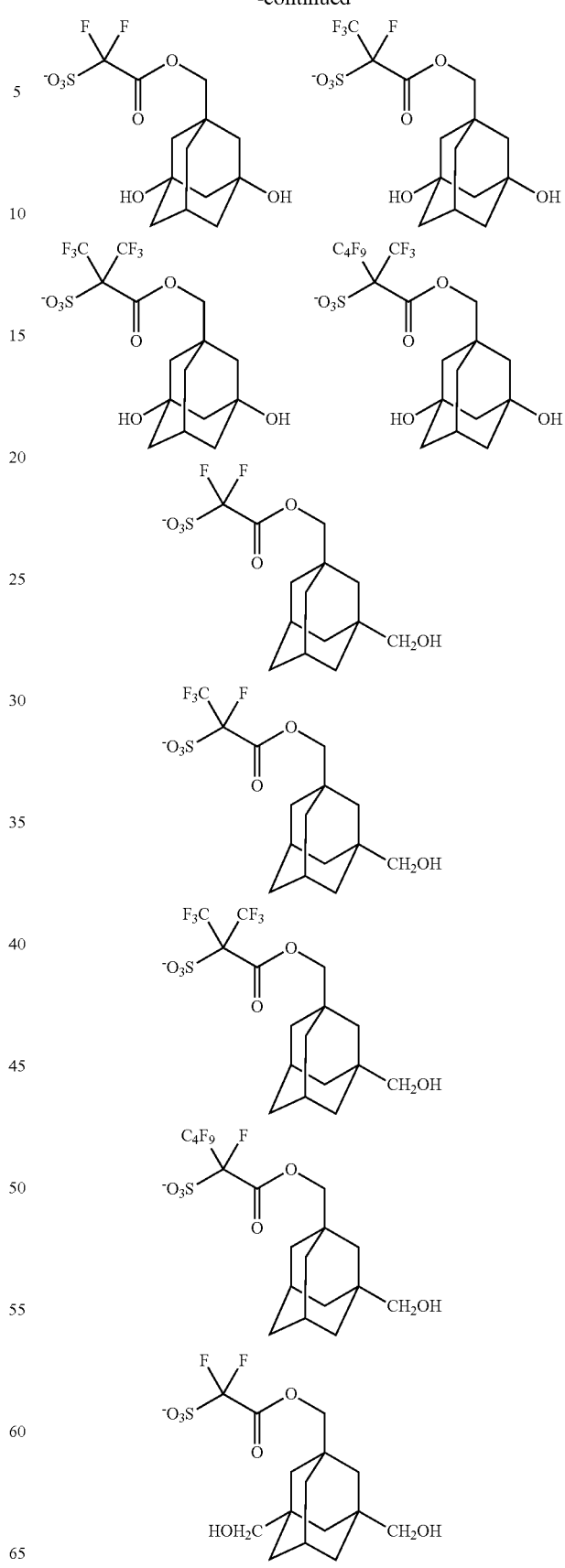

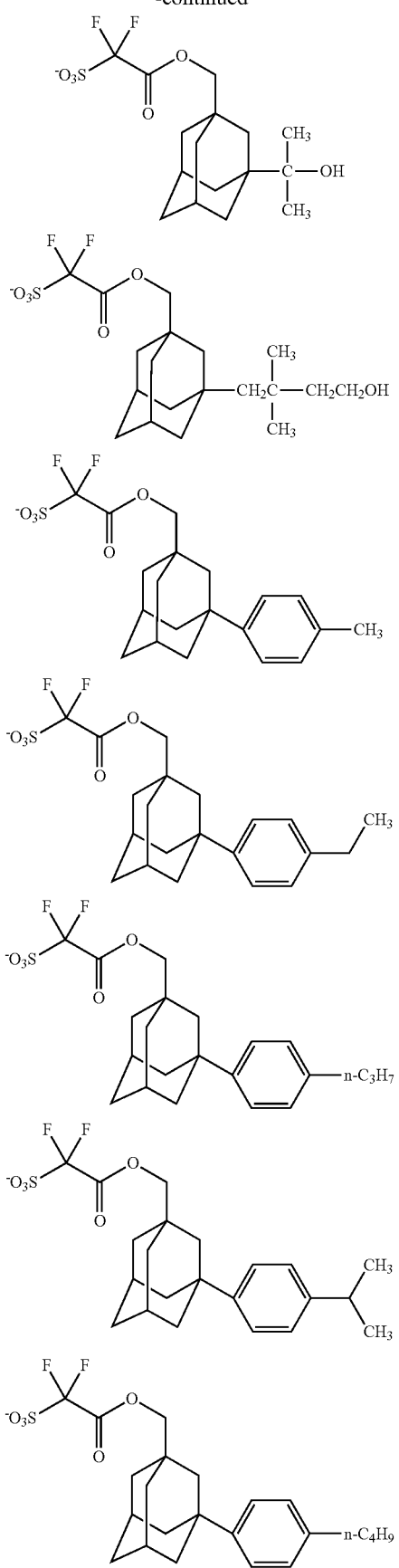
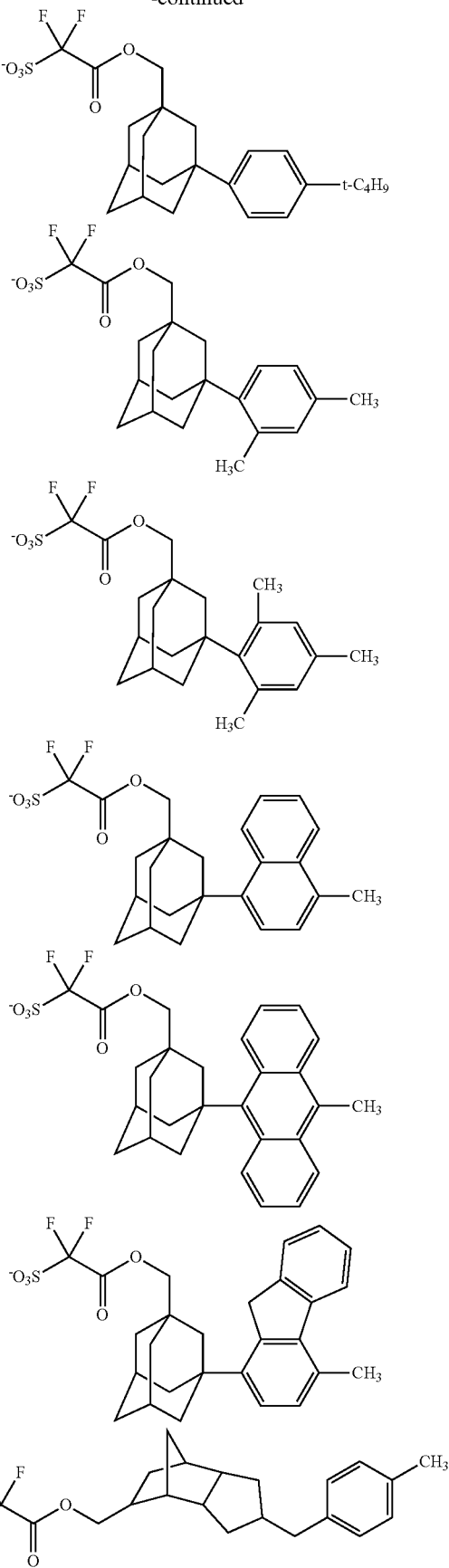

-continued
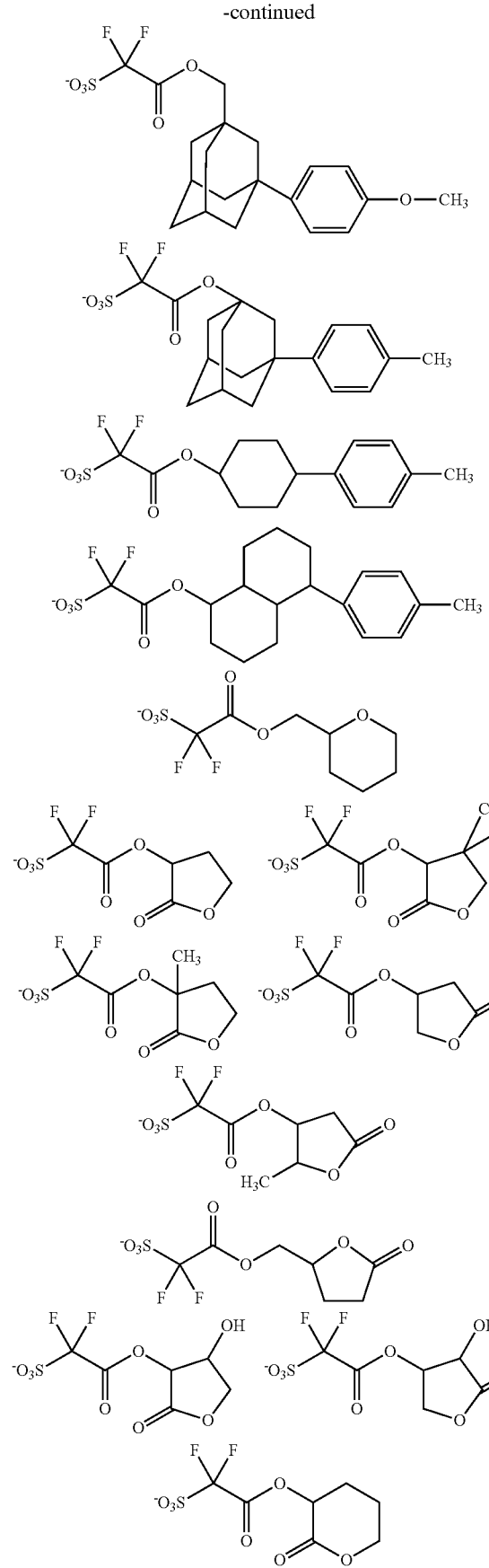
-continued
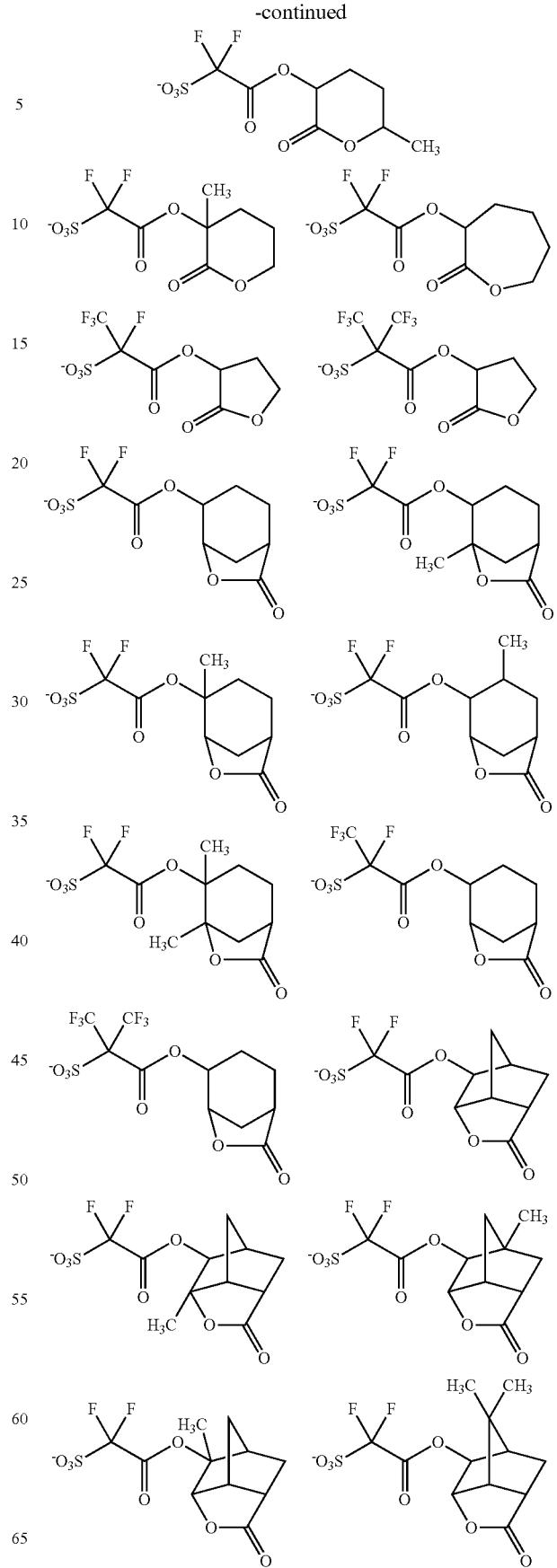

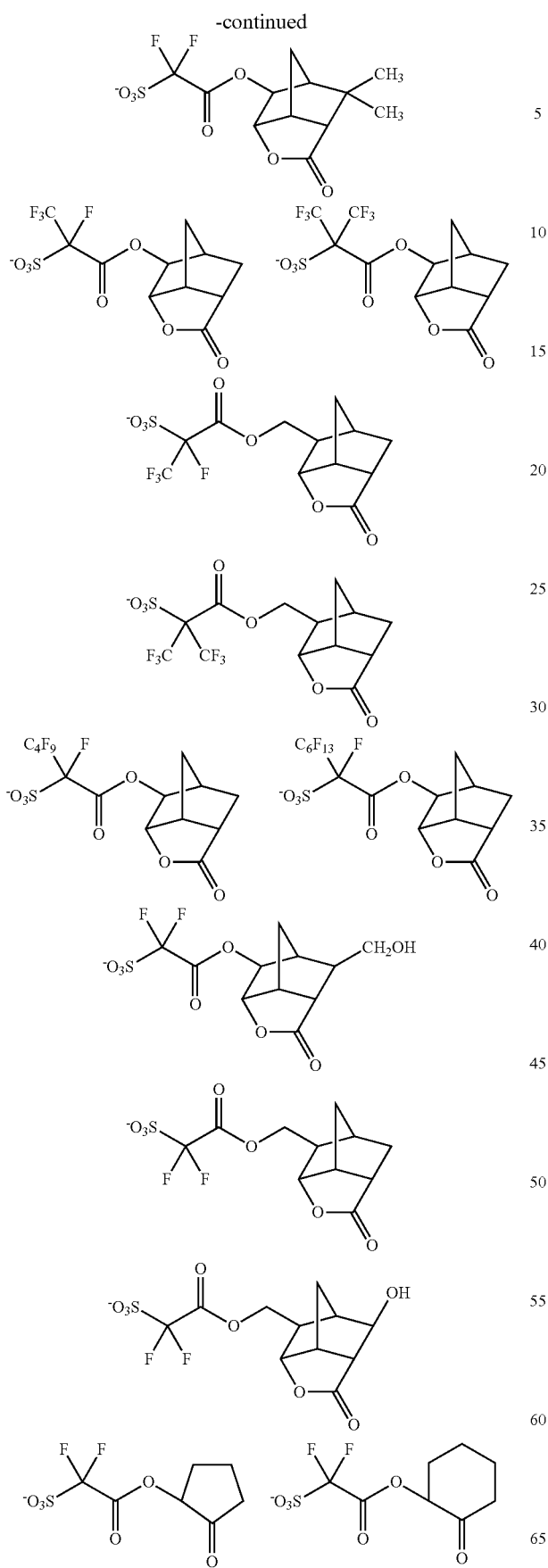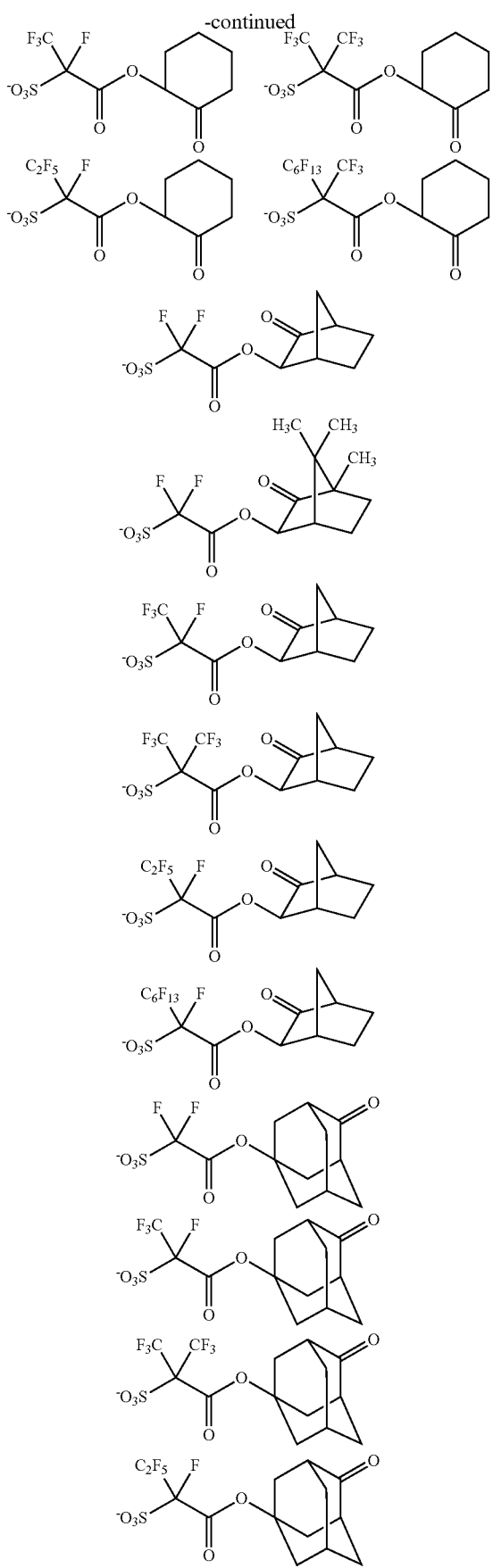

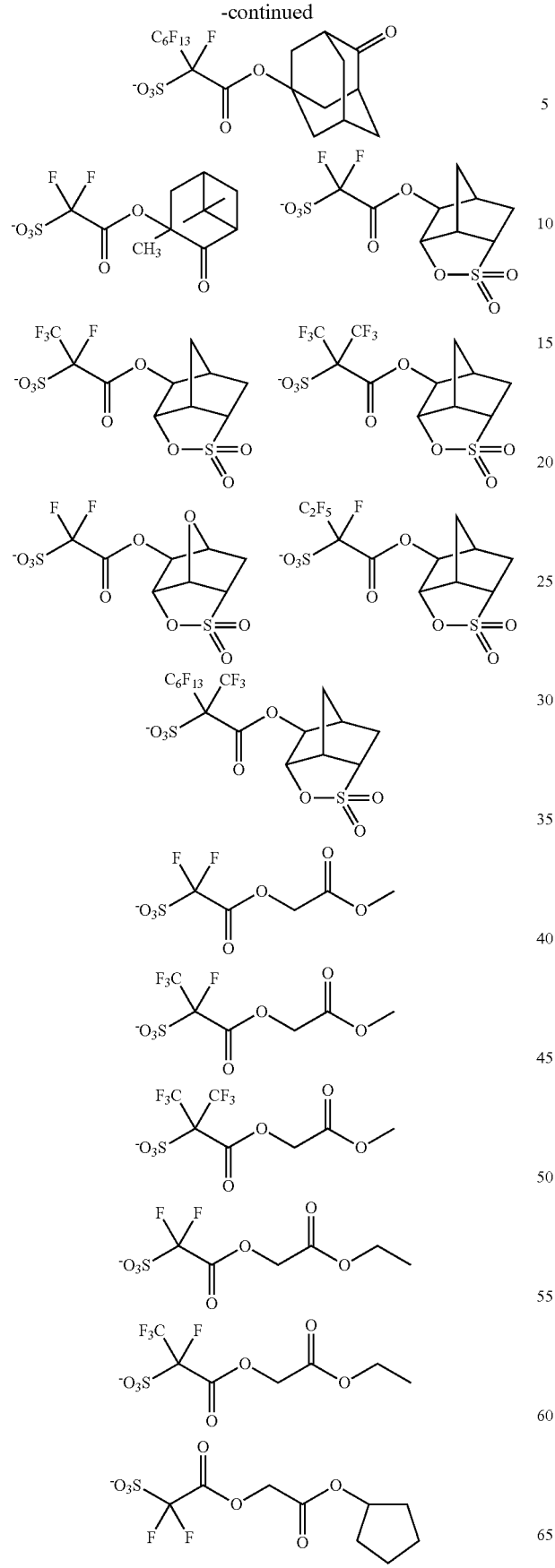
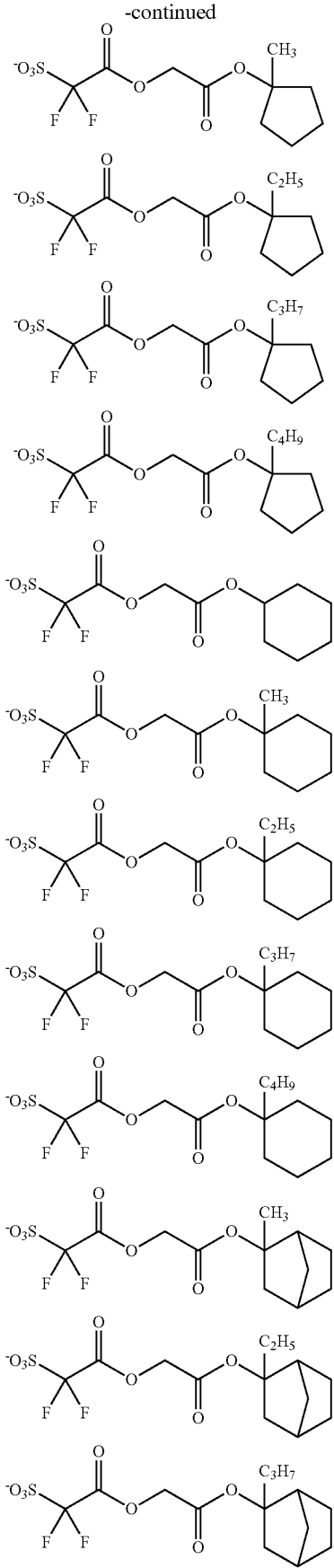

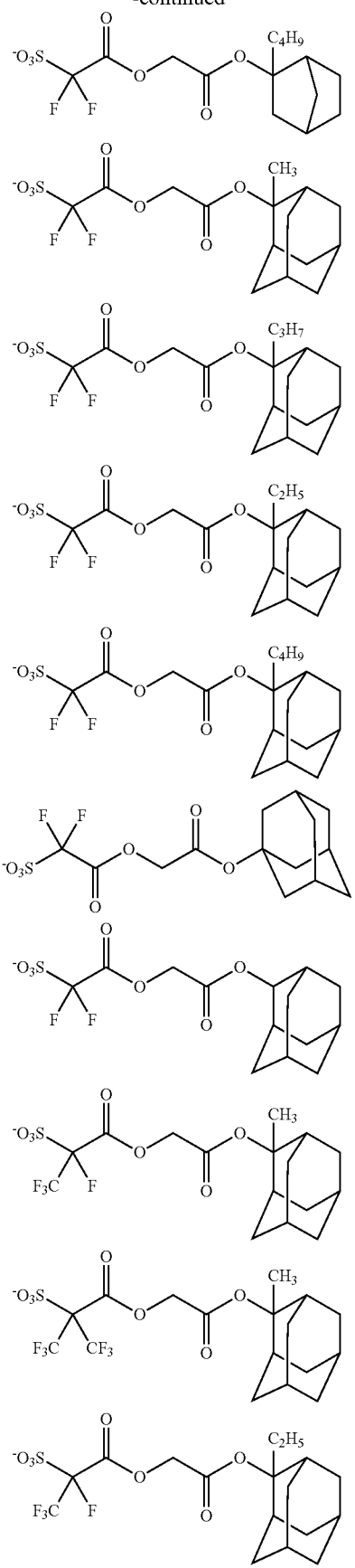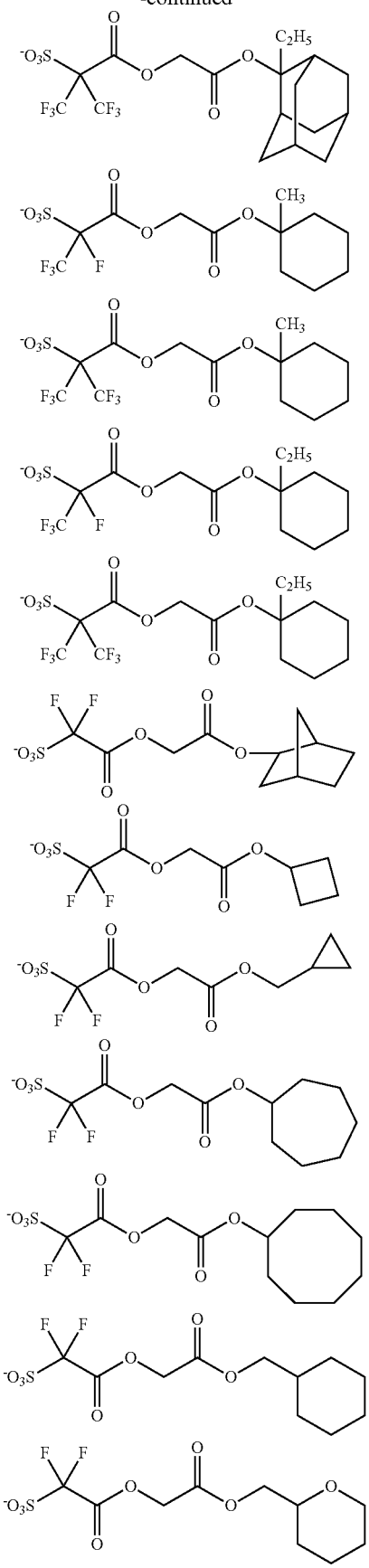

79
-continued
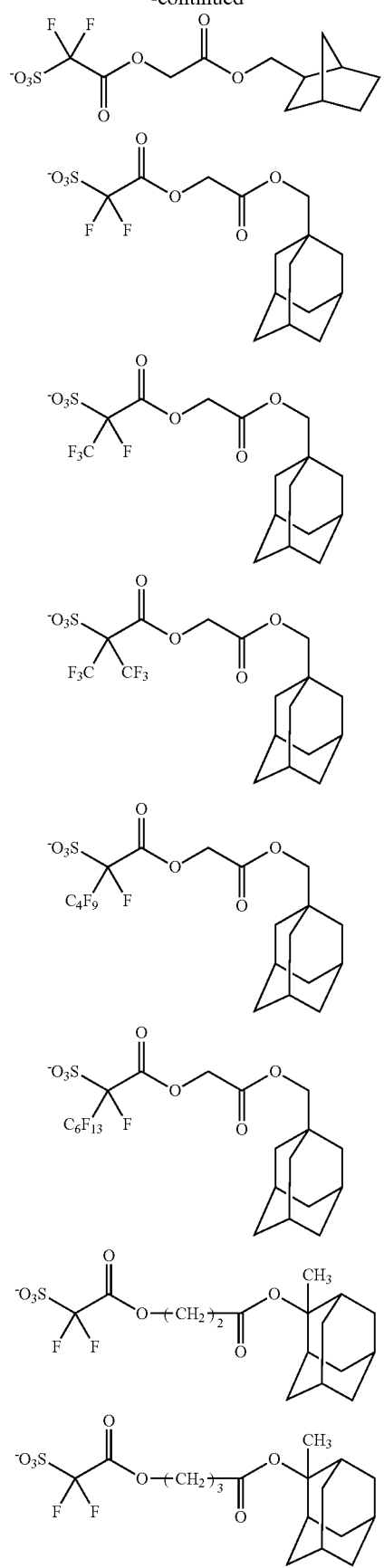
80
-continued
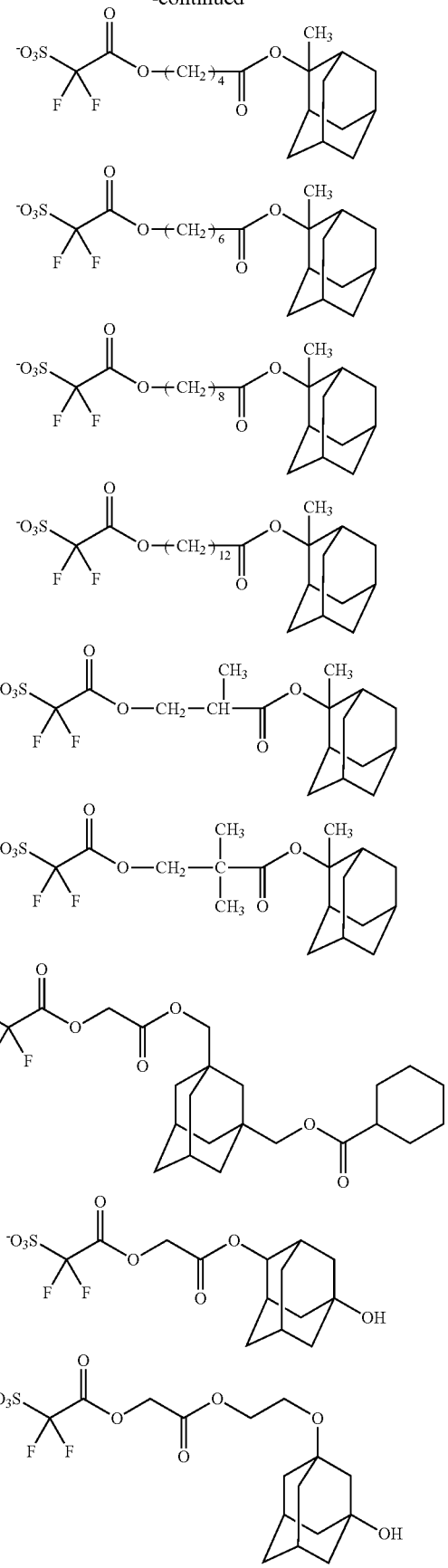

81
-continued
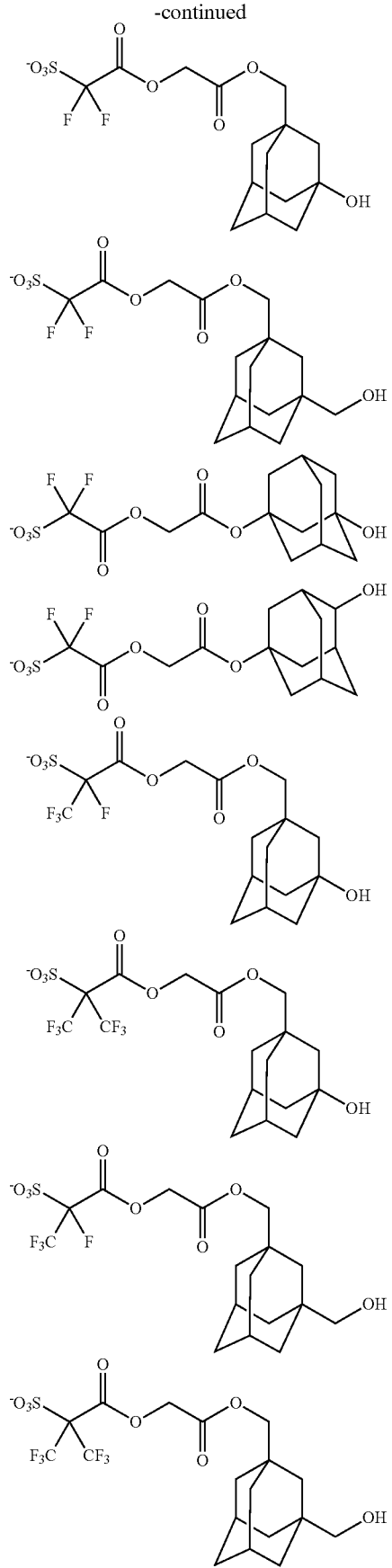
82
-continued
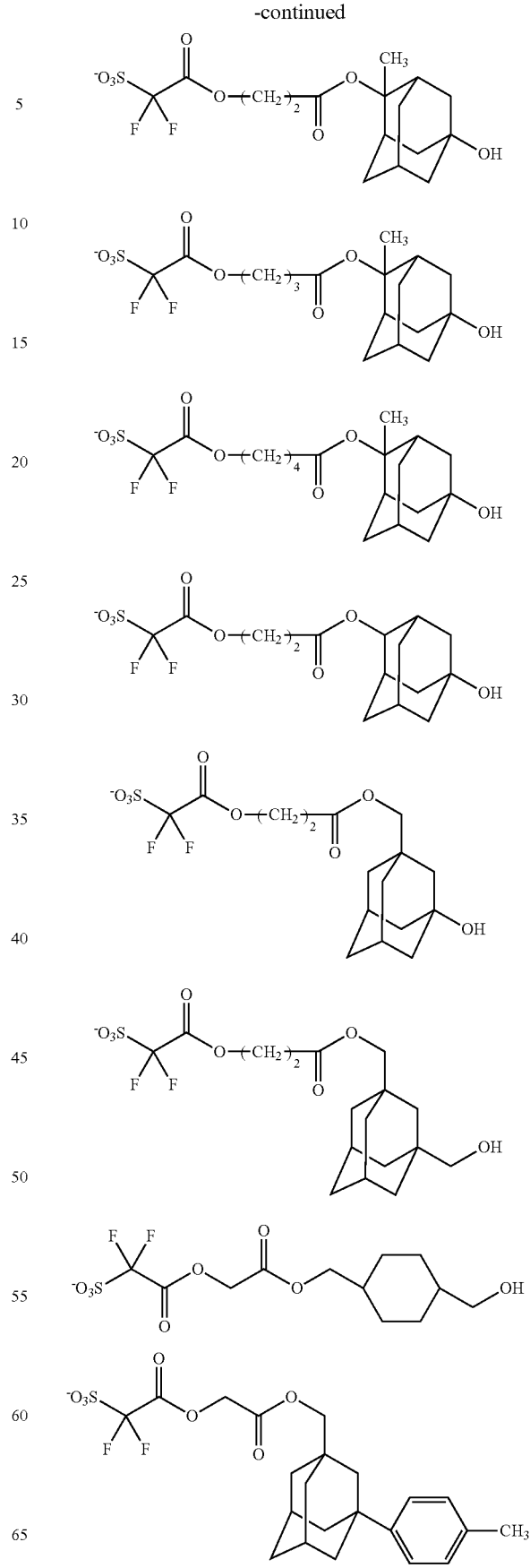

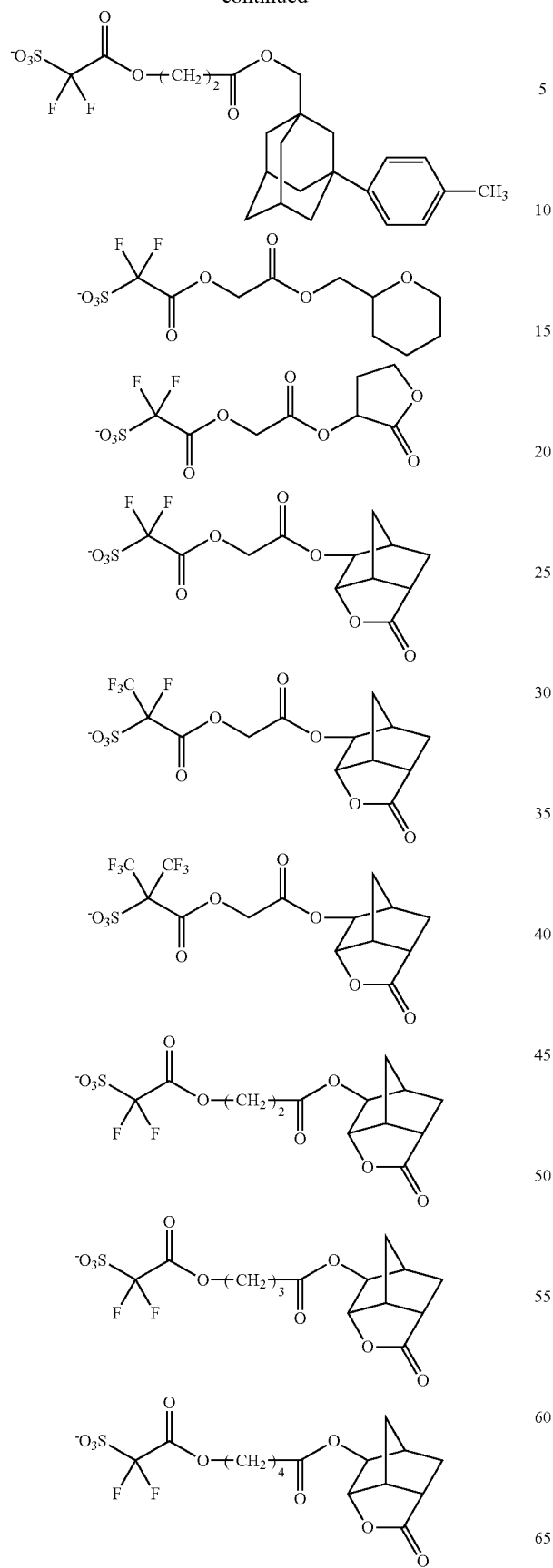
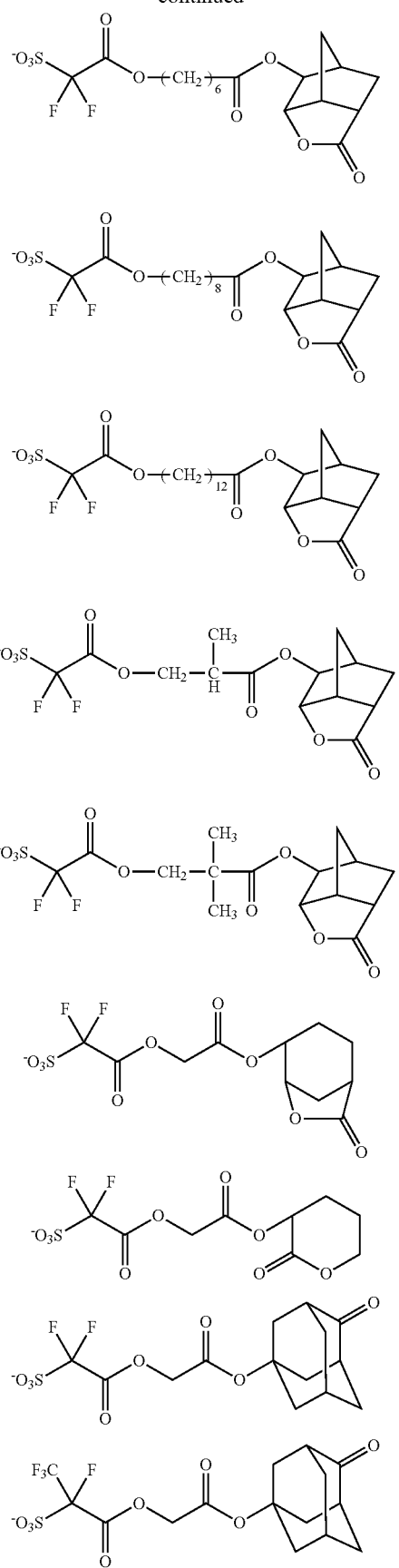

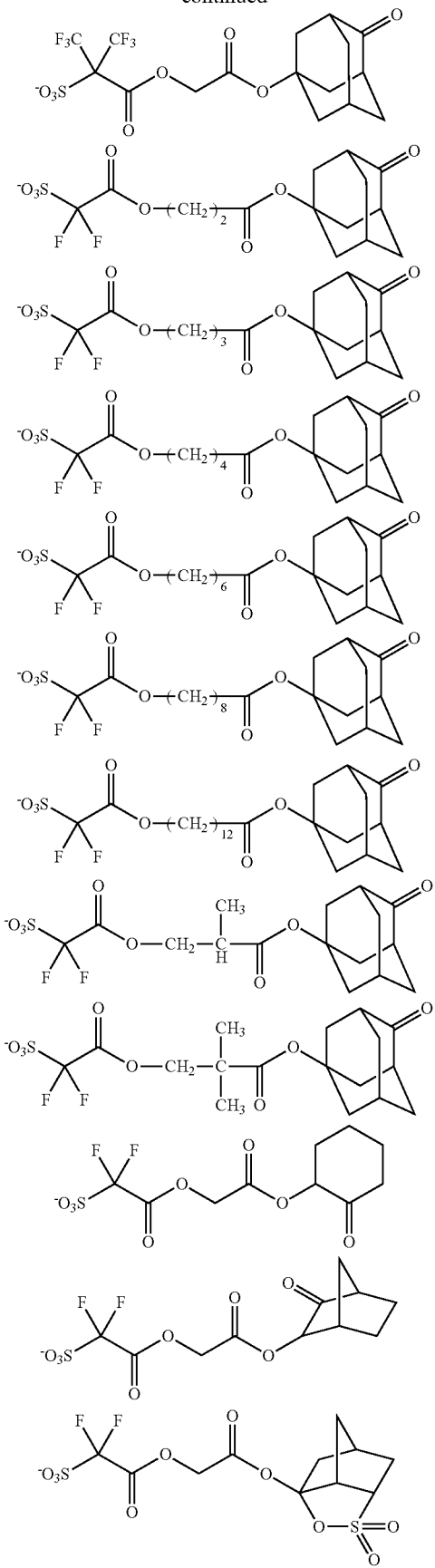
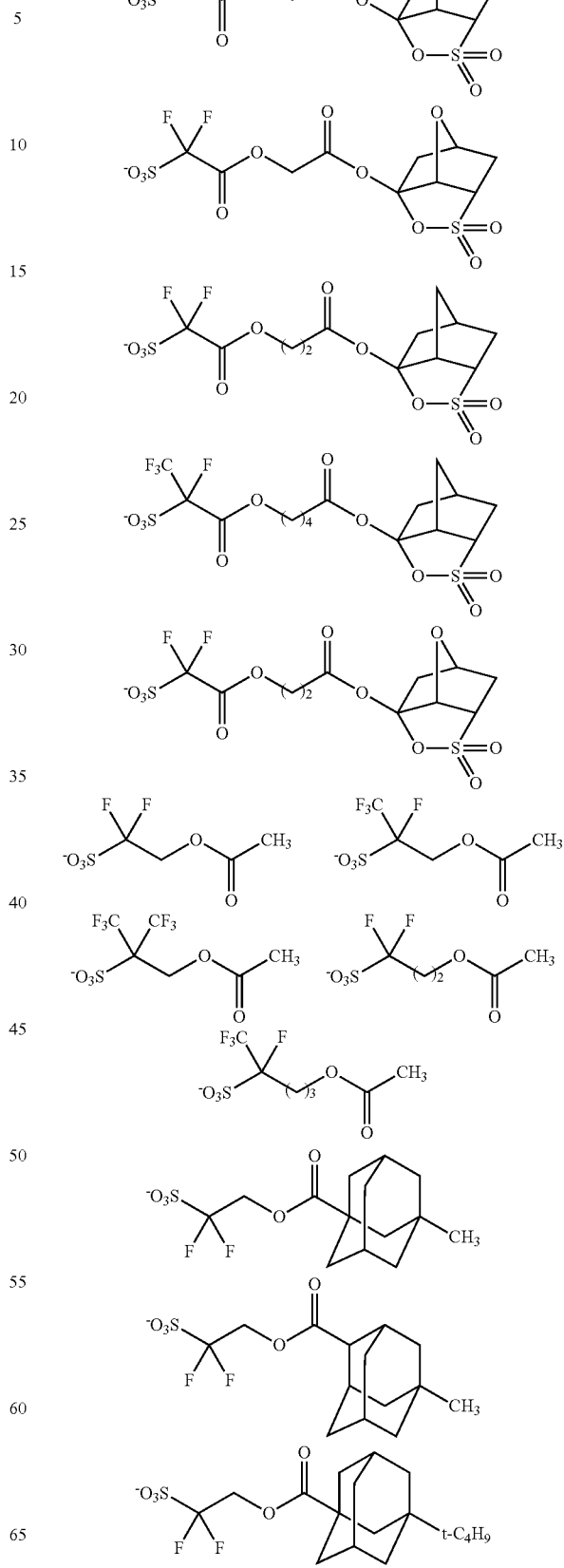

87
-continued
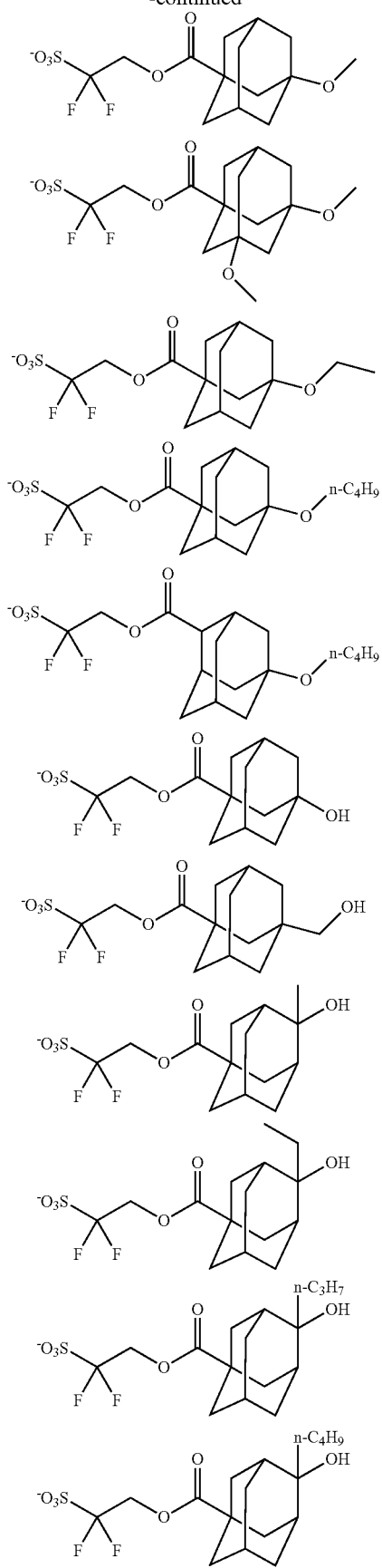
88
-continued
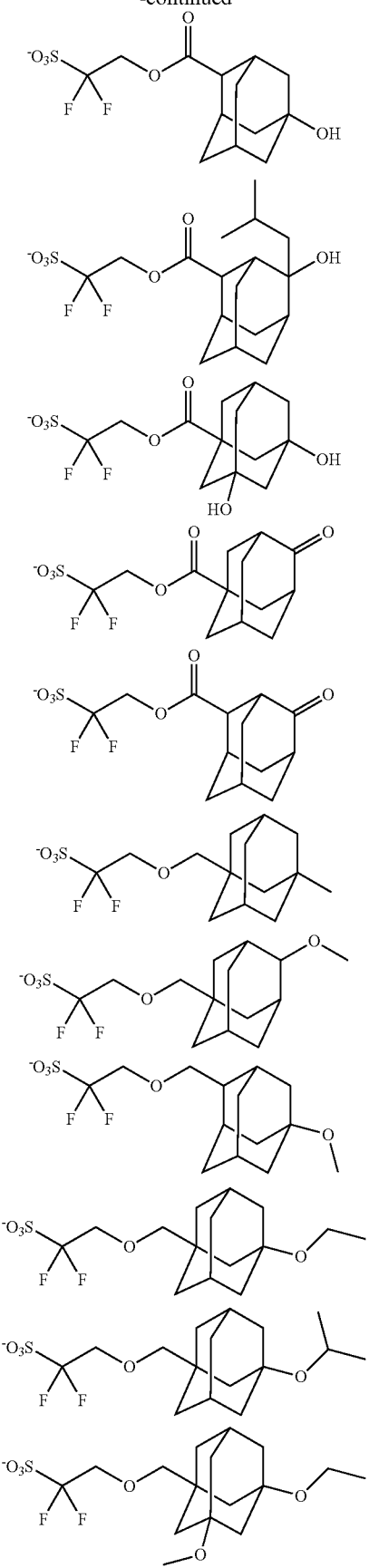

-continued
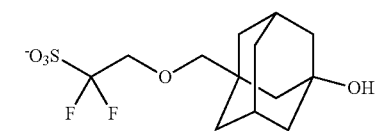
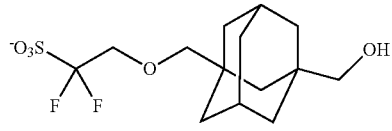
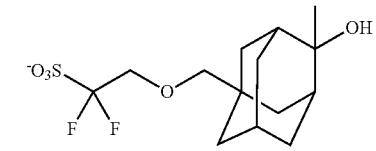
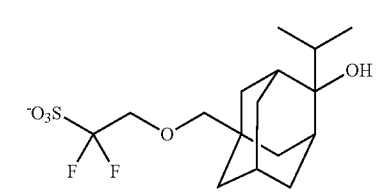
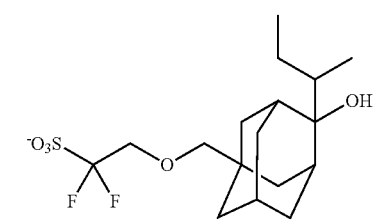
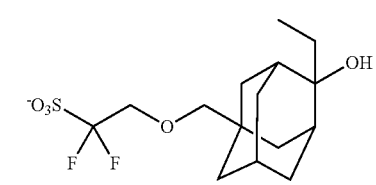
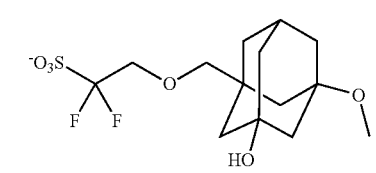
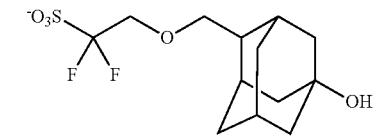
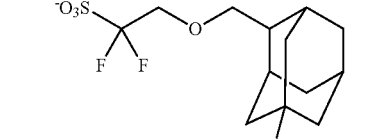
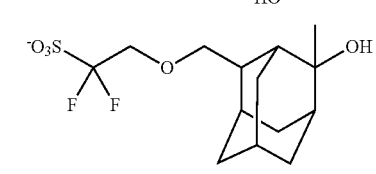
-continued
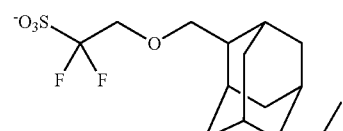
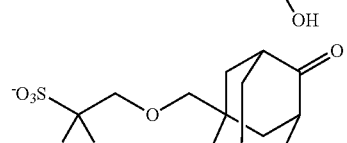
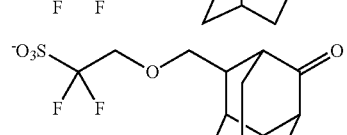
Among them, preferred are the following sulfonic anions.
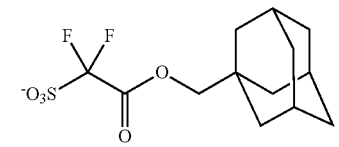
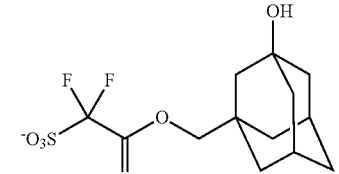
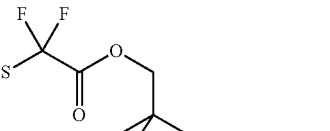
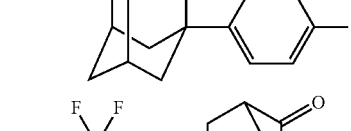
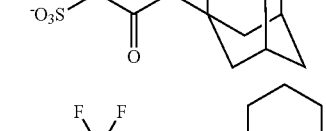
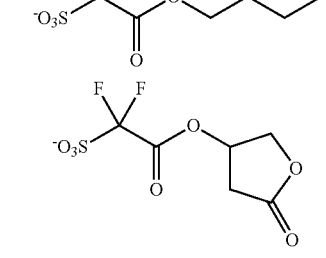

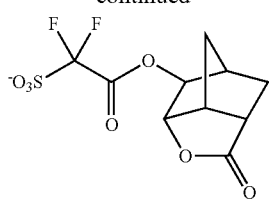

Examples of the organic counter ion represented by $Z^{2\oplus}$ in the salt represented by the formula (II) include an onium cation such as a sulfonium cation, an iodonium cation, an ammonium cation, a benzothiazolium cation and a phosphonium cation, and a sulfonium cation and an iodonium cation are preferable, and an arylsulfonium cation is more preferable.

Preferable examples of the cation part represented by $Z^{2\oplus}$ include the cations represented by the above-mentioned formulae (Z1) to (Z4), and the cation represented by the above-mentioned formula (Z1) is preferable and the cation represented by the above-mentioned formula (Z5) is more preferable, and a triphenylsulfonium cation is especially preferable.

Examples of the salt represented by the formula (II) include a salt wherein the anion part is any one of the above-mentioned anion part and the cation part is any one of the above-mentioned cation part. Preferable examples thereof include a salt formed by combining any one of anions represented by the formulae (IIa) to (IIi) with the cation represented by the formula (Z5), and a salt formed by combining any one of anions represented by the formulae (IIc) to (IIe) with the cation represented by the formula (Z3).

Preferred are the salts represented by the formulae (B1-1) to (B1-18), and more preferred are the salts represented by the formulae (B1-1), (B1-2), (B1-6), (B1-11), (B1-12), (B1-13) and (B1-14).

(B1-1)

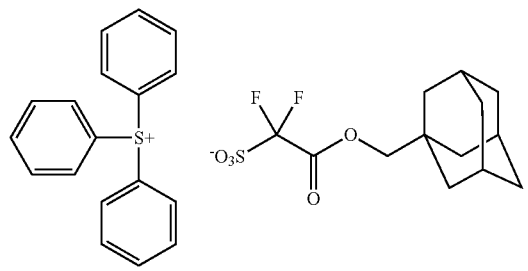

(B1-2)

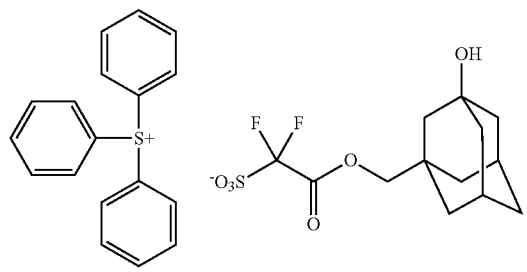

(B1-3)

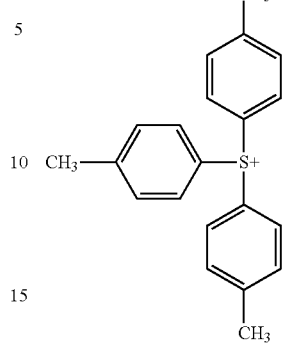

(B1-4)

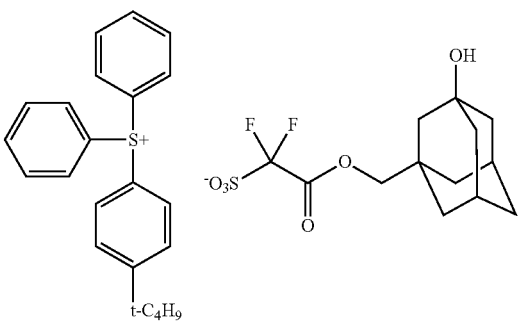

(B1-5)

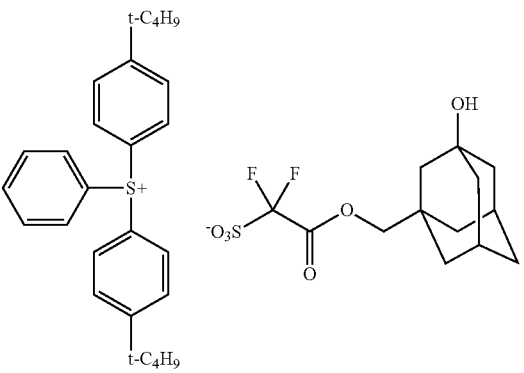

(B1-6)

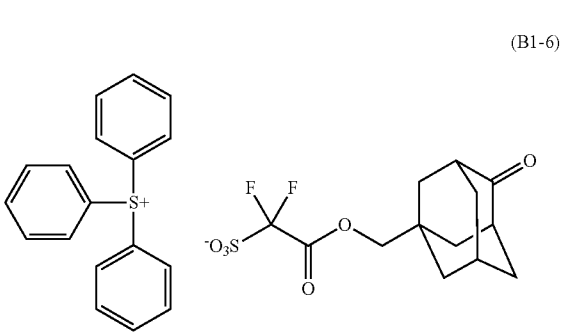

(B1-7)
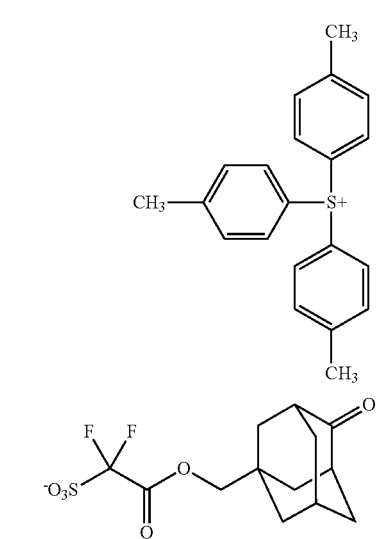
(B1-8)
(B1-9)
(B1-10)
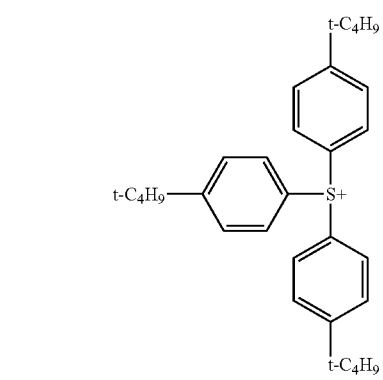
(B1-11)
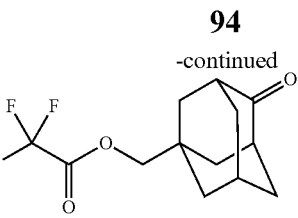
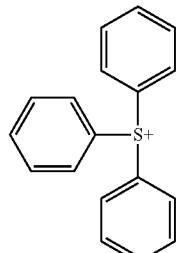
(B1-12)
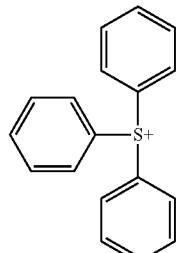
(B1-13)
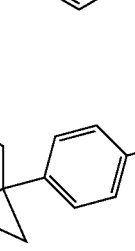
(B1-14)
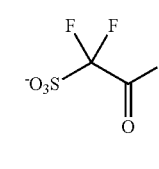
(B1-15)
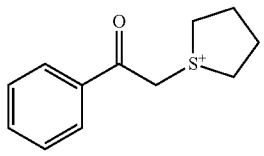

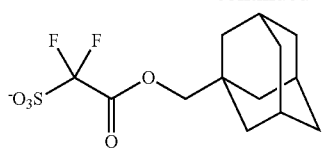

(B1-16)

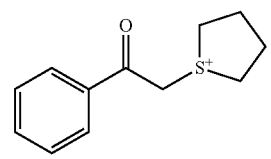

(B1-17)

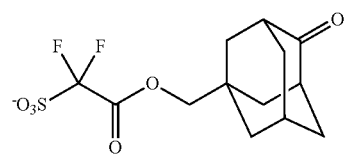

(B1-18)

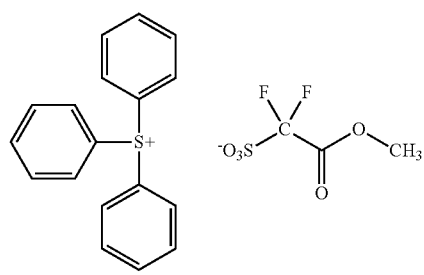

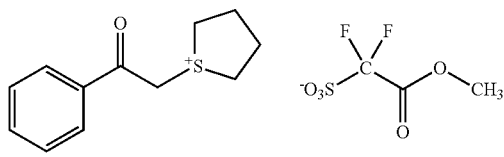

The salt represented by the formula (II) can be produced according to known methods in the art.

The amount of the acid generator other than SALT (I) in the photoresist composition of the present invention is usually 1 part by weight or more, and preferably 3 parts by weight or more per 100 parts by weight of the resin. The amount of the acid generator other than SALT (I) in the photoresist composition of the present invention is usually 30 parts by weight or less, and preferably 25 parts by weight or less per 100 parts by weight of the resin.

The resin will be illustrated below.

The resin has an acid-labile group and is insoluble or poorly soluble in an alkali aqueous solution but becomes soluble in an alkali aqueous solution by the action of an acid. The resin has a structural unit derived from a compound having an acid-labile group, and can be produced by polymerizing one or more compounds having an acid-labile group.

In this specification, "an acid-labile group" means a group capable of being eliminated by the action of an acid.

Examples of the acid-labile group include a group represented by the formula (1):

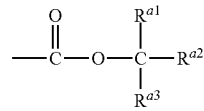

(1)

wherein $R^{a1}$, $R^{a2}$ and $R^{a3}$ independently each represent an aliphatic hydrocarbon group or a saturated cyclic hydrocarbon group, or $R^{a1}$ and $R^{a2}$ are bonded each other to form a ring together with a carbon atom to which $R^{a1}$ and $R^{a2}$ are bonded.

Examples of the aliphatic hydrocarbon group include a C1-C8 alkyl group. Specific examples of the C1-C8 alkyl group include a methyl group, an ethyl group, a propyl group, an isopropyl group, a butyl group, a pentyl group, a hexyl group, a heptyl group and an octyl group. The saturated cyclic hydrocarbon group may be monocyclic or polycyclic, and examples thereof include a monocyclic alicyclic hydrocarbon group such as a C3-C20 cycloalkyl group (e.g. a cyclopentyl group, a cyclohexyl group, a methylcyclohexyl group, a dimethylcyclohexyl group, a cycloheptyl group and a cyclooctyl group) and a polycyclic alicyclic hydrocarbon group such as a decahydronaphthyl group, an adamantyl group, a norbornyl group, a methylnorbornyl group, and the followings:

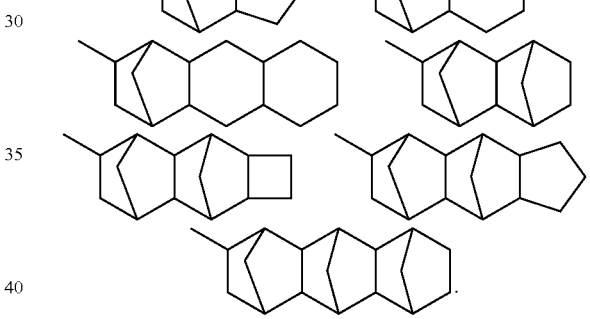

The saturated cyclic hydrocarbon group preferably has 3 to 20 carbon atoms.

Examples of the ring formed by bonding $R^{a1}$ and $R^{a2}$ each other include the following groups and the ring preferably has 3 to 20 carbon atoms, and the more preferably has 3 to 12 carbon atoms.

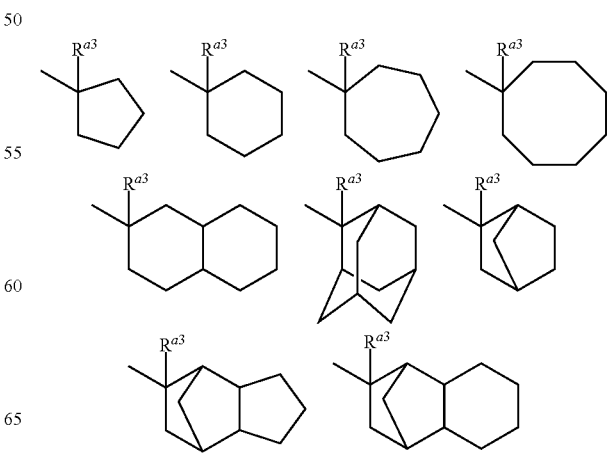

-continued

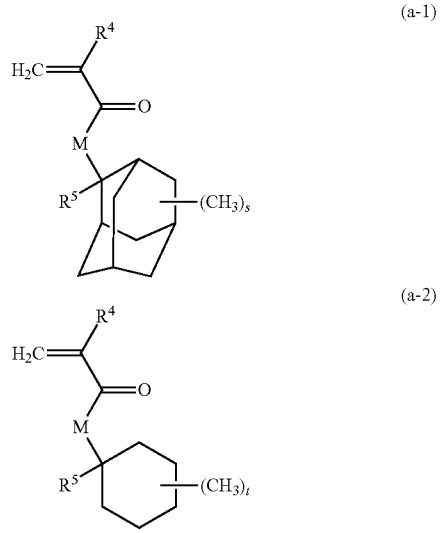

wherein $R^{a3}$ is the same as defined above.

The group represented by the formula (1) wherein $R^{a1}$, $R^{a2}$ and $R^{a3}$ independently each represent a C1-C8 alkyl group such as a tert-butyl group, the group represented by the formula (1) wherein $R^{a1}$ and $R^{a2}$ are bonded each other to form an adamantyl ring and $R^{a3}$ is a C1-C8 alkyl group such as a 2-alkyl-2-adamantyl group, and the group represented by the formula (1) wherein $R^{a1}$ and $R^{a2}$ are C1-C8 alkyl groups and $R^{a3}$ is an adamantyl group such as a 1-(1-adamantyl)-1-alkylalkoxycarbonyl group are preferable.

The compound having an acid-labile group is preferably an acrylate monomer having an acid-labile group in its side chain or a methacryalte monomer having an acid-labile group in its side chain.

Preferable examples of the compound having an acid-labile group include monomers represented by the formulae (a1-1) and (a1-2):

(a1-1)

[structure]

(a1-2)

[structure]

wherein $R^4$ represents a hydrogen atom or a methyl group, $R^5$ represents a C1-C8 aliphatic hydrocarbon group or a C3-C10 saturated hydrocarbon group, M represents *—O— or *—O—$(CH_2)_k$—CO—O— in which * represents a binding position to —CO—, and k represents an integer of 1 to 7, s represents an integer of 0 to 14 and t represents an integer of 0 to 10.

The aliphatic hydrocarbon group preferably has 1 to 6 carbon atoms, and the saturated cyclic hydrocarbon group preferably has 3 to 8 carbon atoms and more preferably 3 to 6 carbon atoms.

Examples of the aliphatic hydrocarbon group include a C1-C8 alkyl group such as a methyl group, an ethyl group, a propyl group, an isopropyl group, a butyl group, a tert-butyl group, a 2,2-dimethylethyl group, a 1-methylpropyl group, a 2,2-dimethylpropyl group, a 1-ethylpropyl group, a 1-methylbutyl group, a 2-methylbutyl group, a 3-methylbutyl group, a 1-propylbutyl group, a pentyl group, a 1-methylpentyl group, a hexyl group, a 1,4-dimethylhexyl group, a heptyl group, a 1-methylheptyl group and an octyl group. Examples of the saturated cyclic hydrocarbon group include a cyclohexyl group, a methylcyclohexyl group, a dimethylcyclohexyl group, a cycloheptyl group, a methylcycloheptyl group, a norbornyl group and a methylnorbornyl group. $R^{a4}$ is preferably a methyl group, an ethyl group or an isopropyl group, and $R^{a5}$ is preferably a methyl group, an ethyl group or an isopropyl group.

M is preferably *—O— or *—O—$(CH_2)_f$—CO—O— in which * represents a binding position to —CO—, and f represents an integer of 1 to 4, and is more preferably *—O— or *—O—$CH_2$—CO—O—, and is especially preferably *—O—.

In the formula (a-1), s is preferably an integer of 0 to 3, and is more preferably 0 or 1. In the formula (a-2), t is preferably an integer of 0 to 3, and is more preferably 0 or 1.

Particularly when the photoresist composition contains a resin derived from a monomer having a bulky structure such as a saturated cyclic hydrocarbon group, the photoresist composition having an excellent resolution tends to be obtained.

Examples of the monomer represented by the formula (a-1) include the followings.

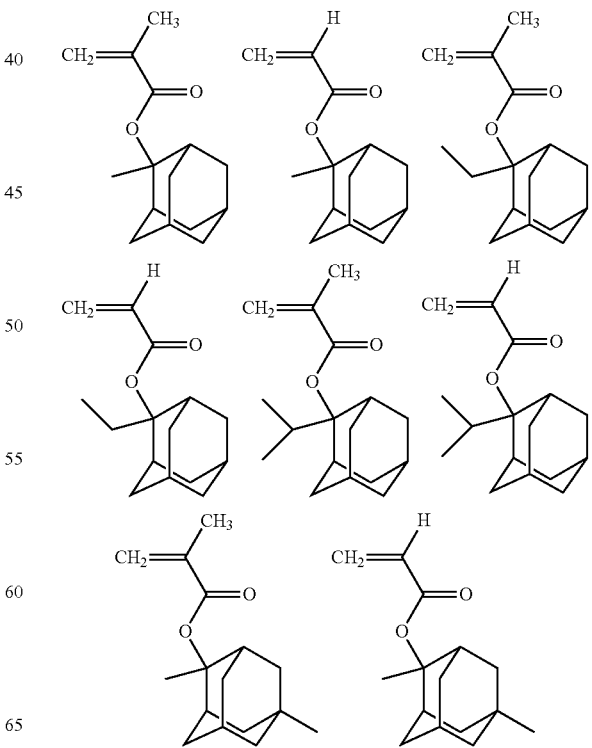

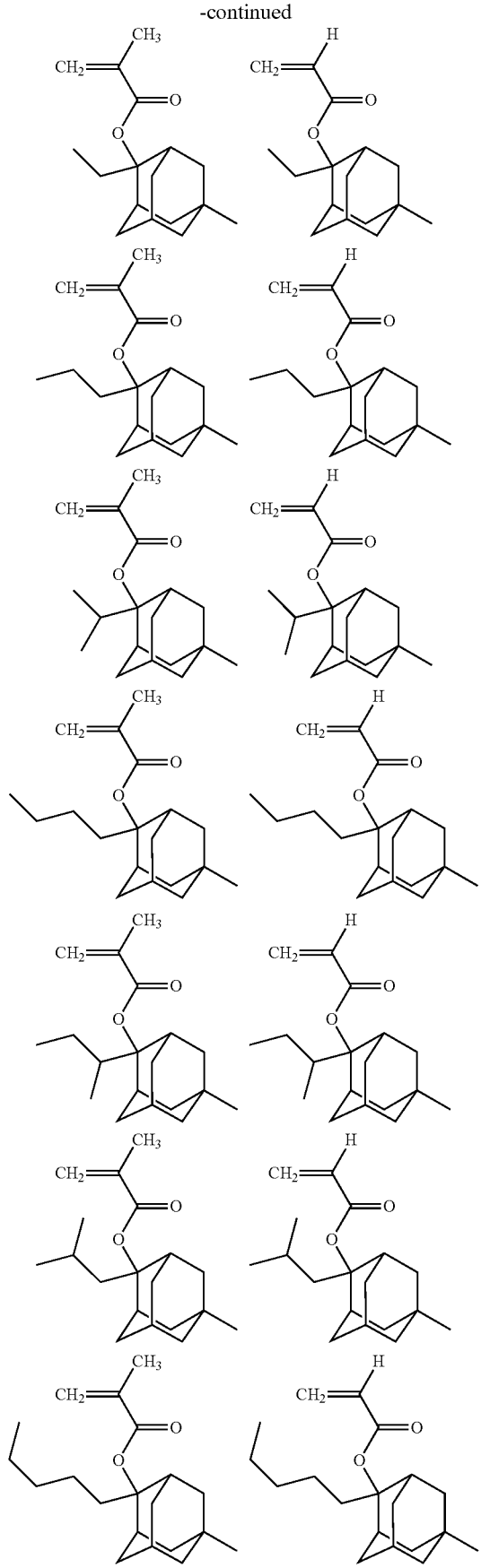
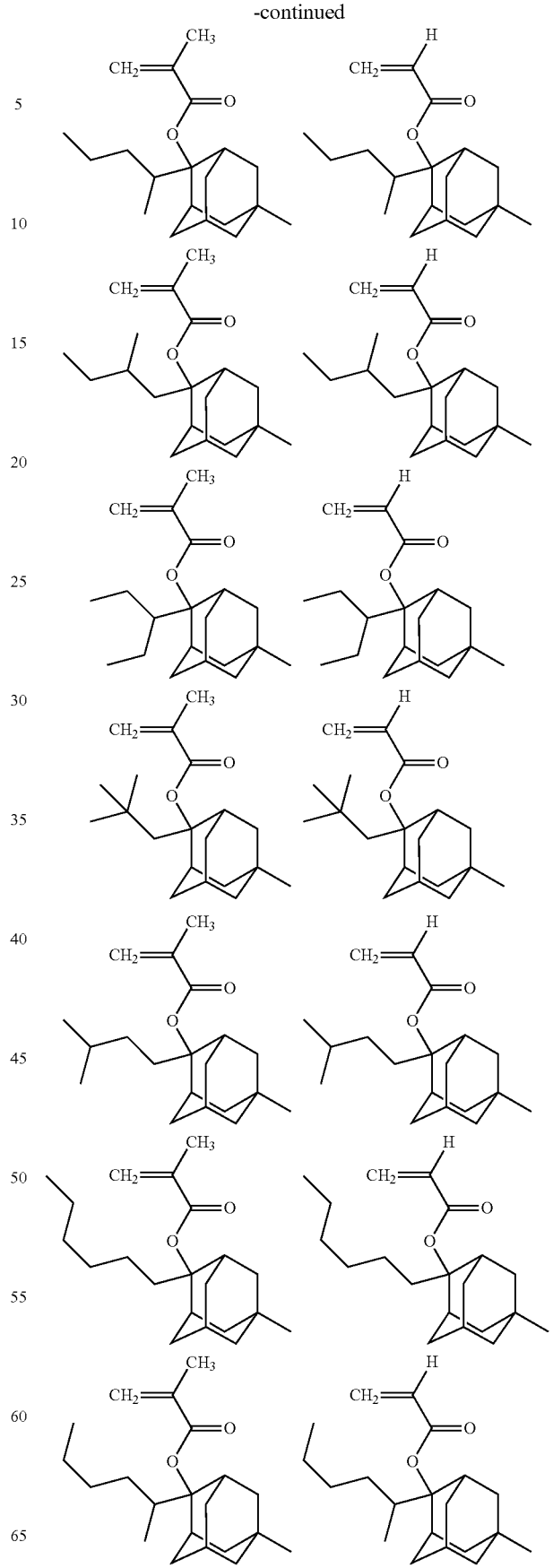

101
-continued
102
-continued
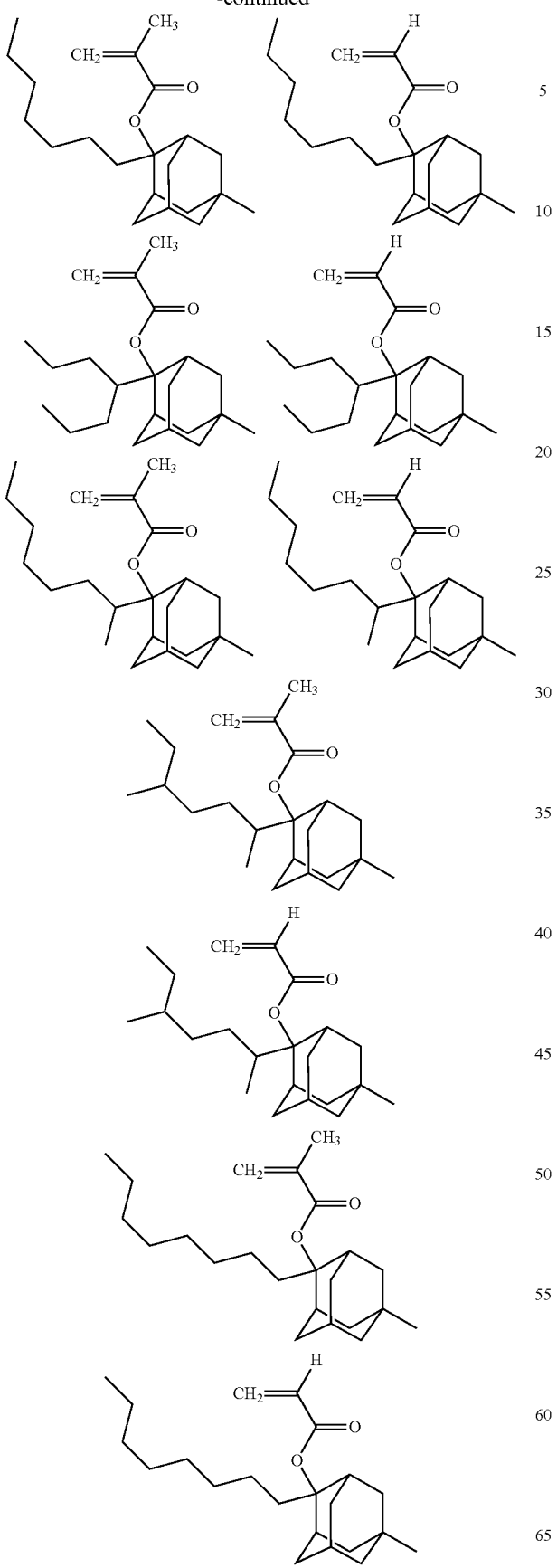
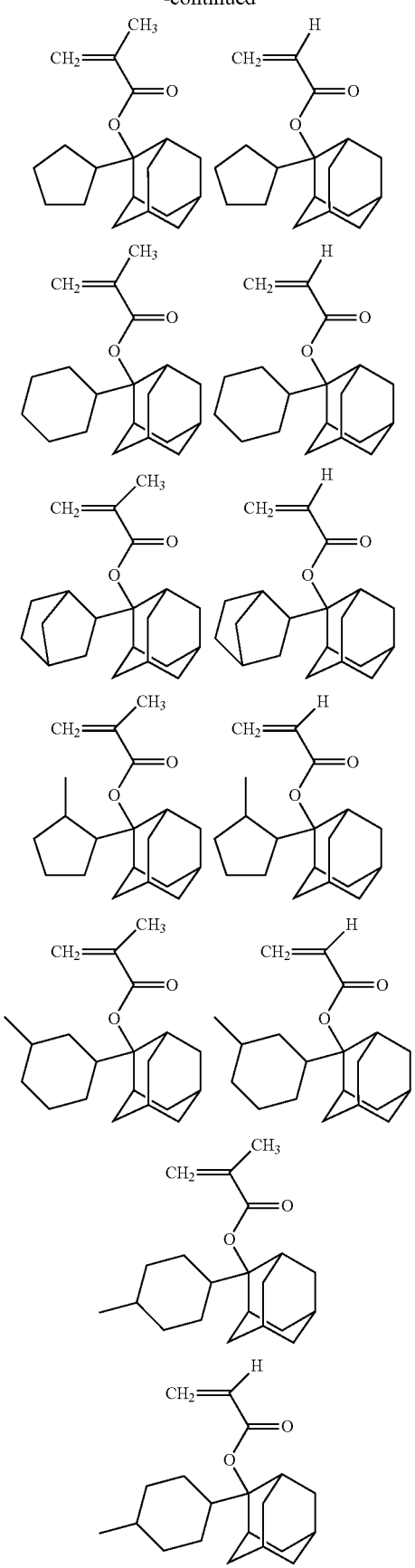

103
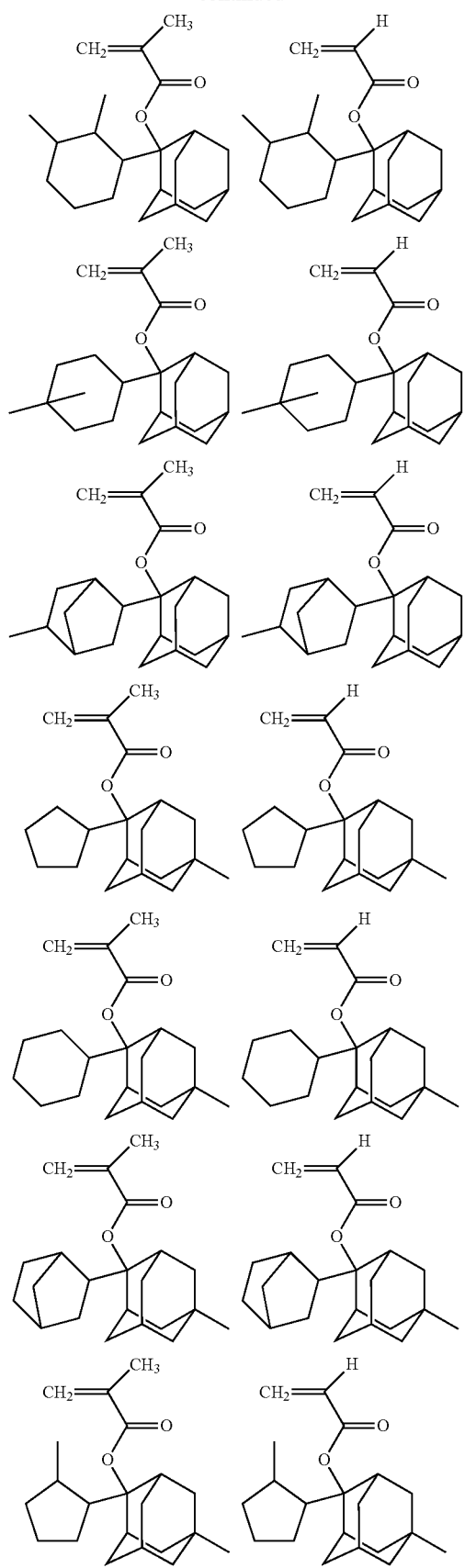
104
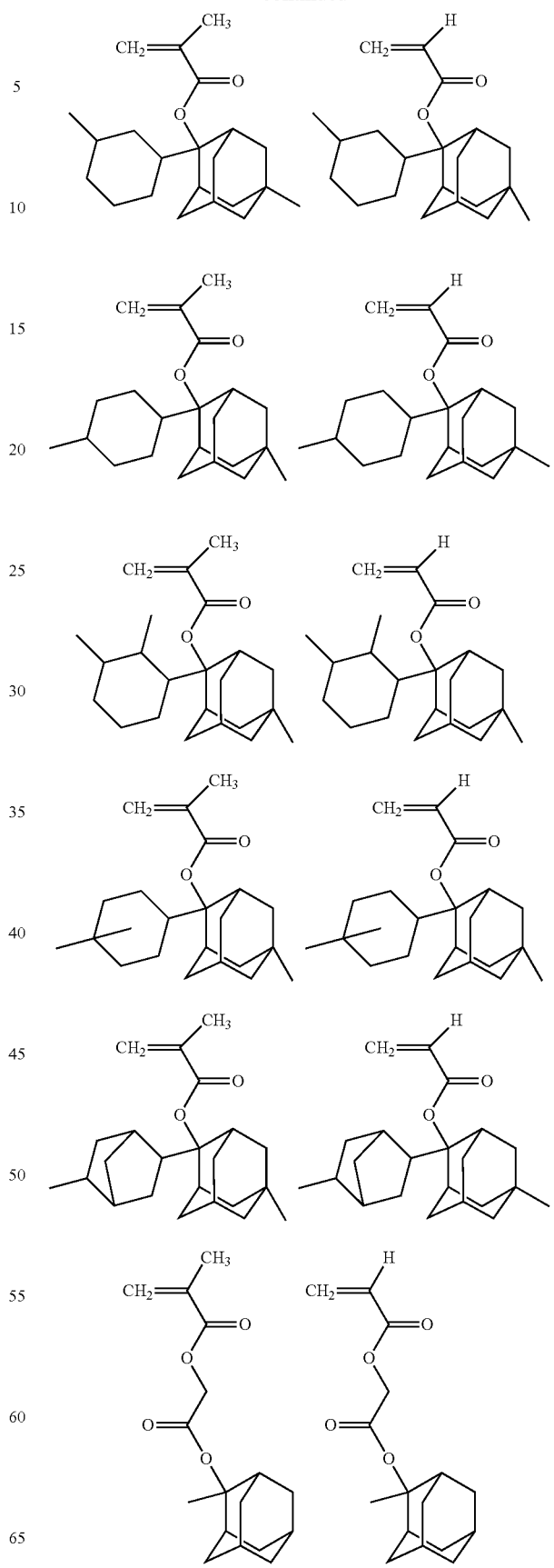

-continued

107
-continued
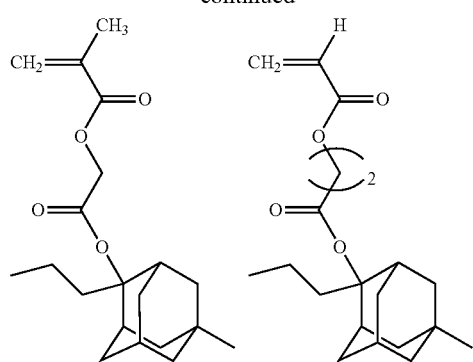
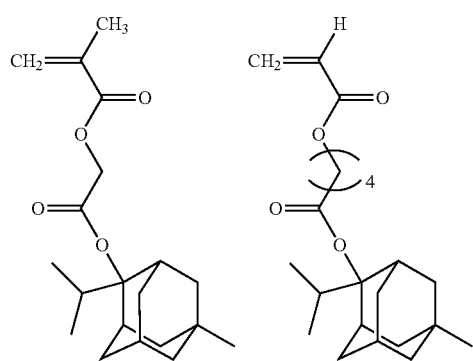
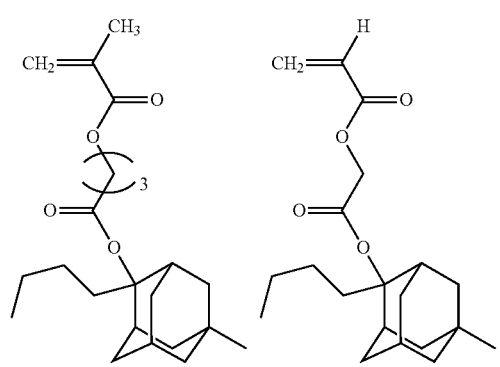
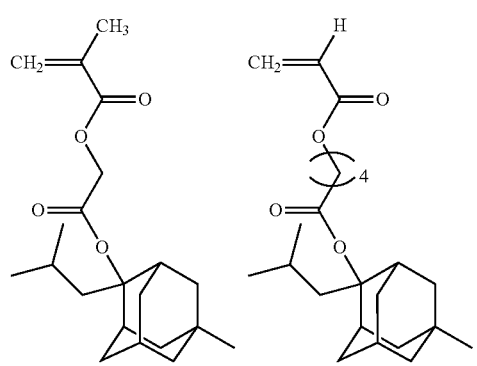
108
-continued
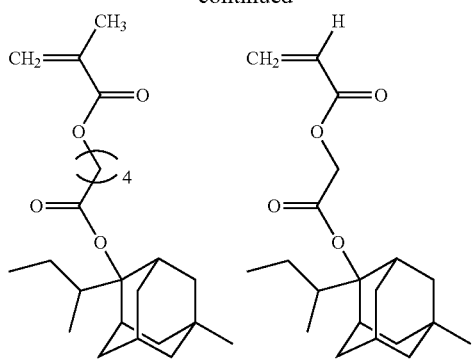
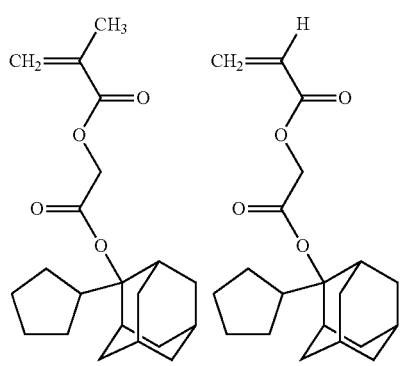
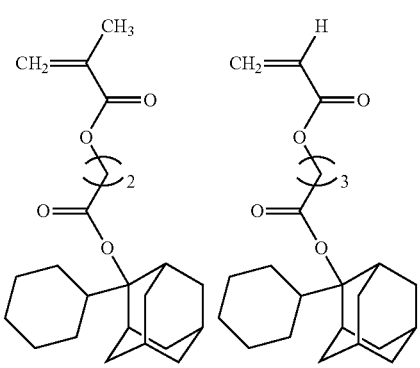
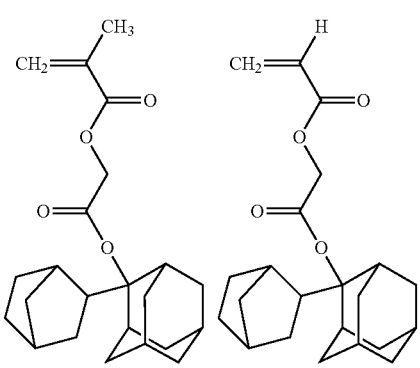

109
-continued
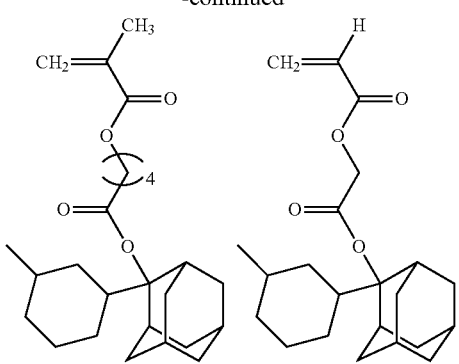
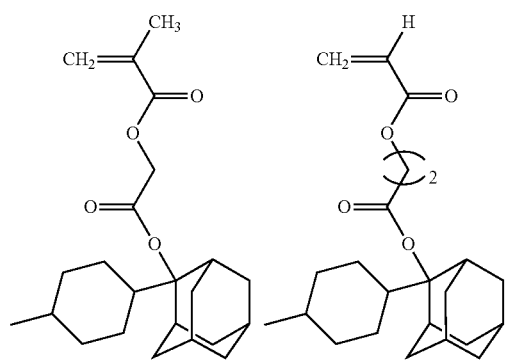
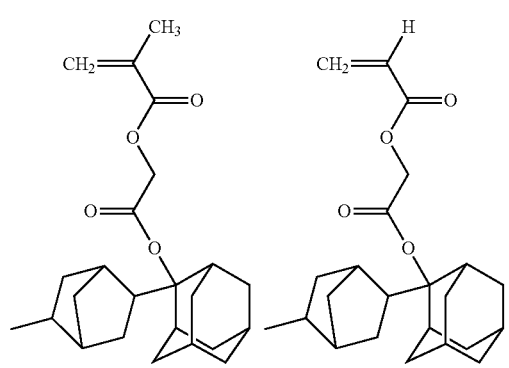
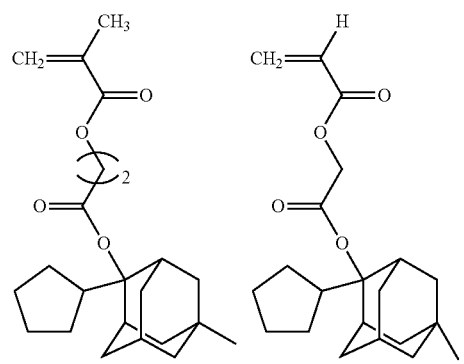
110
-continued
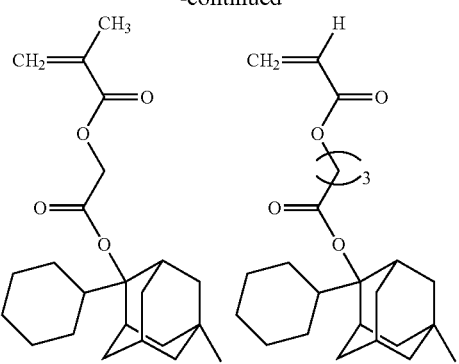
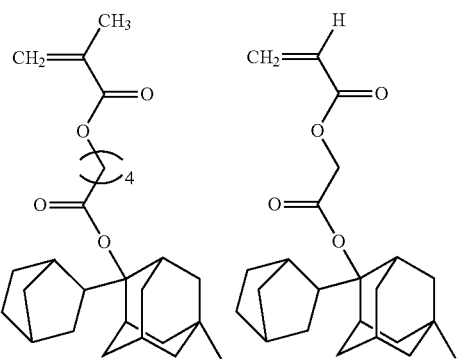
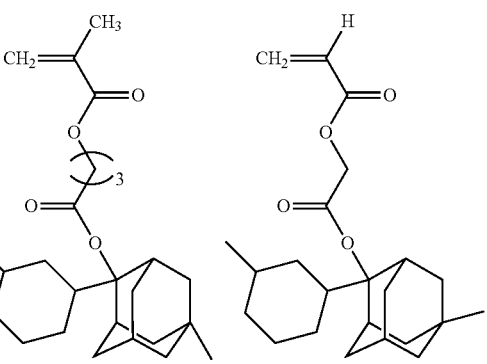
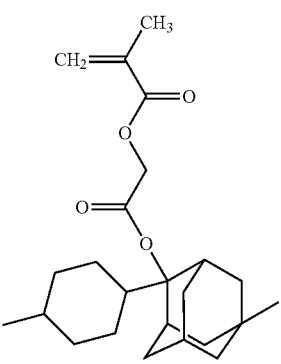

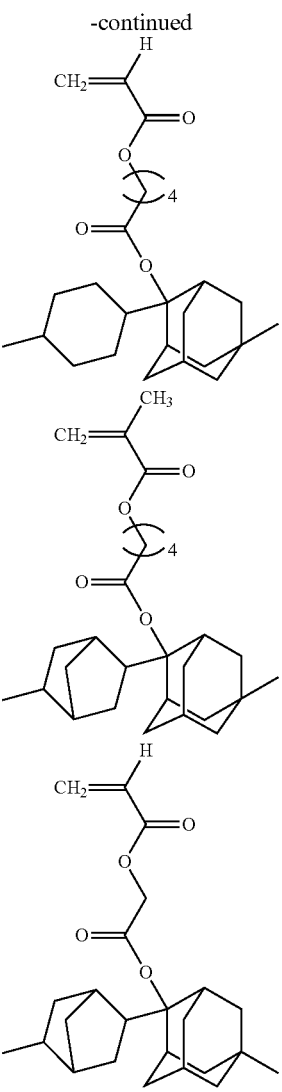

Among them, preferred are 2-methyl-2-adamantyl acrylate, 2-methyl-2-adamantylmethacrylate, 2-ethyl-2-adamantyl acrylate, 2-ethyl-2-adamantyl methacrylate, 2-isopropyl-2-adamantyl acrylate and 2-isopropyl-2-adamantyl methacrylate, and more preferred are 2-methyl-2-adamantyl methacrylate, 2-ethyl-2-adamantyl methacrylate, and 2-isopropyl-2-adamantyl methacrylate.

Examples of the monomer represented by the formula (a-2) include the followings.

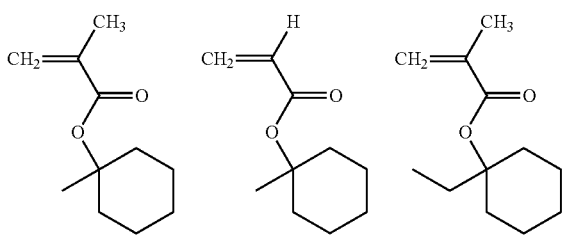

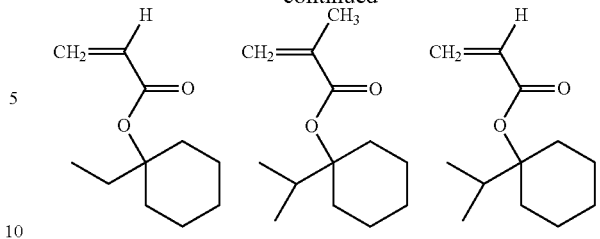

Among them, preferred are 1-ethyl-1-cyclohexyl acrylate and 1-ethyl-1-cyclohexyl methacrylate, and more preferred is 1-ethyl-1-cyclohexyl methacrylate.

The content of the structural unit derived from a compound having an acid-labile group in the resin is usually 10 to 95% by mole, preferably 15 to 90% by mole and more preferably 20 to 85% by mole based on 100% by mole of all the structural units of the resin.

Other examples of the compound having an acid-labile group include a monomer represented by the formula (a-3):

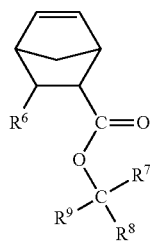

(a-3)

wherein $R^6$ represents a hydrogen atom, a C1-C3 aliphatic hydrocarbon group which can have one or more substituents, a carboxyl group, a cyano group or a —COOR$^m$ group in which R$^m$ represents a C1-C8 aliphatic hydrocarbon group or a C3-C8 saturated cyclic hydrocarbon group, and the C1-C8 aliphatic hydrocarbon group and the C3-C8 saturated cyclic hydrocarbon group can have one or more hydroxyl groups, and one or more —CH$_2$— in the C1-C8 aliphatic hydrocarbon group and the C3-C8 saturated cyclic hydrocarbon group can be replaced by —O— or —CO—, $R^7$, $R^8$ and $R^9$ independently represent a C1-C12 aliphatic hydrocarbon group or a C3-C12 saturated cyclic hydrocarbon group, or $R^8$ and $R^9$ are bonded each other to form a ring together with the carbon atom to which $R^8$ and $R^9$ are bonded, and the C1-C12 aliphatic hydrocarbon group and the C3-C12 saturated cyclic hydrocarbon group can have one or more hydroxyl groups, and one or more —CH$_2$— in the C1-C12 aliphatic hydrocarbon group and the C3-C12 saturated cyclic hydrocarbon group can be replaced by —O— or —CO—.

Examples of the substituent include a hydroxyl group. Examples of the C1-C3 aliphatic hydrocarbon group which can have one or more substituents include a methyl group, an ethyl group, a propyl group, a hydroxymethyl group and a 2-hydroxyethyl group. Examples of $R^{a13}$ include a methyl group, an ethyl group, a propyl group, a 2-oxo-oxolan-3-yl group and a 2-oxo-oxolan-4-yl group. Examples of $R^{a10}$, $R^{a11}$ and $R^{a12}$ include a methyl group, and ethyl group, a cyclohexyl group, a methylcyclohexyl group, a hydroxycyclohexyl group, an oxocyclohexyl group and an adamantyl group, and examples of the ring formed by bonding $R^8$ and $R^9$ each other together with the carbon atom to which $R^8$ and $R^9$ are bonded include a cyclohexane ring and an adamantane ring.

Examples of the monomer represented by the formula (a-3) include tert-butyl 5-norbornene-2-carboxylate, 1-cyclohexyl-1-methylethyl 5-norbornene-2-carboxylate, 1-methylcyclohexyl 5-norbornene-2-carboxylate, 2-methyl-2-adamantyl 5-norbornene-2-carboxylate, 2-ethyl-2-adamantyl 5-norbornene-2-carboxylate, 1-(4-methylcyclohexyl)-1-methylethyl 5-norbornene-2-carboxylate, 1-(4-hydroxylcyclohexyl)-1-methylethyl 5-norbornene-2-carboxylate, 1-methyl-1-(4-oxocyclohexyl)ethyl 5-norbornene-2-carboxylate and 1-(1-adamantyl)-1-methylethyl 5-norbornene-2-carboxylate.

When the resin has a structural unit derived from the monomer represented by the formula (a-3), the photoresist composition having excellent resolution and higher dry-etching resistance tends to be obtained.

When the resin contains the structural unit derived form the monomer represented by the formula (a-3), the content of the structural unit derived from the monomer represented by the formula (a-3) is usually 10 to 95% by mole and preferably 15 to 90% by mole and more preferably 20 to 85% by mole based on total molar of all the structural units of the resin.

Other examples of the compound having an acid-labile group include a monomer represented by the formula (a-4):

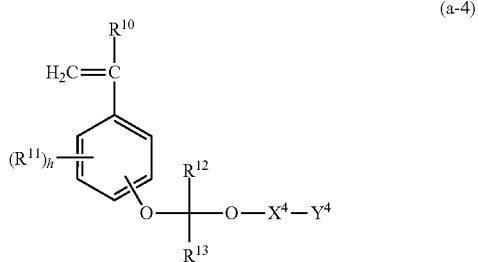

(a-4)

wherein $R^{10}$ represents a hydrogen atom, a halogen atom, a C1-C6 alkyl group or a C1-C6 halogenated alkyl group, $R^{11}$ is independently in each occurrence a halogen atom, a hydroxyl group, a C1-C6 alkyl group, a C1-C6 alkoxy group, a C2-C4 acyl group, a C2-C4 acyloxy group, an acryloyl group or a methacryloyl group, la represents an integer of 0 to 4, $R^{12}$ and $R^{13}$ each independently represent a hydrogen atom or a C1-C12 hydrocarbon group, $X^4$ represents a single bond or a C1-C17 divalent saturated hydrocarbon group in which one or more —$CH_2$— can be replaced by —O—, —CO—, —S—, —$SO_2$— or —N($R^c$)— wherein $R^c$ represents a hydrogen atom or a C1-C6 alkyl group, and $Y^4$ represents a C1-C12 aliphatic hydrocarbon group, a C3-C18 saturated cyclic hydrocarbon group or a C6-C18 aromatic hydrocarbon group, and the C1-C12 aliphatic hydrocarbon group, the C2-C18 saturated cyclic hydrocarbon group and the C6-C18 aromatic hydrocarbon group can have one or more substituents.

Examples of the halogen atom include a fluorine atom.

Examples of the C1-C6 alkyl group include a methyl group, an ethyl group, a propyl group, an isopropyl group, a butyl group, an isobutyl group, a sec-butyl group, a tert-butyl group, a pentyl group and a hexyl group, and a C1-C4 alkyl group is preferable and a C1-C2 alkyl group is more preferable and a methyl group is especially preferable.

Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group and a perfluorohexyl group.

Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferable and a C1-C2 alkoxy group is more preferable and a methoxy group is especially preferable.

Examples of the C2-C4 acyl group include an acetyl group, a propionyl group and a butyryl group, and examples of the C2-C4 acyloxy group include an acetyloxy group, a propionyloxy group and a butyryloxy group.

Examples of the C1-C12 hydrocarbon group include a C1-C12 aliphatic hydrocarbon group such as a methyl group, an ethyl group, a propyl group, an isopropyl group, a butyl group, an isobutyl group, a sec-butyl group, a tert-butyl group, a pentyl group, a hexyl group, a heptyl group, an octyl group, a 2-ethylhexyl group, a nonyl group, a decyl group, an undecyl group and a dodecyl group, and a C3-C12 saturated cyclic hydrocarbon group such as a cyclohexyl group, an adamantyl group, a 2-alkyl-2-adamantyl group, a 1-(1-adamantyl)-1-alkyl group and an isobornyl group.

Examples of the C1-C17 divalent saturated hydrocarbon group include a C1-C17 alkanediyl group such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, a undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group and a heptadecane-1,17-diyl group.

Examples of the C1-C12 aliphatic hydrocarbon group include a methyl group, an ethyl group, a propyl group, an isopropyl group, a butyl group, an isobutyl group, a sec-butyl group, a tert-butyl group, a pentyl group, a hexyl group, a heptyl group, an octyl group, a 2-ethylhexyl group, a nonyl group, a decyl group, an undecyl group and a dodecyl group. Examples of the C3-C18 saturated cyclic hydrocarbon group include a cyclopropyl group, a cyclobutyl group, a cycloheptyl group, a cyclohexyl group, a cycloheptyl group, a cyclooctyl group, a cyclononyl group, a cyclodecyl group, a norbornyl group, a 1-adamantyl group, a 2-adamantyl group, an isobornyl group and the following groups:

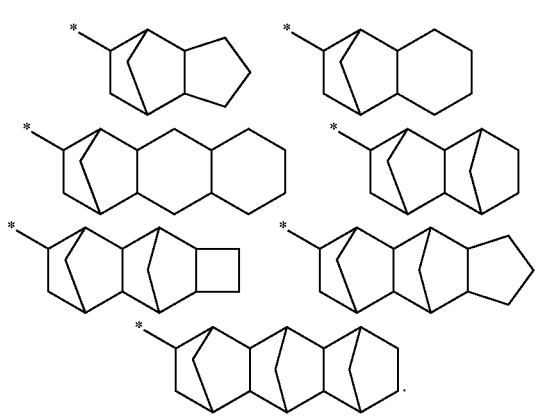

Examples of the C6-C18 aromatic hydrocarbon group include a phenyl group, a naphthyl group, an anthryl group, a p-methylphenyl group, a p-tert-butylphenyl group and a p-adamantylphenyl group.
Examples of the monomer represented by the formula (a-4) include the followings.
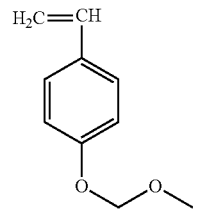
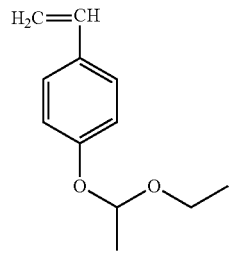
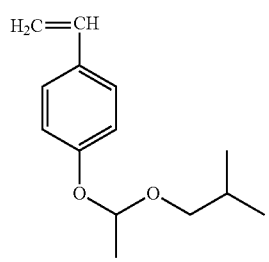
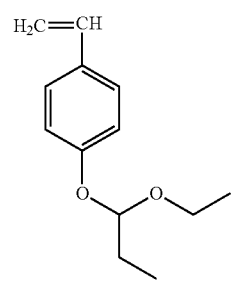
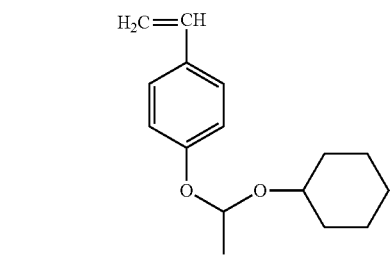
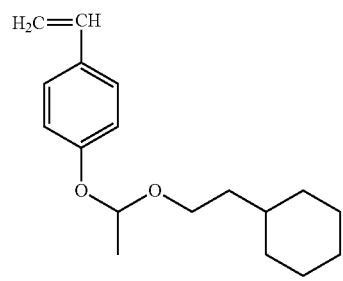
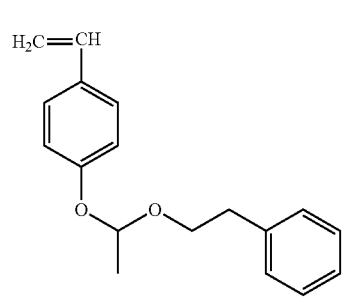
-continued
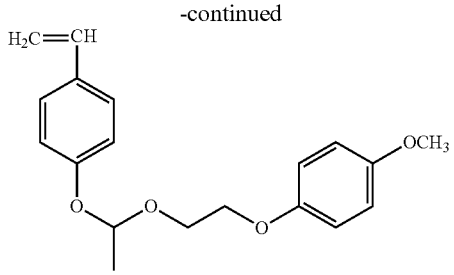
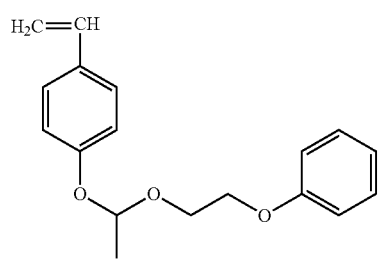
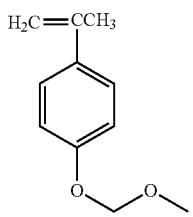
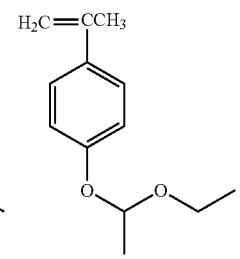
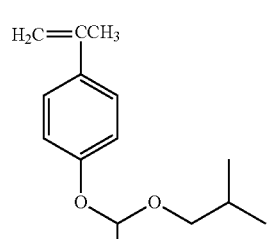
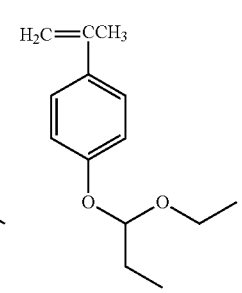
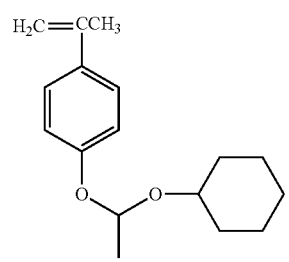
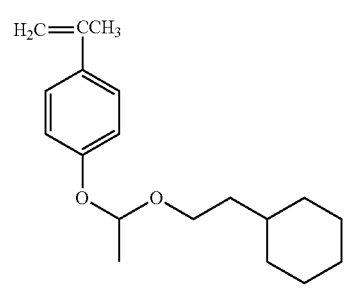

117 118
-continued -continued
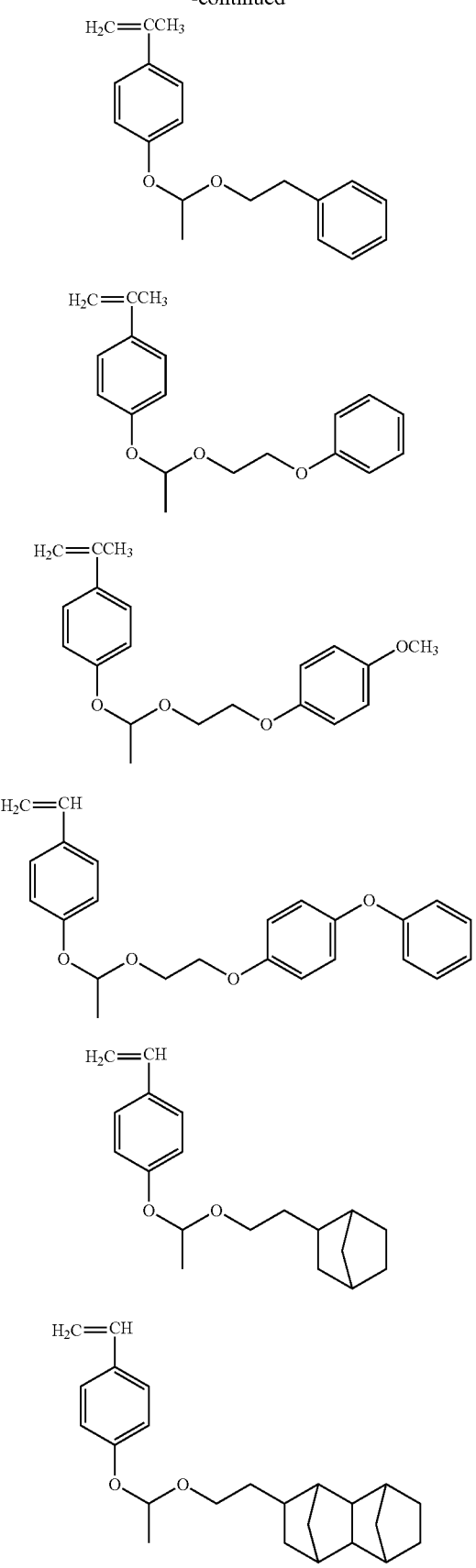
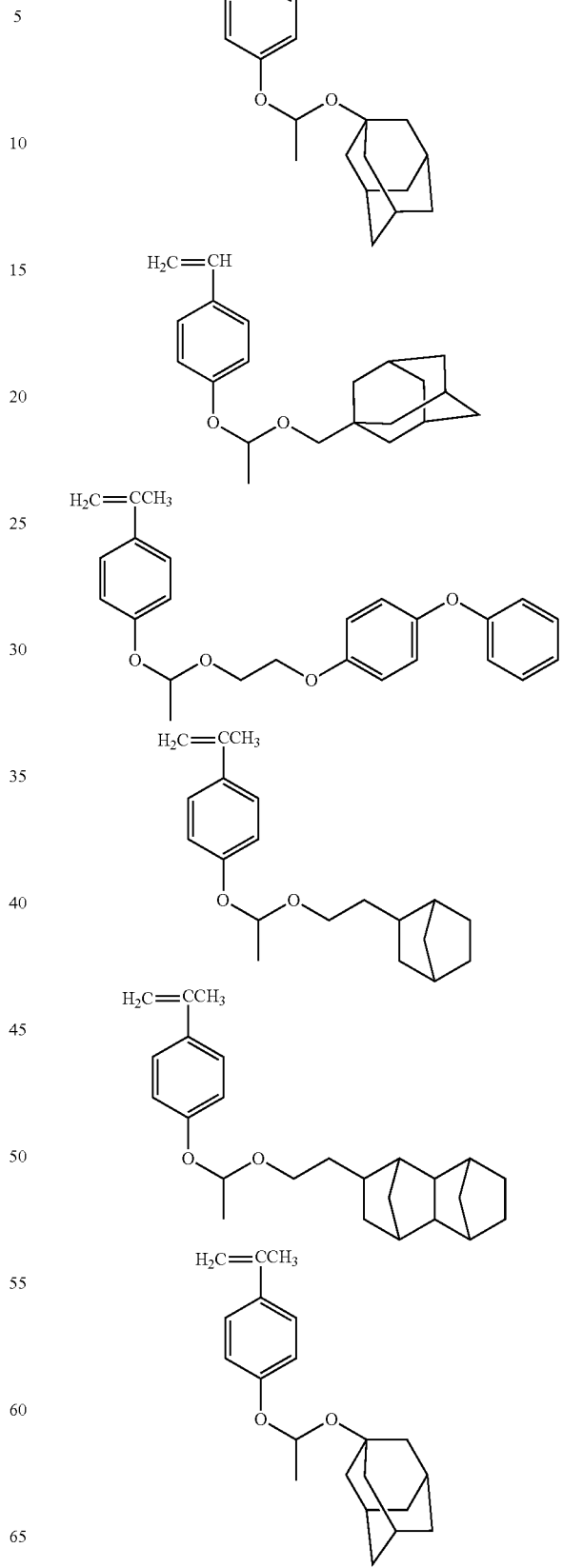

119
-continued
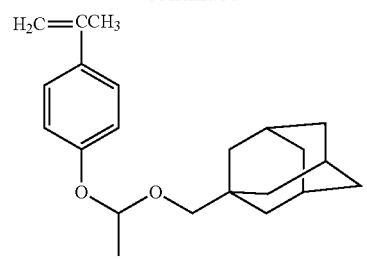
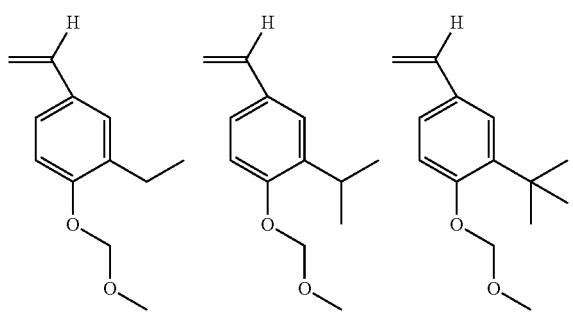
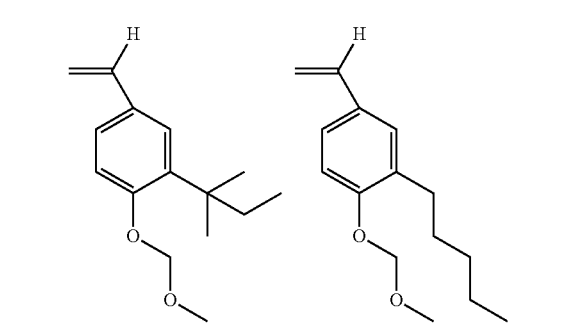
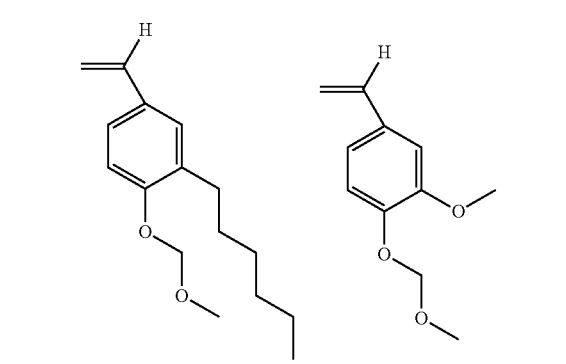
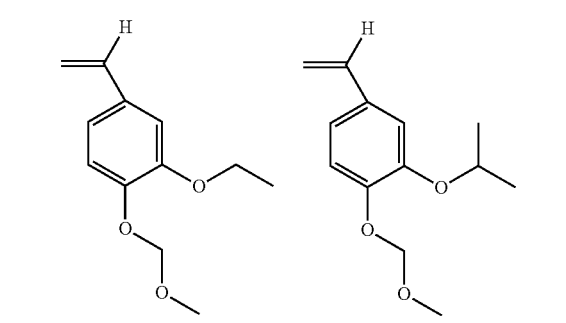
120
-continued
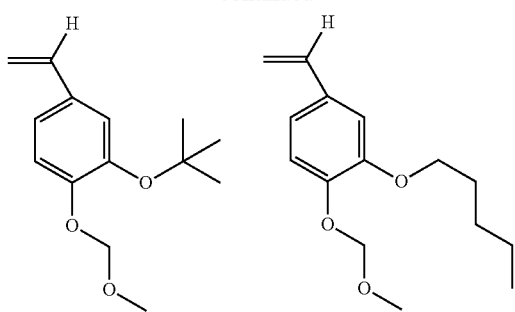
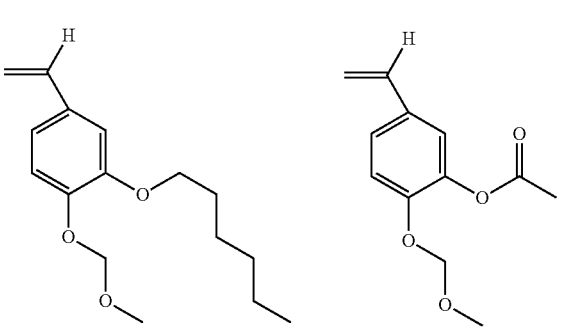
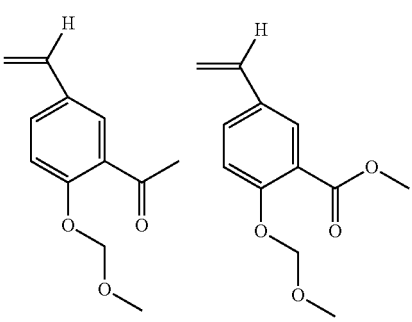
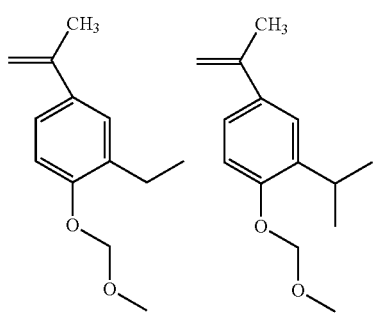
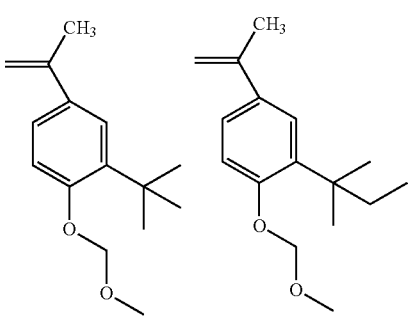

-continued

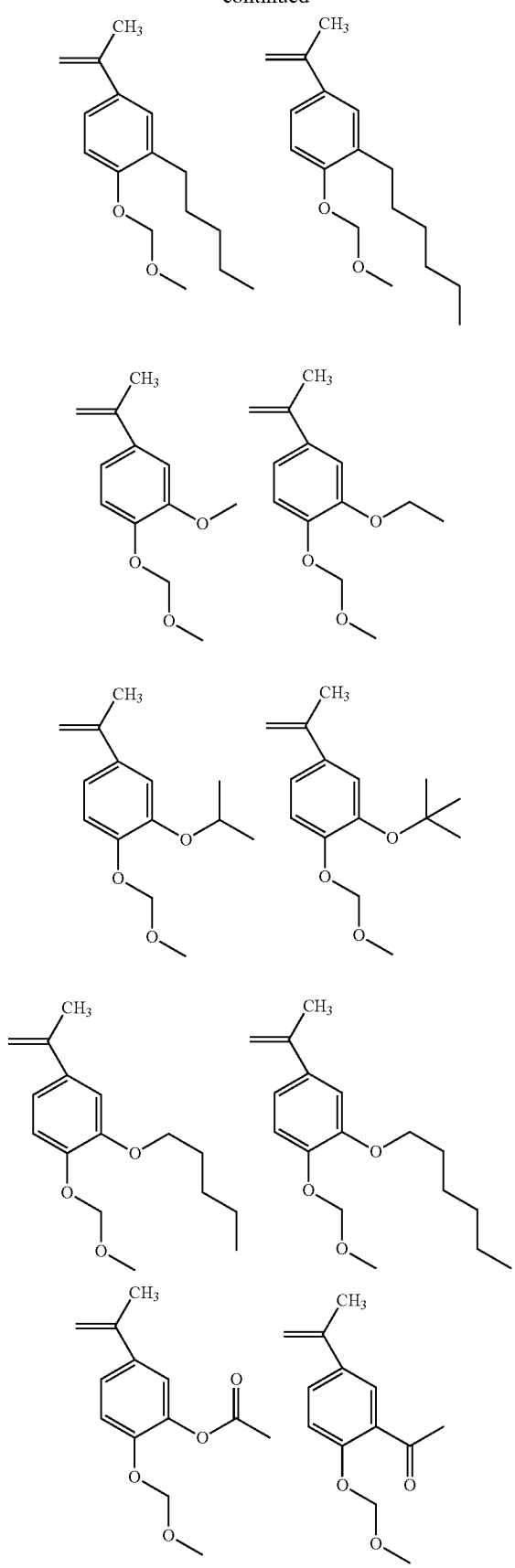
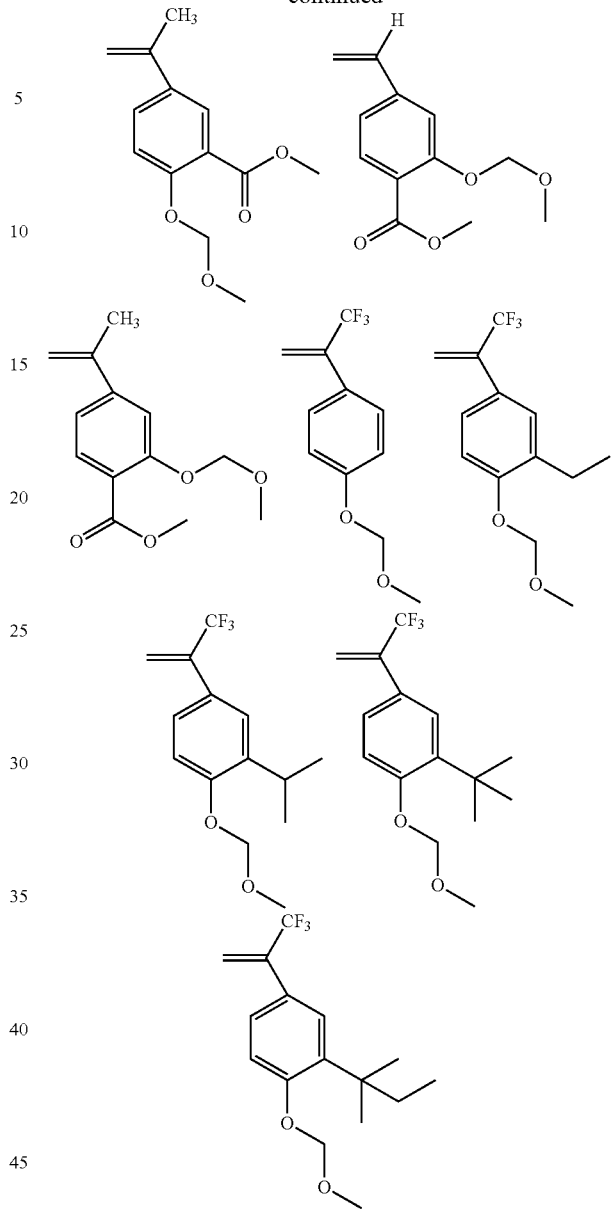

When the resin contains the structural unit derived form the monomer represented by the formula (a-4), the content of the structural unit derived from the monomer represented by the formula (a-4) is usually 10 to 95% by mole and preferably 15 to 90% by mole and more preferably 20 to 85% by mole based on total molar of all the structural units of the resin.

The resin can have two or more kinds of structural units derived from the compounds having an acid-labile group.

The resin preferably contains the structural unit derived from the compound having an acid-labile group and a structural unit derived from the compound having no acid-labile group. The resin can have two or more kinds of structural units derived from the compounds having no acid-labile group. When the resin contains the structural unit derived from the compound having an acid-labile group and the structural unit derived from the compound having no acid-labile group, the content of the structural unit derived from the compound having an acid-labile group is usually 10 to 80% by mole and preferably 20 to 60% by mole based on total molar of all the structural units of the resin. The content of the structural unit derived from a monomer having an adamantyl group, especially the monomer represented by the formula (a-1) in the structural unit derived from the compound having no acid-labile group is preferably 15% by mole or more from the viewpoint of dry-etching resistance of the photoresist composition.

The compound having no acid-labile group preferably contains one or more hydroxyl groups or a lactone ring. When the resin contains the structural unit derived from the compound having no acid-labile group and having one or more hydroxyl groups or a lactone ring, a photoresist composition having good resolution and adhesiveness of photoresist to a substrate tends to be obtained.

Examples of the compound having no acid-labile group and having one or more hydroxyl groups include a monomer represented by the formula (b-1):

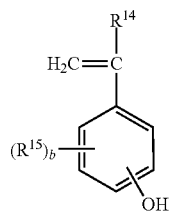

(b-1)

wherein $R^{14}$ represents a hydrogen atom, a halogen atom, a C1-C6 alkyl group or a C1-C6 halogenated alkyl group, $R^{15}$ is independently in each occurrence a halogen atom, a hydroxyl group, a C1-C6 alkyl group, a C1-C6 alkoxy group, a C2-C4 acyl group, a C2-C4 acyloxy group, an acryloyl group or a methacryloyl group, b represents an integer of 0 to 4, and a monomer represented by the formula (b-2):

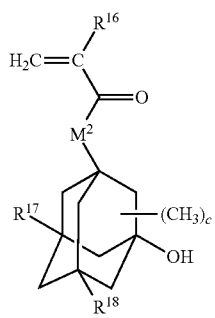

(b-2)

wherein $R^{16}$ represents a hydrogen atom or a methyl group, $R^{17}$ and $R^{18}$ independently represent a hydrogen atom, a methyl group or a hydroxyl group, $M^2$ represents *—O— or *—O—$(CH_2)_{k2}$—CO—O— in which * represents a binding position to —CO—, and k2 represents an integer of 1 to 7, and c represents an integer of 0 to 10.

When KrF excimer laser (wavelength: 248 nm) lithography system, or a high energy laser such as electron beam and extreme ultraviolet is used as an exposure system, the resin containing the structural unit derived from the monomer represented by the formula (b-1) is preferable, and when ArF excimer laser (wavelength: 193 nm) is used as an exposure system, the resin containing the structural unit derived from the monomer represented by the formula (b-2) is preferable.

In the formula (b-1), examples of the halogen atom include a fluorine atom, examples of the C1-C6 alkyl group include a methyl group, an ethyl group, a propyl group, an isopropyl group, a butyl group, an isobutyl group, a sec-butyl group, a tert-butyl group, a pentyl group and a hexyl group, and a C1-C4 alkyl group is preferable and a C1-C2 alkyl group is more preferable and a methyl group is especially preferable. Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group and a perfluorohexyl group. Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferable and a C102 alkoxy group is more preferable and a methoxy group is especially preferable.

Examples of the C2-C4 acyl group include an acetyl group, a propionyl group and a butyryl group, and examples of the C2-C4 acyloxy group include an acetyloxy group, a propionyloxy group and a butyryloxy group. In the formula (b-1), ma is preferably 0, 1 or 2, and is more preferably 0 or 1, and especially preferably 0.

The resin containing the structural unit derived from the monomer represented by the formula (b-1) and the structural unit derived from the compound having an acid generator can be produced, for example, by polymerizing the compound having an acid generator and a monomer obtained by protecting a hydroxyl group of the monomer represented by the formula (b-1) with an acetyl group followed by conducting deacetylation of the obtained polymer with a base.

Examples of the monomer represented by the formula (b-1) include the followings.

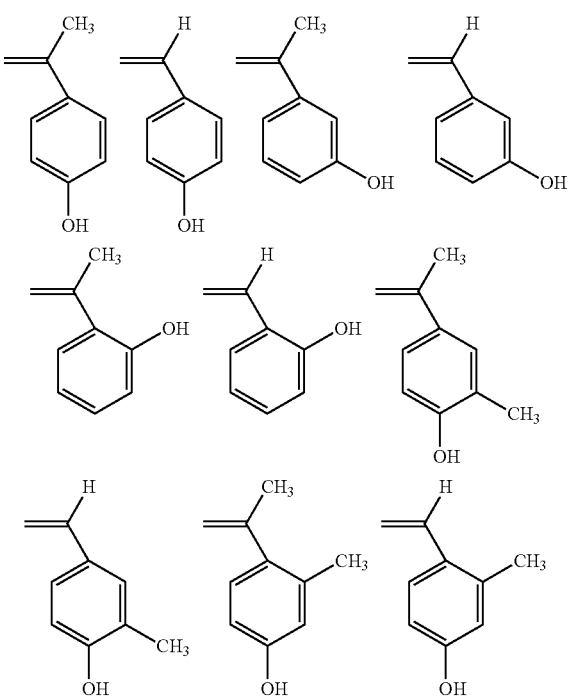

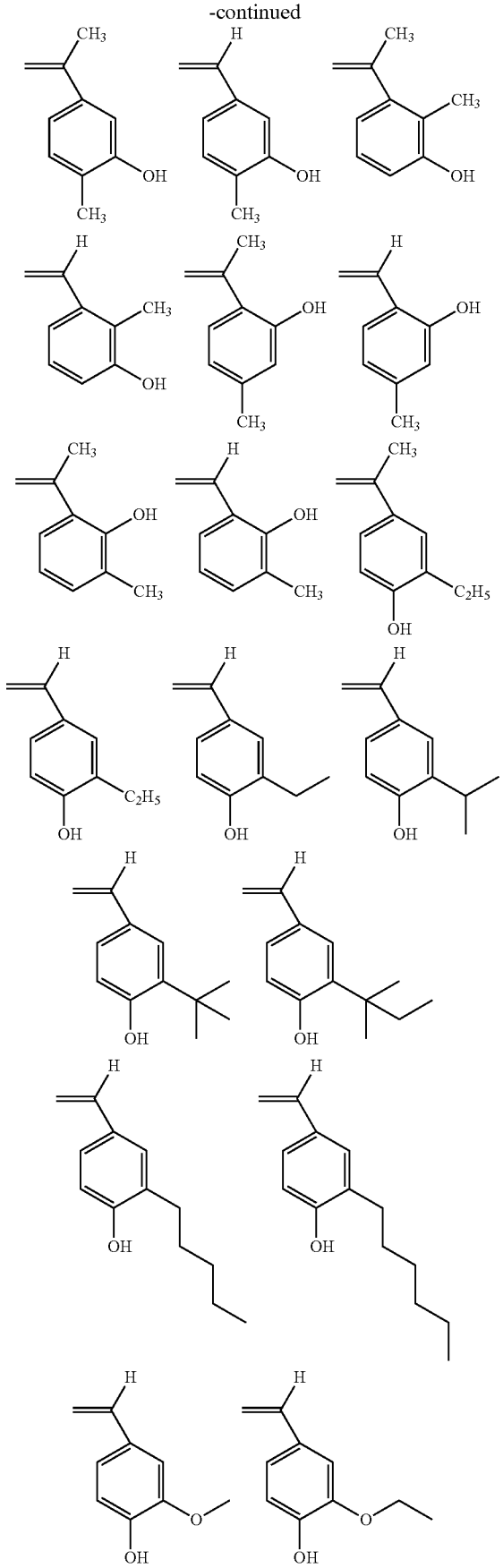
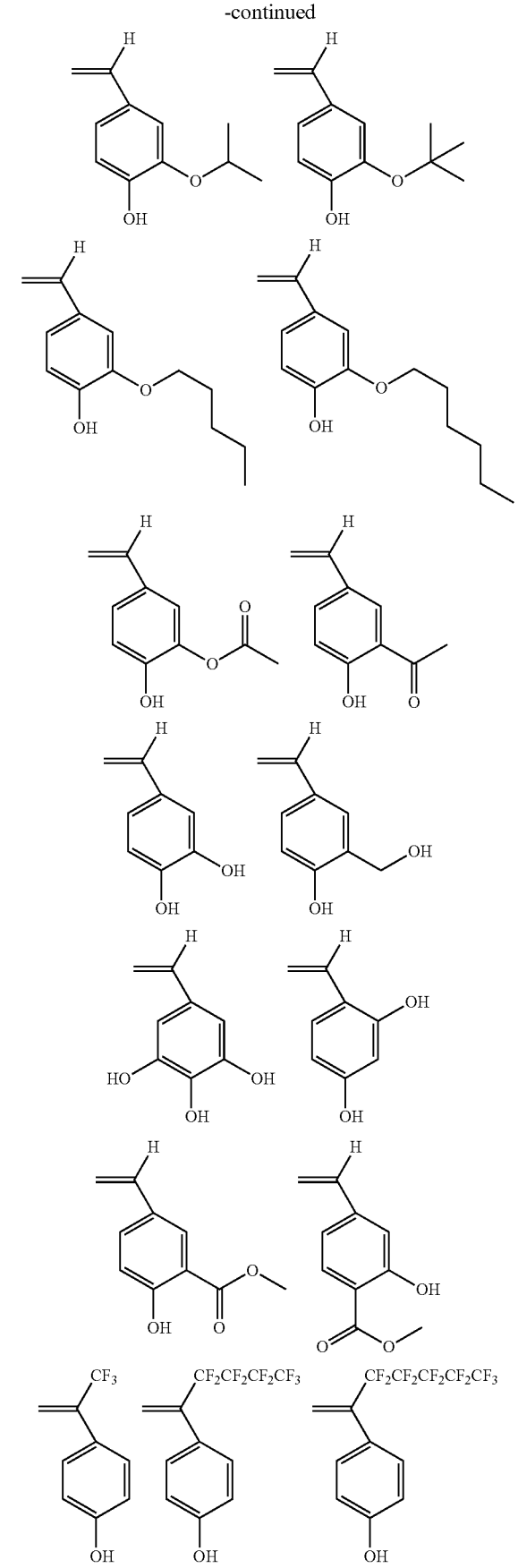

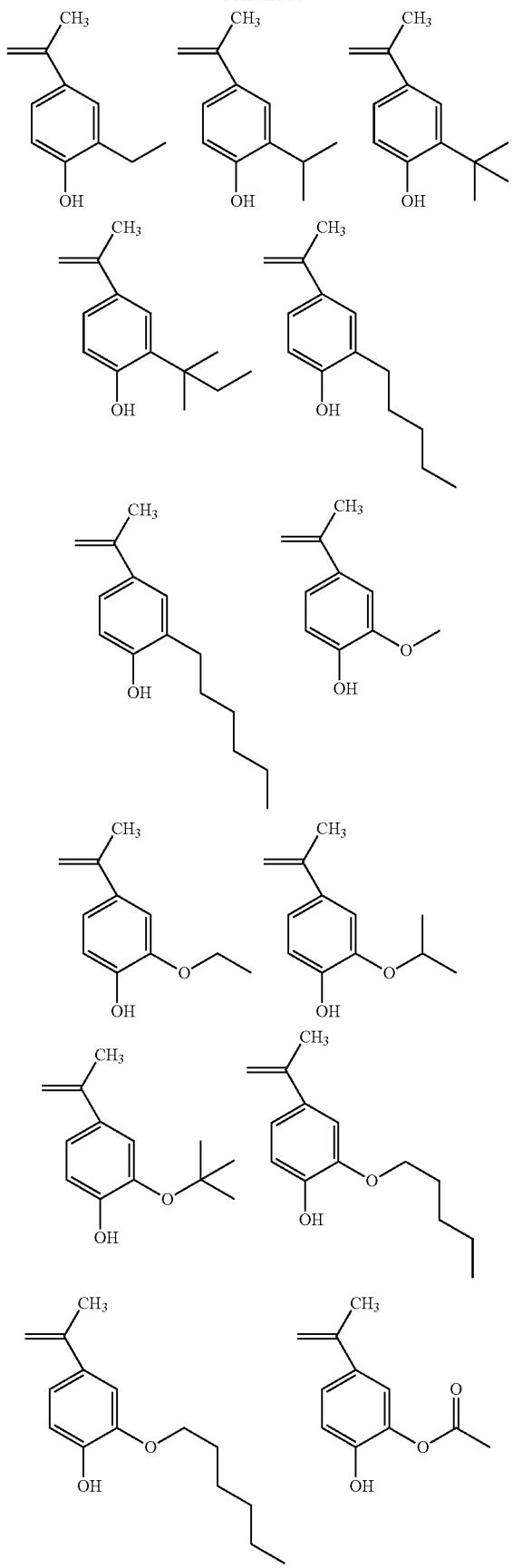
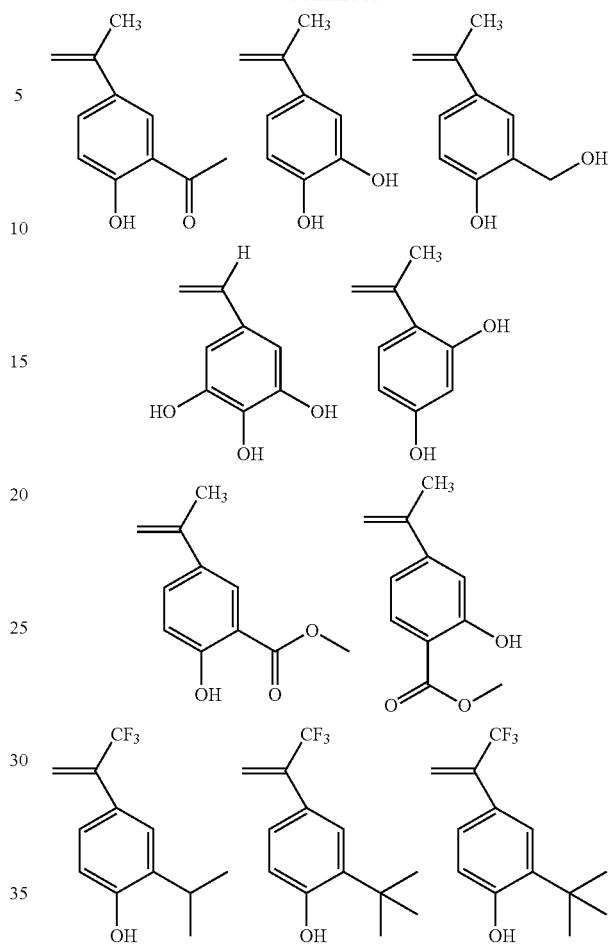

Among them, preferred are 4-hydroxystyrene and 4-hydroxy-α-methylstyrene.

When the resin contains the structural unit derived from the monomer represented by the formula (b-1), the content of the structural unit derived from the monomer represented by the formula (b-1) is usually 5 to 90% by mole and preferably 10 to 85% by mole and more preferably 15 to 80% by mole based on total molar of all the structural units of the resin.

In the formula (b-2), $R^{16}$ is preferably a methyl group, $R^{17}$ is preferably a hydrogen atom, $R^{18}$ is preferably a hydrogen atom or a hydroxyl group, $M^2$ is preferably *—O— or *—O—$(CH_2)_{f2}$—CO—O— in which * represents a binding position to —CO—, and f2 represents an integer of 1 to 4, and is more preferably *—O—, and c is preferably 0, 1, 2 or 3 and is more preferably 0 or 1.

Examples of the monomer represented by the formula (b-2) include the followings, and 3-hydroxy-1-adamantyl acrylate, 3-hydroxy-1-adamantyl methacrylate, 3,5-dihydroxy-1-adamantyl acrylate, 3,5-dihydroxy-1-adamantyl methacrylate, 1-(3,5-dihydroxy-1-adamantyloxycarbonyl) methyl acrylate and 1-(3,5-dihydroxy-1-adamantyloxycarbonyl)methyl methacrylate are preferable, and 3-hydroxy-1-adamantyl, methacrylate and 3,5-dihydroxy-1-adamantyl methacrylate are more preferable.

129
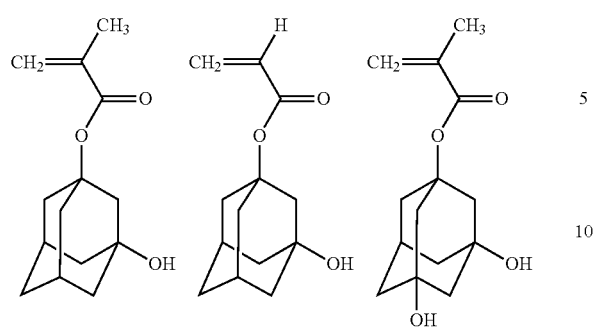
130
-continued
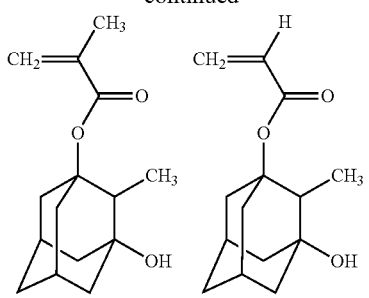
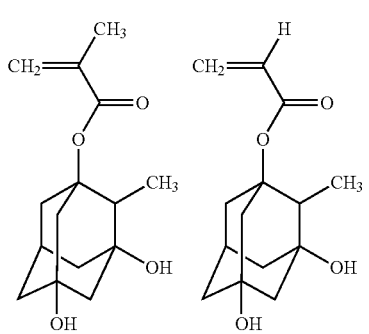
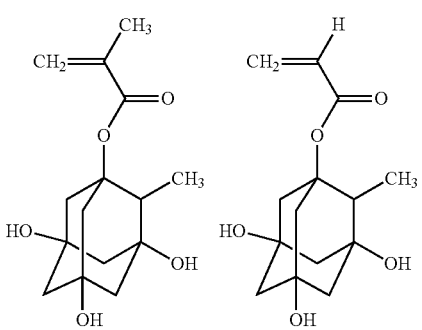
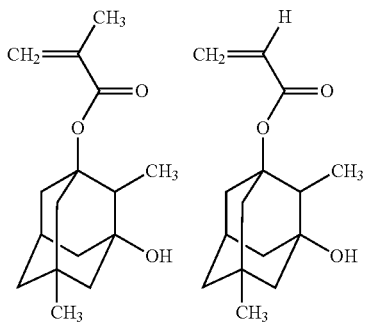
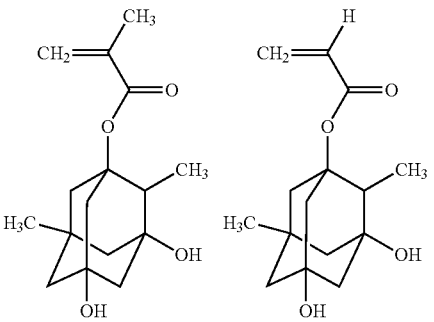

| 131 | 132 |
|---|---|
| -continued | -continued |
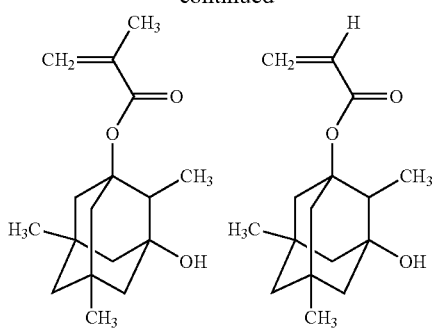
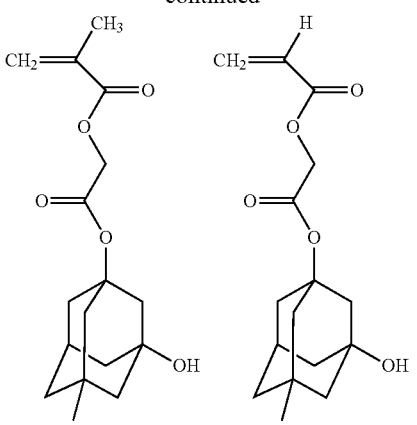
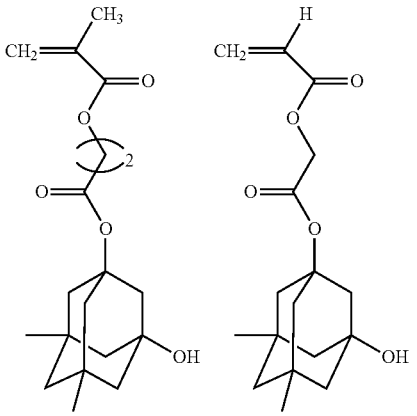
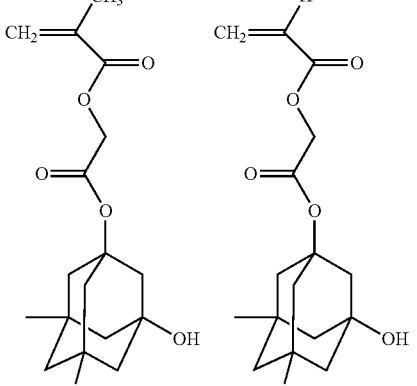
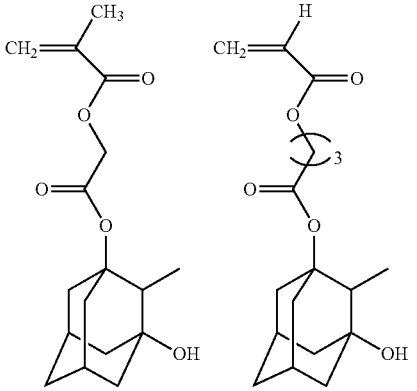

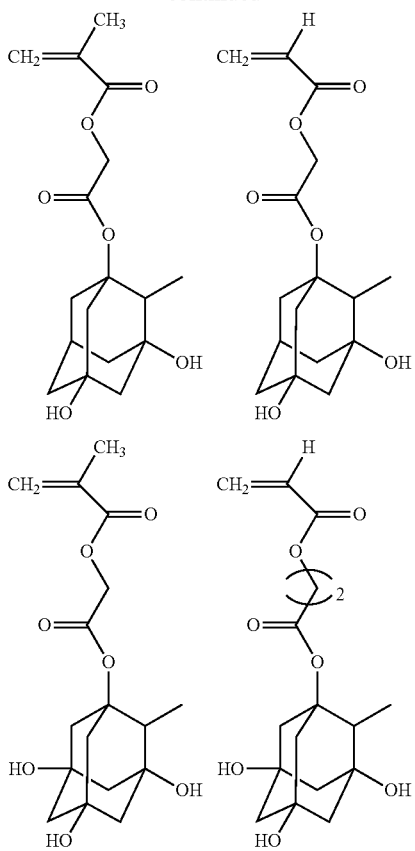

When the resin contains the structural unit derived from the monomer represented by the formula (b-2), the content of the structural unit derived from the monomer represented by the formula (b-2) is usually 3 to 40% by mole and preferably 5 to 35% by mole and more preferably 5 to 30% by mole based on total molar of all the structural units of the resin.

Examples of the lactone ring of the compound having no acid-labile group and having a lactone ring include a monocyclic lactone ring such as β-propiolactone ring, γ-butyrolactone ring and γ-valerolactone ring, and a condensed ring formed from a monocyclic lactone ring and the other ring. Among them, preferred are γ-butyrolactone ring and a condensed lactone ring formed from γ-butyrolactone ring and the other ring.

Preferable examples of the monomer having no acid-labile group and a lactone ring include the monomers represented by the formulae (c-1), (c-2) and (c-3):

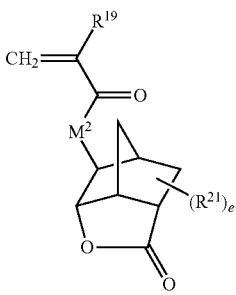

(c-2)

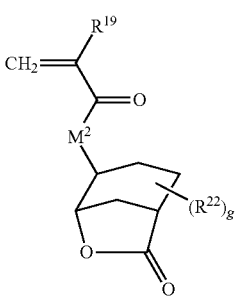

(c-3)

wherein $M^2$ independently represents *—O— or *—O—$(CH_2)_{k3}$—CO—O— in which * represents a binding position to —CO— and k3 represents an integer of 1 to 7, $R^{19}$ independently represents a hydrogen atom or a methyl group, $R^{20}$ represents a C1-C4 aliphatic hydrocarbon group, $R^{21}$ and $R^{22}$ are independently in each occurrence a carboxyl group, a cyano group or a C1-C4 aliphatic hydrocarbon group, and d represents an integer of 0 to 5, e and g independently represent an integer of 0 to 3.

It is preferred that $M^2$ is *—O— or *—O—$(CH_2)_{d1}$—CO—O— in which * represents a binding position to —CO— and d1 represents an integer of 1 to 4, and it is more preferred that $M^2$ is *—O—. $R^{19}$ is preferably a methyl group. $R^{20}$ is preferably a methyl group. It is preferred that $R^{21}$ and $R^{22}$ are independently in each occurrence a carboxyl group, a cyano group or a methyl group. It is preferred that d is an integer of 0 to 2, and it is more preferred that d is 0 or 1. It is preferred that e and g independently each represent an integer of 0 to 2, and it is more preferred that e and g independently each represent 0 or 1.

Examples of the monomer represented by the formula (c-1) include the followings.

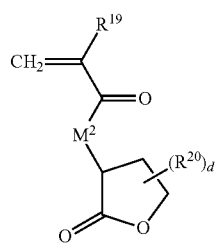

(c-1)

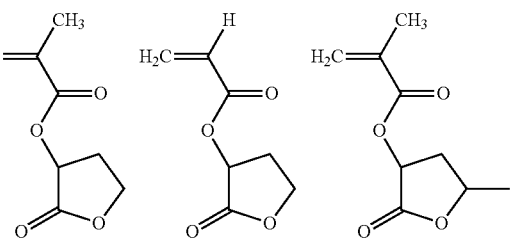

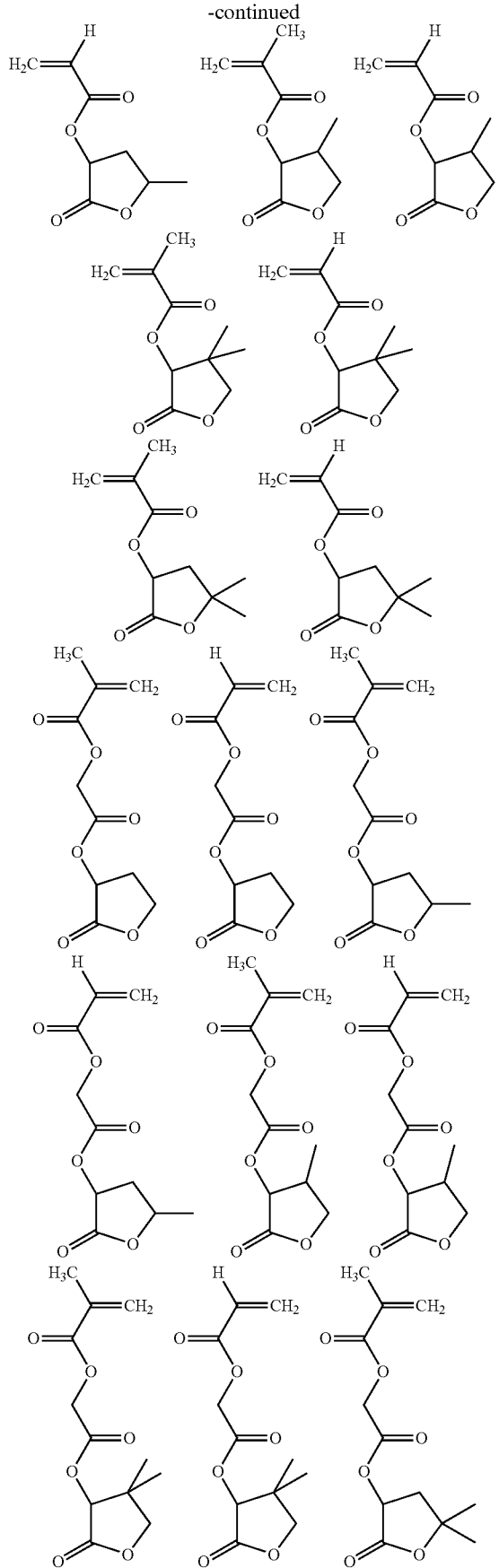
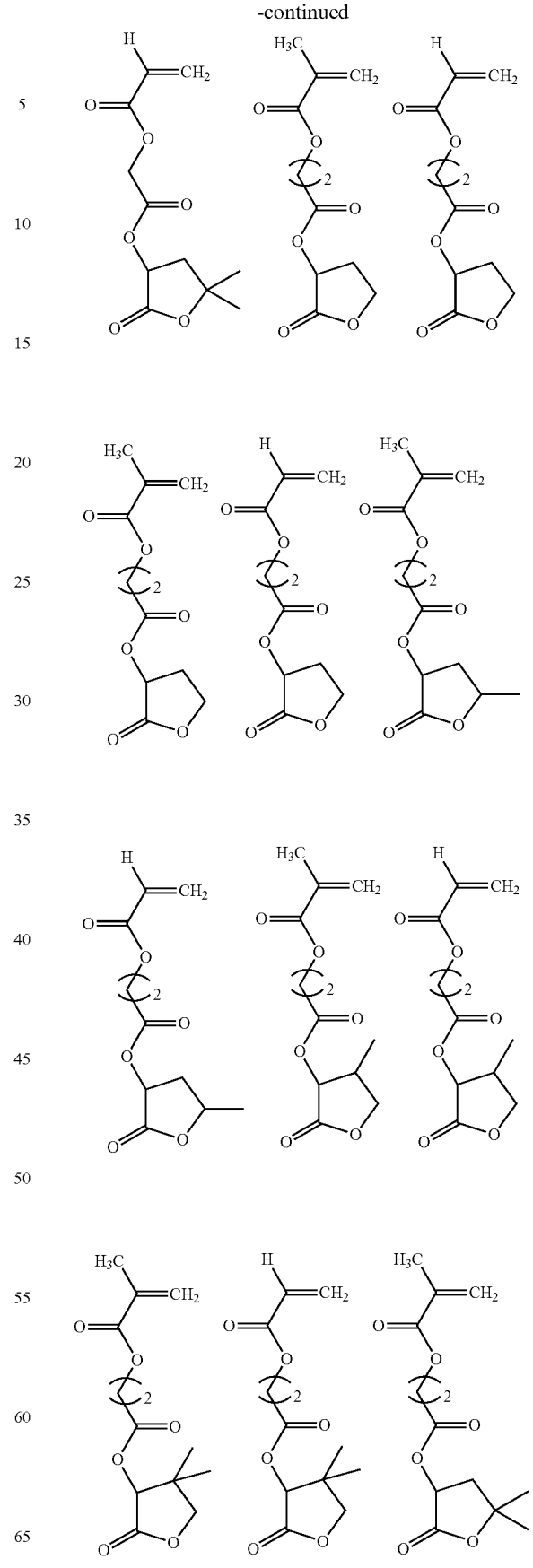

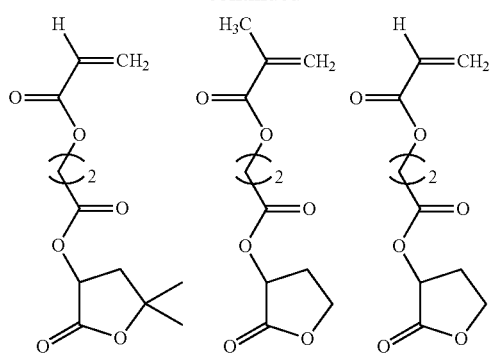
Examples of the monomer represented by the formula (c-2) include the followings.
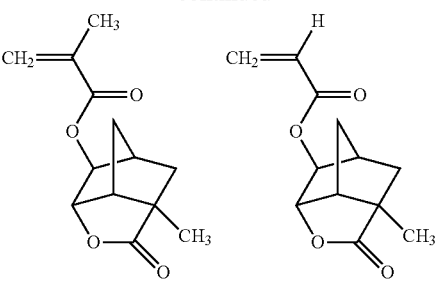
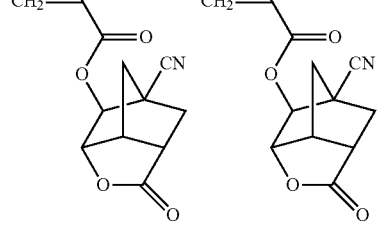
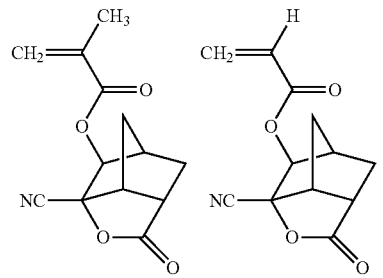
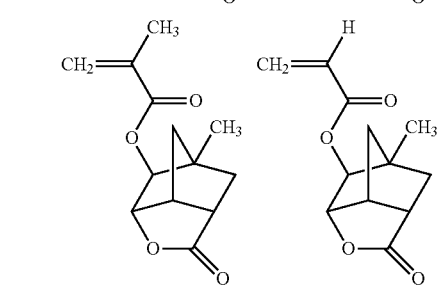
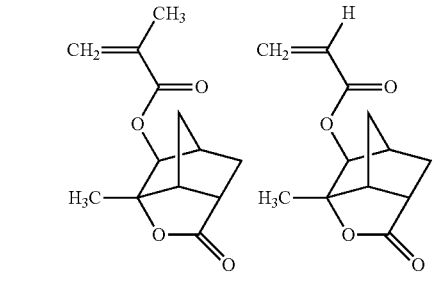
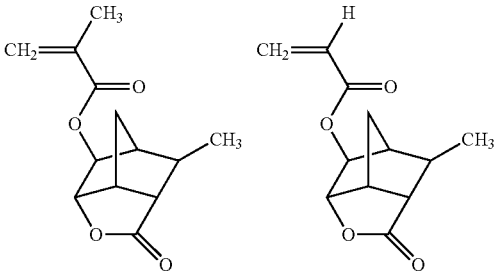
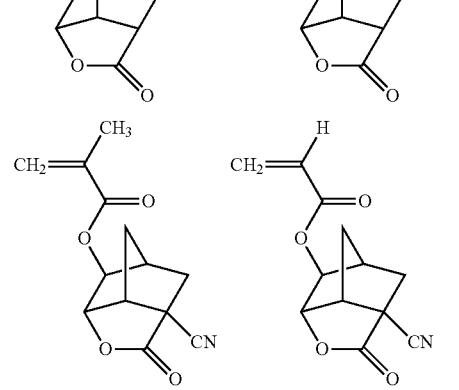
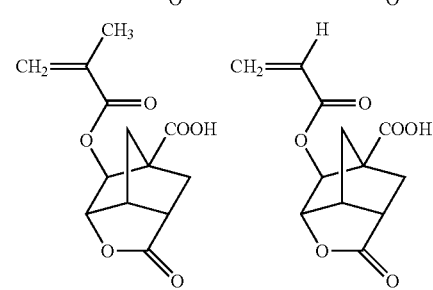

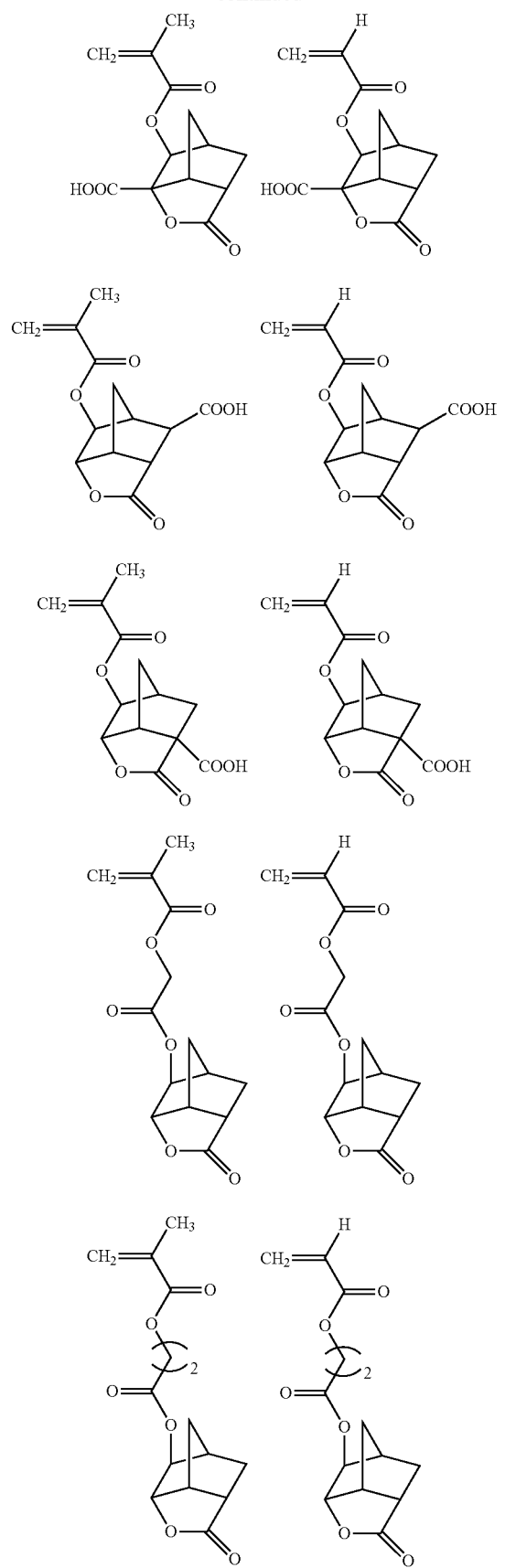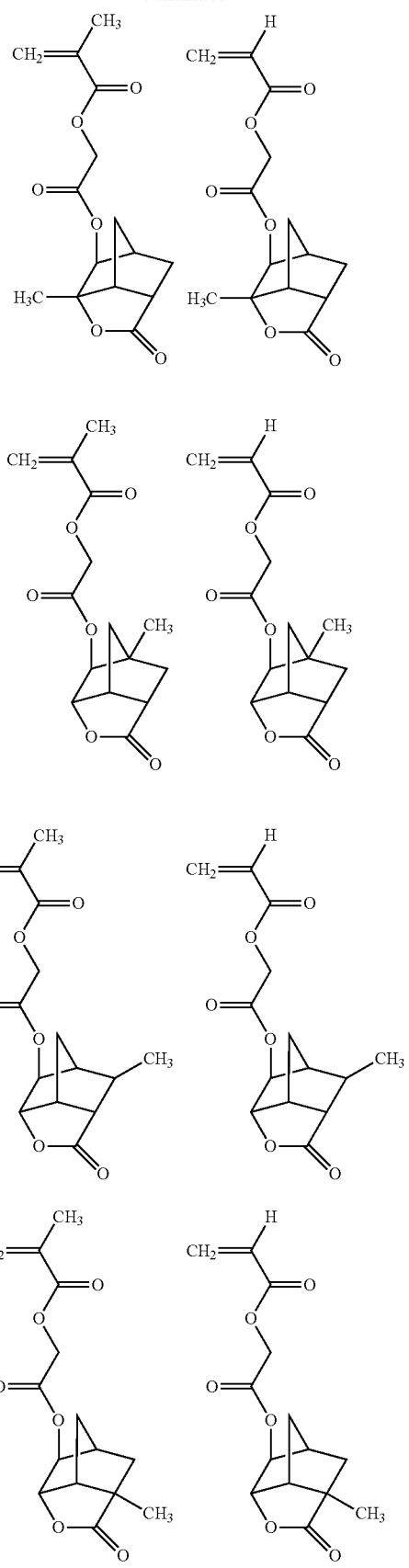

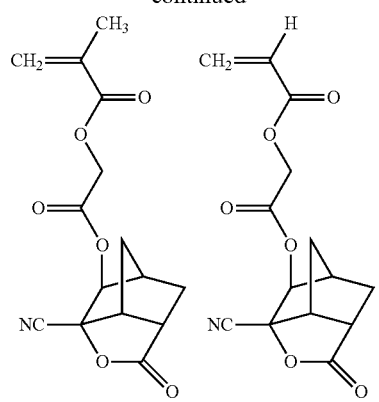
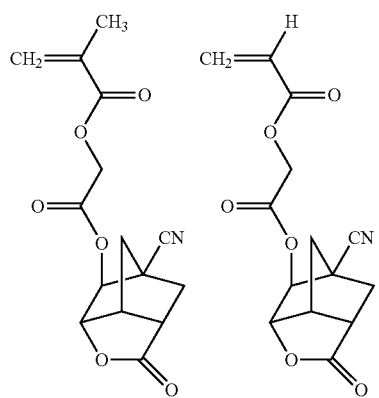
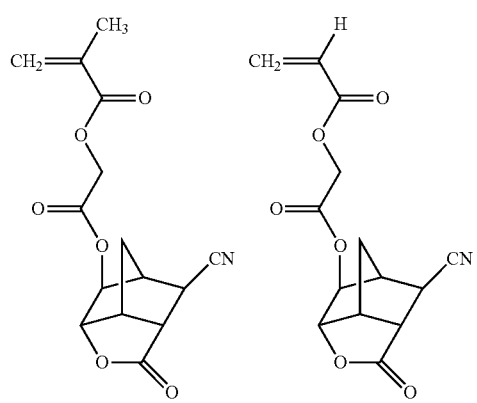
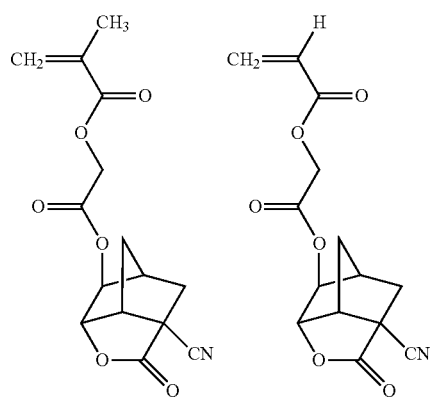
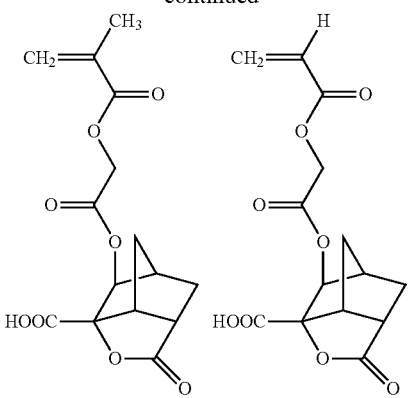
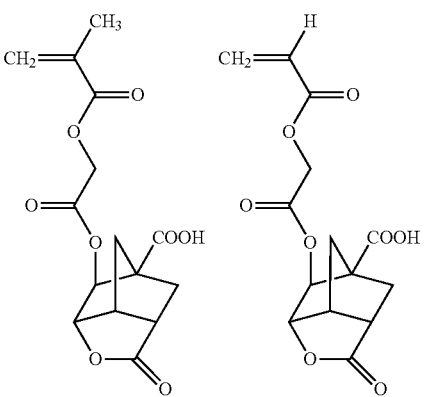
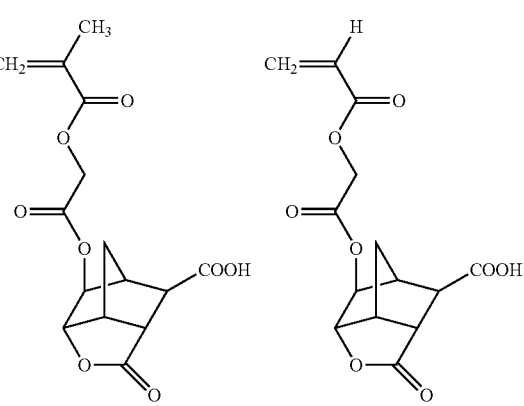
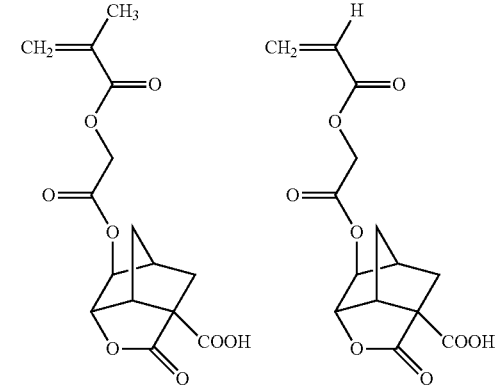
Examples of the monomer represented by the formula (c-3) include the followings.

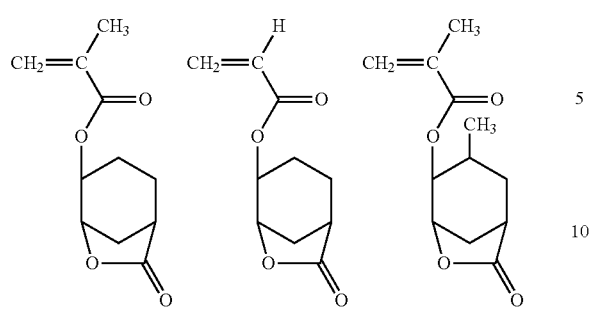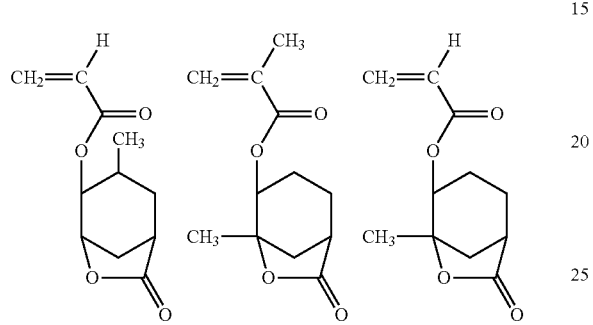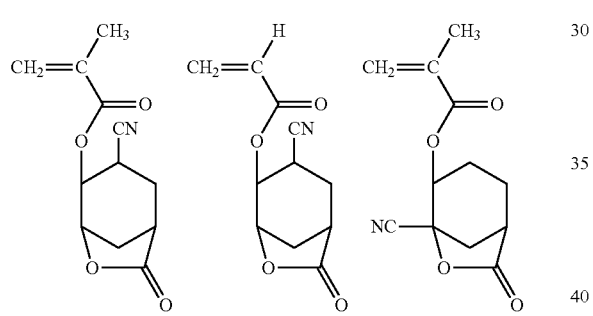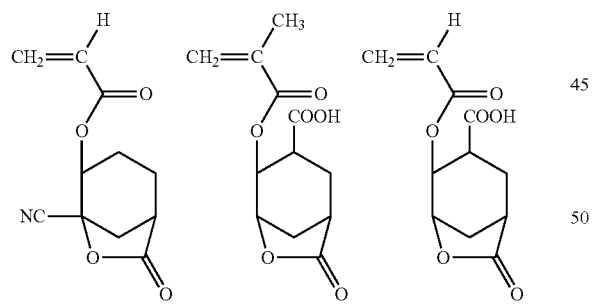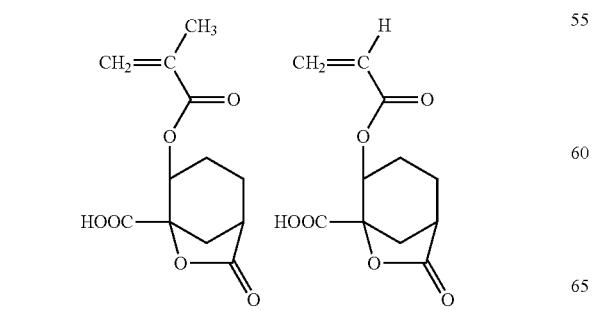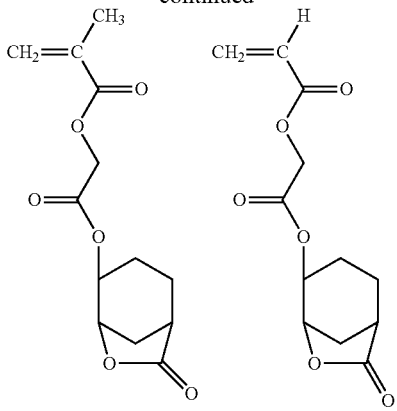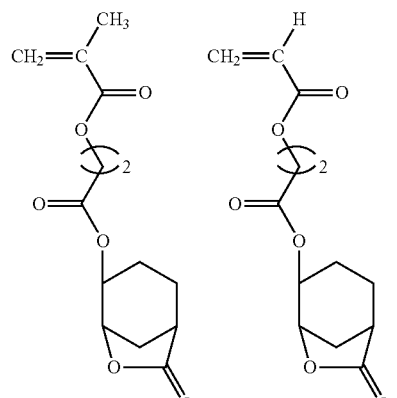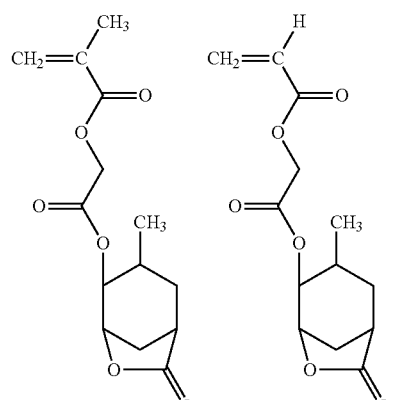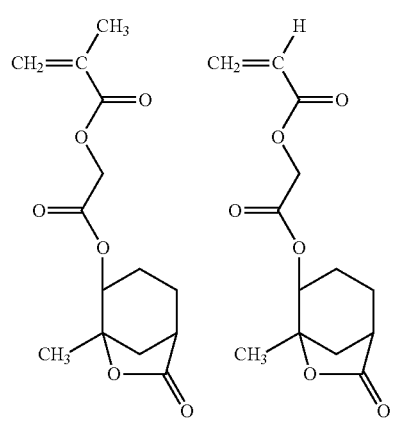

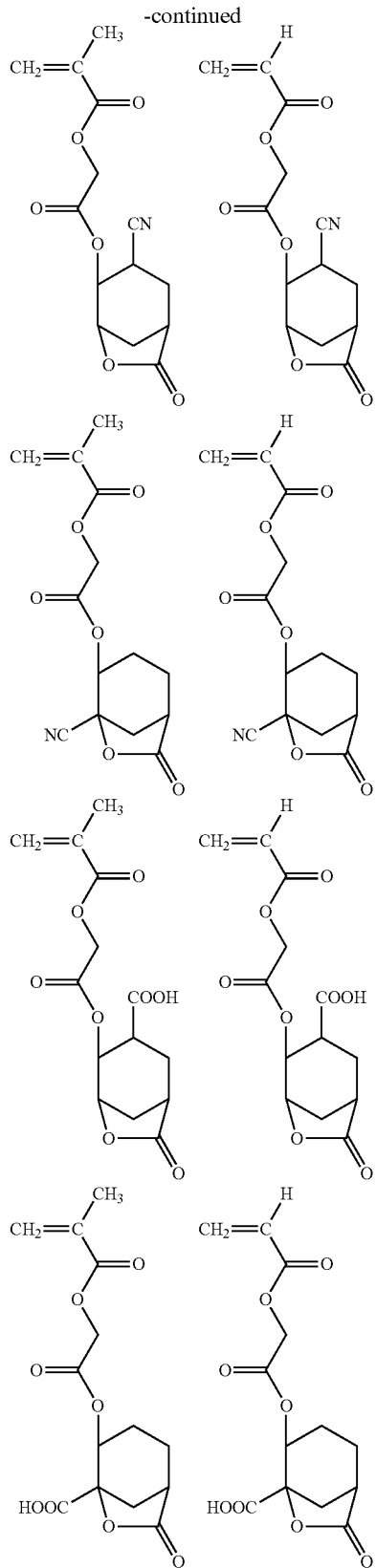

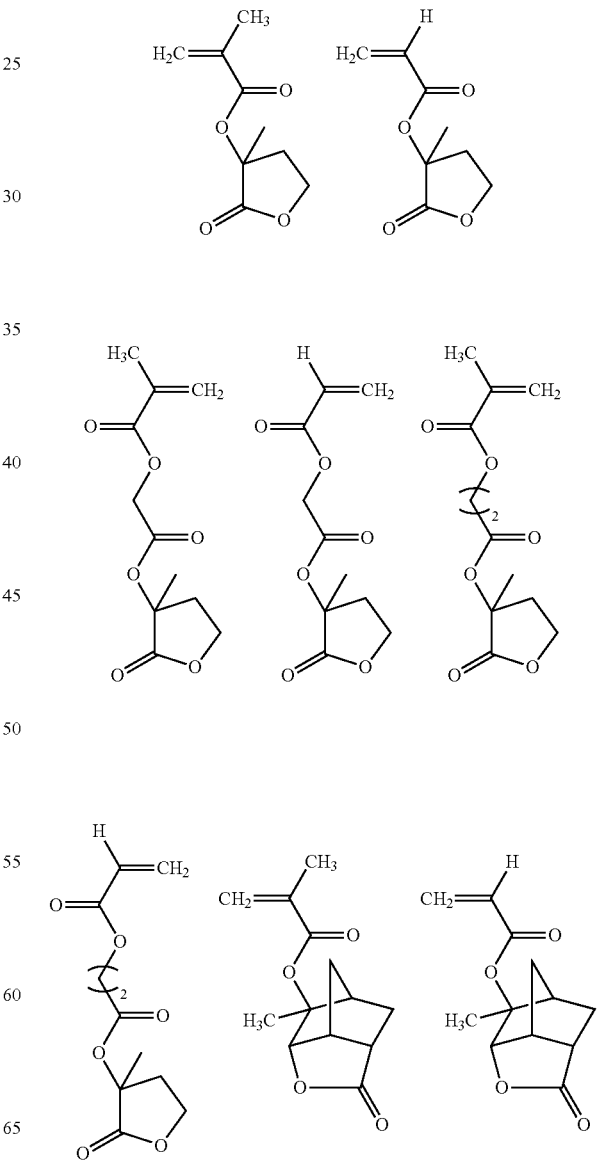

ryl acrylate, tetrahydro-2-oxo-3-furyl methacrylate, 2-(5-oxo-4-oxatricyclo[4.2.1.0$^{3,7}$]nonan-2-yloxy)-2-oxoethyl acrylate and 2-(5-oxo-4-oxatricyclo[4.2.1.0$^{3,7}$]nonan-2-yloxy)-2-oxoethyl methacrylate, and more preferred are 5-oxo-4-oxatricyclo[4.2.1.0$^{3,7}$]nonan-2-yl methacrylate, tetrahydro-2-oxo-3-furyl methacrylate and 2-(5-oxo-4-oxatricyclo[4.2.1.0$^{3,7}$]nonan-2-yloxy)-2-oxoethyl methacrylate.

When the resin contains the structural unit derived from the monomer having no acid-labile group and having a lactone ring, the content thereof is usually 5 to 50% by mole and preferably 10 to 45% by mole and more preferably 15 to 40% by mole based on total molar of all the structural units of the resin.

The resin can contain a structural unit derived from a monomer having an acid labile group containing a lactone ring. Examples of the monomer having an acid labile group containing a lactone ring include the followings.

Among them, preferred are 5-oxo-4-oxatricyclo[4.2.1.0$^{3,7}$]nonan-2-yl acrylate, 5-oxo-4-oxatricyclo[4.2.1.0$^{3,7}$]nonan-2-yl methacrylate, tetrahydro-2-oxo-3-fu-

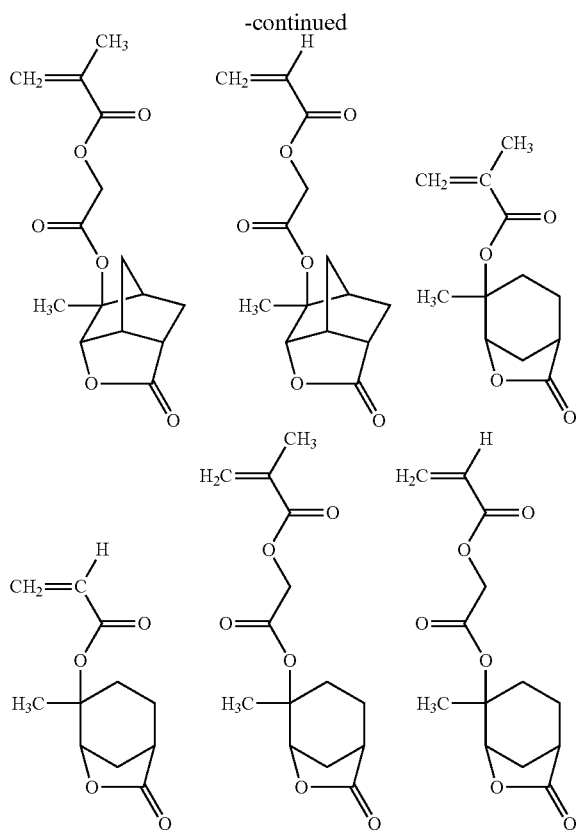

Examples of the other monomer having no acid-labile group include the monomers represented by the formulae (d-1), (d-2) and (d-3):

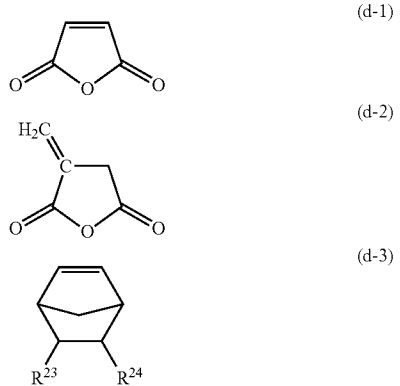

wherein $R^{23}$ and $R^{24}$ independently represents a hydrogen atom, a C1-C3 aliphatic hydrocarbon group which can have one or more substituents, a carboxyl group, a cyano group or a —COOR$^{25}$ group in which $R^{25}$ represents a C1-C36 aliphatic hydrocarbon group or a C3-C36 saturated cyclic hydrocarbon group, and one or more —CH$_2$— in the C1-C36 aliphatic hydrocarbon group and the C3-C36 saturated cyclic hydrocarbon group can be replaced by —O— or —CO—, with the proviso that the carbon atom bonded to —O— of R$^{25}$ of —COOR$^{25}$ is not a tertiary carbon atom, or $R^{23}$ and $R^{24}$ are bonded together to form a carboxylic anhydride residue represented by —C(=O)OC(=O)—.

Examples of the substituent of the C1-C3 aliphatic hydrocarbon group include a hydroxyl group. Examples of the C1-C3 aliphatic hydrocarbon group which can have one or more substituents include a C1-C3 alkyl group such as a methyl group, an ethyl group and a propyl group, and a C1-C3 hydroxyalkyl group such a hydroxymethyl group and a 2-hydroxyethyl group. The C1-C36 aliphatic hydrocarbon group represented by $R^5$ is preferably a C1-C8 aliphatic hydrocarbon group and is more preferably a C1-C6 aliphatic hydrocarbon group. The C3-C36 saturated cyclic hydrocarbon group represented by $R^{25}$ is preferably a C4-C36 saturated cyclic hydrocarbon group, and is more preferably C4-C12 saturated cyclic hydrocarbon group. Examples of $R^{25}$ include a methyl group, an ethyl group, a propyl group, a 2-oxo-oxolan-3-yl group and a 2-oxo-oxolan-4-yl group.

Examples of the monomer represented by the formula (d-3) include 2-norbornene, 2-hydroxy-5-norbornene, 5-norbornene-2-carboxylic acid, methyl 5-norbornene-2-carboxylate, 2-hydroxyethyl 5-norbornene-2,3-dicarboxylic anhydride.

When the resin contains a structural unit derived from a monomer represented by the formula (d-1), (d-2) or (d-3), the content thereof is usually 2 to 40% by mole and preferably 3 to 30% by mole and more preferably 5 to 20% by mole based on total molar of all the structural units of the resin.

Preferable resin is a resin containing the structural units derived from the monomer having an acid-labile group, and the structural units derived from the monomer having one or more hydroxyl groups and/or the monomer having a lactone ring. The monomer having an acid-labile group is preferably the monomer represented by the formula (a-1) or the monomer represented by the formula (a-2), and is more preferably the monomer represented by the formula (a-1). The monomer having one or more hydroxyl groups is preferably the monomer represented by the formula (b-1), and the monomer having a lactone ring is preferably the monomer represented by the formula (c-1) or (c-2).

The resin can be produced according to known polymerization methods such as radical polymerization.

The resin usually has 2,500 or more of the weight-average molecular weight, and preferably 3,000 or more of the weight-average molecular weight. The resin usually has 50,000 or less of the weight-average molecular weight, and preferably has 30,000 or less of the weight-average molecular weight. The weight-average molecular weight can be measured with gel permeation chromatography.

The content of the resin is usually 80% by weight or more in the solid component. In this specification, "solid component" means components other than solvents in the photoresist composition. The content of the solid component can be analyzed with conventional means such as liquid chromatography and gas chromatography.

The photoresist composition of the present invention can contain a basic compound as a quencher.

The basic compound is preferably a basic nitrogen-containing organic compound, and examples thereof include an amine compound such as an aliphatic amine and an aromatic amine and an ammonium salt. Examples of the aliphatic amine include a primary amine, a secondary amine and a tertiary amine. Examples of the aromatic amine include an aromatic amine in which aromatic ring has one or more amino groups such as aniline and a heteroaromatic amine such as pyridine. Preferable examples thereof include an aromatic amine represented by the formula (C2):

(C2) 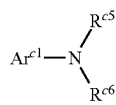

wherein $Ar^{c1}$ represents an aromatic hydrocarbon group, and $R^{c5}$ and $R^{c6}$ each independently represent a hydrogen atom, an aliphatic hydrocarbon group, a saturated cyclic hydrocarbon group or an aromatic hydrocarbon group, and the aliphatic hydrocarbon group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group.

The aliphatic hydrocarbon group is preferably an alkyl group and the saturated cyclic hydrocarbon group is preferably a cycloalkyl group. The aliphatic hydrocarbon group preferably has 1 to 6 carbon atoms. The saturated cyclic hydrocarbon group preferably has 5 to 10 carbon atoms. The aromatic hydrocarbon group preferably has 6 to 10 carbon atoms.

As the aromatic amine represented by the formula (C2), an amine represented by the formula (C2-1):

(C2-1) 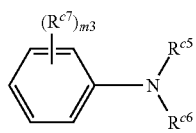

wherein $R^{c5}$ and $R^{c6}$ are the same as defined above, and $R^{c7}$ is independently in each occurrence an aliphatic hydrocarbon group, an alkoxy group, a saturated cyclic hydrocarbon group or an aromatic hydrocarbon group, and the aliphatic hydrocarbon group, the alkoxy group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, and m3 represents an integer of 0 to 3, is preferable. The aliphatic hydrocarbon group is preferably an alkyl group and the saturated cyclic hydrocarbon group is preferably a cycloalkyl group. The aliphatic hydrocarbon group preferably has 1 to 6 carbon atoms. The saturated cyclic hydrocarbon group preferably has 5 to 10 carbon atoms. The aromatic hydrocarbon group preferably has 6 to 10 carbon atoms. The alkoxy group preferably has 1 to 6 carbon atoms.

Examples of the aromatic amine represented by the formula (C2) include 1-naphthylamine, 2-naphthylamine, aniline, diisopropylaniline, 2-methylaniline, 3-methylaniline, 4-methylaniline, 4-nitroaniline, N-methylaniline, N,N-dimethylaniline, and diphenylamine, and among them, preferred is diisopropylaniline and more preferred is 2,6-diisopropylaniline.

Other examples of the basic compound include amines represented by the formulae (C3) to (C11):

(C3) 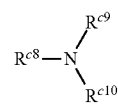

(C4) 

(C5) 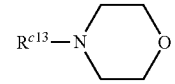

(C6) 

(C7) 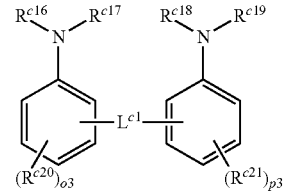

(C8) 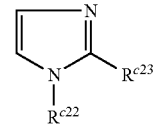

(C9) 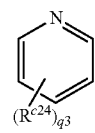

(C10) 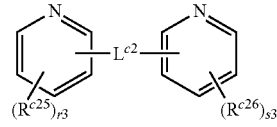

(C11) 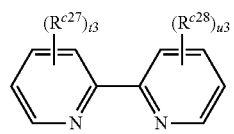

wherein $R^{c8}$, $R^{c20}$, $R^{c21}$, and $R^{c23}$ to $R^{c28}$ each independently represent an aliphatic hydrocarbon group, an alkoxy group, a saturated cyclic hydrocarbon group or an aromatic hydrocarbon group, and the aliphatic hydrocarbon group, the alkoxy group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, $R^{c9}$, $R^{c10}$, $R^{c11}$ to $R^{c14}$, $R^{c16}$ to $R^{c19}$, and $R^{c22}$ each independently represents a hydrogen atom, an aliphatic hydrocarbon group, a saturated cyclic hydrocarbon group or an aromatic hydrocarbon group, and the aliphatic hydrocarbon group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, $R^{c15}$ is independently in each occurrence an aliphatic hydrocarbon group, a saturated cyclic hydrocarbon group or an alkanoyl group, $L^{c1}$ and $L^{c2}$ each independently represents a divalent aliphatic hydrocarbon group, —CO—, —C(=NH)—, —C(=NR$^{c3}$)—, —S—, —S—S— or a combination thereof and $R^{c3}$ represents a C1-C4 alkyl group, O3 to u3 each independently represents an integer of 0 to 3 and n3 represents an integer of 0 to 8.

The aliphatic hydrocarbon group has preferably 1 to 6 carbon atoms, and the saturated cyclic hydrocarbon group has preferably 3 to 6 carbon atoms, and the alkanoyl group has preferably 2 to 6 carbon atoms, and the divalent aliphatic hydrocarbon group has preferably 1 to 6 carbon atoms. The divalent aliphatic hydrocarbon group is preferably an alkylene group.

Examples of the amine represented by the formula (C3) include hexylamine, heptylamine, octylamine, nonylamine, decylamine, dibutylamine, dipentylamine, dihexylamine, diheptylamine, dioctylamine, dinonylamine, didecylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethydiheptylamine, ethyldioctylamine, ethyldinonylamine, ethyldidecylamine, dicyclohexylmethylamine, tris[2-(2-methoxyethoxy)ethyl]amine, triisopropanolamine, ethylenediamine, tetramethylenediamine, hexamethylenediamine, 4,4'-diamino-1,2-diphenylethane, 4,4'-diamino-3,3'-dimethyldiphenylmethane and 4,4'-diamino-3,3'-diethyldiphenylmethane.

Examples of the amine represented by the formula (C4) include piperazine. Examples of the amine represented by the formula (C5) include morpholine. Examples of the amine represented by the formula (C6) include piperidine and hindered amine compounds having a piperidine skeleton as disclosed in JP 11-52575 A. Examples of the amine represented by the formula (C7) include 2,2'-methylenebisaniline. Examples of the amine represented by the formula (C8) include imidazole and 4-methylimidazole . Examples of the amine represented by the formula (C9) include pyridine and 4-methylpyridine. Examples of the amine represented by the formula (C10) include di-2-pyridyl ketone, 1,2-di(2-pyridyl) ethane, 1,2-di(4-pyridyl)ethane, 1,3-di(4-pyridyl)propane, 1,2-bis(2-pyridyl)ethene, 1,2-bis(4-pyridyl)ethene, 1,2-di(4-pyridyloxy)ethane, 4,4'-dipyridyl sulfide, 4,4'-dipyridyl disulfide, 2,2'-dipyridylamine and 2,2'-dipicolylamine. Examples of the amine represented by the formula (C11) include bipyridine.

Examples of the quaternary ammonium hydroxide include tetramethylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl)trimethylammonium hydroxide (so-called "choline").

When the basic compound is used, the amount of the basic compound is usually 0.01 to 1 parts by weight per 100 parts by weight of solid component.

The photoresist composition of the present invention usually contains one or more solvents. Examples of the solvent include a glycol ether ester such as ethyl cellosolve acetate, methyl cellosolve acetate and propylene glycol monomethyl ether acetate; a glycol ether such as propylene glycol monomethyl ether; an acyclic ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone.

The amount of the solvent is usually 90% by weight or more, preferably 92% by weight or more preferably 94% by weight or more based on total amount of the photoresist composition of the present invention. The amount of the solvent is usually 99.9% by weight or less and preferably 99% by weight or less based on total amount of the photoresist composition of the present invention.

The photoresist composition of the present invention can contain, if necessary, a small amount of various additives such as a sensitizer, a dissolution inhibitor, other polymers, a surfactant, a stabilizer and a dye as long as the effect of the present invention is not prevented.

The photoresist composition of the present invention is useful for a chemically amplified photoresist composition.

A photoresist pattern can be produced by the following steps (1) to (5):

(1) a step of applying the photoresist composition of the present invention on a substrate, (2) a step of forming a photoresist film by conducting drying, (3) a step of exposing the photoresist film to radiation, (4) a step of baking the exposed photoresist film, and (5) a step of developing the baked photoresist film with an alkaline developer, thereby forming a photoresist pattern.

The applying of the photoresist composition on a substrate is usually conducted using a conventional apparatus such as spin coater. The photoresist composition is preferably filtrated with filter having 0.2 μm of a pore size before applying. Examples of the substrate include a silicon wafer or a quartz wafer on which a sensor, a circuit, a transistor or the like is formed.

The formation of the photoresist film is usually conducted using a heating apparatus such as hot plate or a decompressor, and the heating temperature is usually 50 to 200° C., and the operation pressure is usually 1 to $1.0*10^5$ Pa.

The photoresist film obtained is exposed to radiation using an exposure system. The exposure is usually conducted through a mask having a pattern corresponding to the desired photoresist pattern. Examples of the exposure source include a light source radiating laser light in a UV-region such as a KrF excimer laser (wavelength: 248 nm), an ArF excimer laser (wavelength: 193 nm) and a $F_2$ laser (wavelength: 157 nm), and a light source radiating harmonic laser light in a far UV region or a vacuum UV region by wavelength conversion of laser light from a solid laser light source (such as YAG or semiconductor laser).

The temperature of baking of the exposed photoresist film is usually 50 to 200° C., and preferably 70 to 150° C.

The development of the baked photoresist film is usually carried out using a development apparatus. The alkaline developer used may be any one of various alkaline aqueous solution used in the art. Generally, an aqueous solution of tetramethylammonium hydroxide or (2-hydroxyethyl)trimethylammoniumhydroxide (commonly known as "choline") is often used. After development, the photoresist pattern formed is preferably washed with ultrapure water, and the remained water on the photoresist pattern and the substrate is preferably removed.

The photoresist composition of the present invention is suitable for ArF excimer laser lithography, KrF excimer laser lithography, ArF immersion lithography, EUV (extreme ultraviolet) lithography, EUV immersion lithography and EB (electron beam) lithography. Further, the photoresist composition of the present invention can especially be used for ArF immersion lithography, EUV lithography and EB lithography. Furthermore, the photoresist composition of the present invention can also be used in double imaging.

EXAMPLES

The present invention will be described more specifically by Examples, which are not construed to limit the scope of the present invention.

The "%" and "part(s)" used to represent the content of any component and the amount of any material used in the following examples and comparative examples are on a weight basis unless otherwise specifically noted. The weight-average molecular weight of any material used in the following examples is a value found by gel permeation chromatography [HLC-8120GPC Type, Column (Three Columns with guard column): TSKgel Multipore HXL-M, manufactured by TOSOH CORPORATION, Solvent: tetrahydrofuran, Flow rate: 1.0 mL/min., Detector: RI detector, Column temperature: 40° C., Injection volume: 100 µL] using standard polystyrene as a standard reference material available from TOSOH CORPORATION.

Example 1

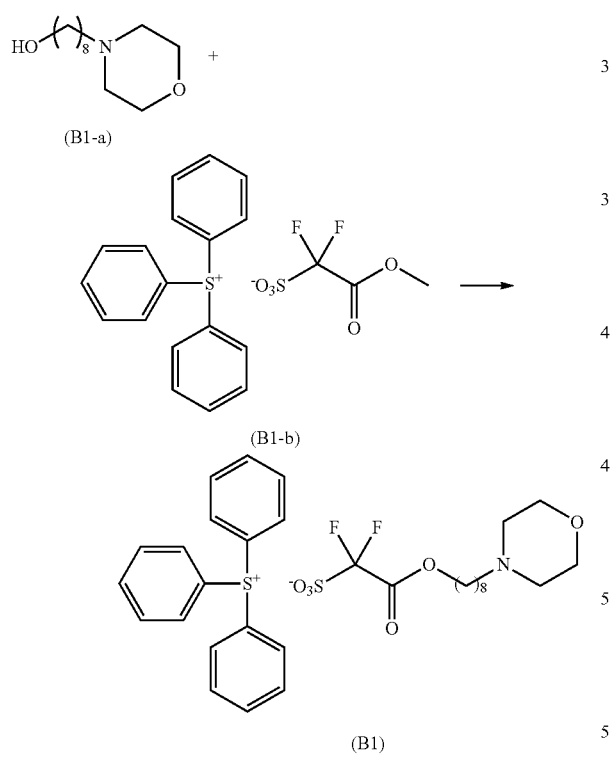

The salt represented by the formula (B1-b) was synthesized according to the method described in JP 2008-13551 A.

A mixture of 10.00 parts of the compound represented by the formula (B1-b), 60.00 parts of chloroform, 5.71 parts of a compound represented by the formula (B1-a), 14.00 parts of molecular sieves (Molecular Sieves 5A available from Wako Pure Chemical Industries, Ltd.) and 0.33 part of lithium amide was refluxed at 80° C. for 24 hours. The obtained reaction mixture was filtrated. To the filtrate obtained, 15 parts of 3.6% aqueous oxalic acid solution was added, and the resultant mixture was mixed and then, separated. The organic layer obtained was washed with 15 parts of ion-exchanged water. The organic layer obtained was washed six times with water. To the organic layer, 1.00 part of active carbon was added to stir at 23° C. for 30 minutes followed by filtration. The filtrate obtained was concentrated, and to the residue obtained, 100 parts of acetonitrile was added to prepare a solution. The solution obtained was concentrated, and 200 parts of tert-butyl methyl ether was added to the residue obtained. The resultant mixture was stirred for 30 minutes and then filtrated to obtain 6.64 parts of a salt represented by the formula (B1). This is called as Salt B1.

MS (ESI(+) Spectrum): M$^+$ 263.1
MS (ESI(−) Spectrum): M$^-$ 372.1

Example 2

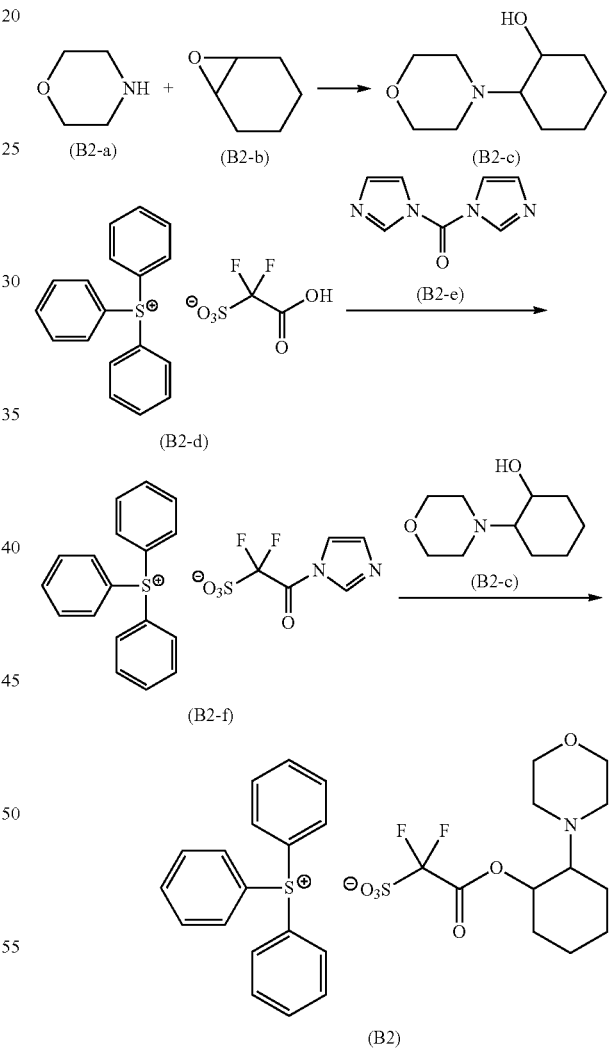

A mixture of 46.6 parts of a compound represented by the formula (B2-a), 27.54 parts of ion-exchanged water and 50.00 parts of a compound represented by the formula (B2-b) was refluxed at 105° C. for 2 hours. The reaction mixture obtained was cooled down to 23° C., and 450 parts of saturated aqueous sodium hydroxide solution and 400 parts of tert-butyl methyl ether were added thereto. The resultant mixture was mixed and then, separated. The organic layer obtained was mixed with 5.00 parts of magnesium sulfate, and the resultant mixture was stirred at 23° C. for 30 minutes. The mixture obtained was filtrated and the filtrate obtained was distillated under reduced pressure. The fraction of which boiling point was 104 to 107° C. at 2 to 3 mmHg was isolated to obtain 62.69 parts of a compound represented by the formula (B2-c).

The salt represented by the formula (B2-d) was synthesized according to the method described in JP 2008-127367 A.

A mixture of 10.00 parts of the salt represented by the formula (B2-d) and 60.00 parts of acetonitrile was stirred at 40° C. for 30 minutes. To the mixture obtained, 4.34 parts of a compound represented by the formula (B2-e) was added. The resultant mixture was stirred at 50° C. for 2 hours. The mixture obtained was cooled down to 23° C., and then, filtrated to obtain a solution containing a compound represented by the formula (B2-f).

A mixture of 3.78 parts of the compound represented by the formula (B2-c) and 7.57 parts of chloroform was stirred at 23° C. for 1 hour. To the mixture obtained, the solution containing a compound represented by the formula (B2-f) was added. The resultant mixture was stirred at 23° C. for 1 hour. The mixture obtained was concentrated, and 60 parts of chloroform and 30 parts of ion-exchanged water were added to the residue obtained. The resultant mixture was mixed and then, separated. The organic layer was washed six times with water. To the organic layer, 1.00 part of active carbon was added to stir at 23° C. for 30 minutes followed by filtration. The filtrate obtained was concentrated, and to the residue obtained, 100 parts of acetonitrile was added to prepare a solution. The solution obtained was concentrated, and 200 parts of tert-butyl methyl ether was added to the residue obtained. The resultant mixture was stirred for 30 minutes and then filtrated to obtain 6.03 parts of a salt represented by the formula (B2). This is called as Salt B2.

MS (ESI(+) Spectrum): M$^+$ 263.1
MS (ESI(−) Spectrum): M$^-$ 342.1

Example 3

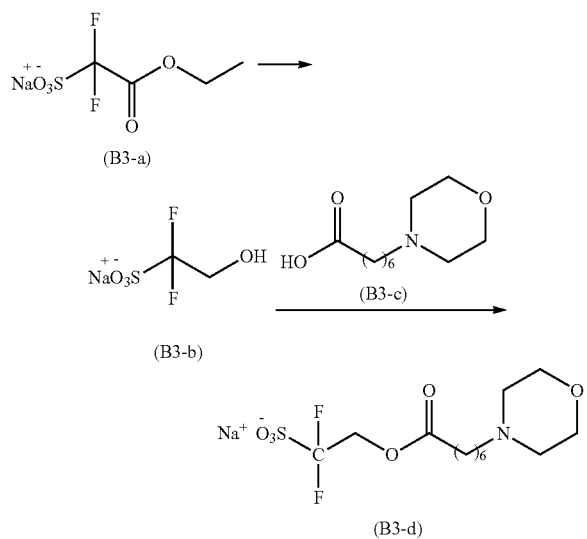

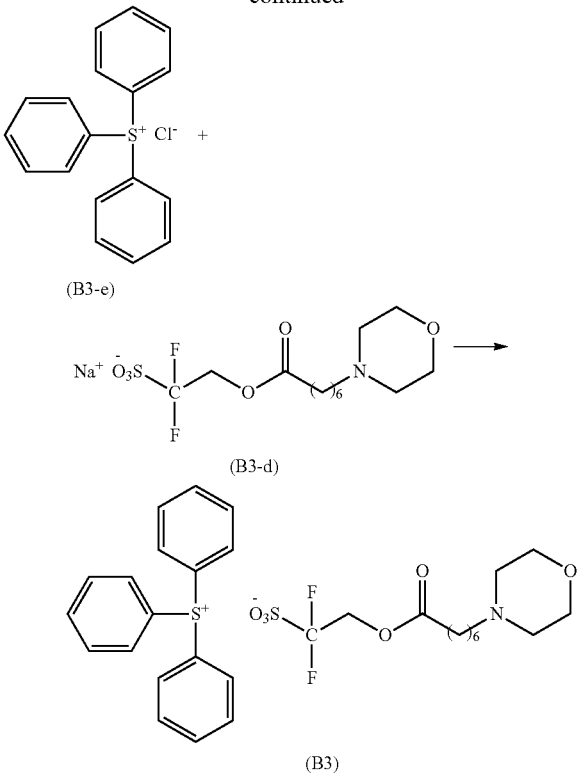

A mixture of 10.4 parts of lithium amide and 120 parts of tetrahydrofuran was stirred at 23° C. for 30 minutes. To the mixture, a solution prepared by dissolving 62.2 parts of the salt represented by the formula (B3-a) in 900 parts of anhydrous tetrahydrofuran was added dropwise under cooling with ice bath. The resultant mixture was stirred at 23° C. for 5 hours. To the reaction mixture obtained, 50.0 parts of ethyl acetate and 50.00 parts of 6N hydrochloric acid were added. The mixture obtained was stirred and then, separated. The organic layer obtained was concentrated and the residue obtained was purified with silica gel column chromatography (silica gel: silica gel 60-200 mesh available from Merck KGaA, solvent: chloroform/methanol=5/1) to obtain 84.7 parts of a salt represented by the formula (B3-b) of which purity was 60%.

A mixture of 3.85 parts of a compound represented by the formula (B3-c) and 75 parts of anhydrous tetrahydrofuran was stirred at 23° C. for 30 minutes. To the mixture, a solution prepared by mixing 2.89 parts of carbonyldiimidazole with 50 parts of anhydrous tetrahydrofuran was added dropwise at 23° C., and the resultant mixture was stirred at 23° C. for 4 hours. The reaction mixture obtained was added dropwise into a mixture of 6.04 parts of a salt represented by the formula (B3-b) and 50 parts of anhydrous tetrahydrofuran over 25 minutes at 65° C. The resultant mixture was stirred at 65° C. for 18 hours. The reaction mixture obtained was cooled and then, filtrated. The filtrate obtained was concentrated and the residue obtained was purified with silica gel column chromatography (silica gel: silica gel 60-200 mesh available from Merck KGaA, solvent: chloroform/methanol=5/1) to obtain 2.58 parts of a salt represented by the formula (B3-d).

To a solution containing 1.27 parts of the salt represented by the formula (B3-d), 5.00 parts of chloroform and 1.00 part of the salt represented by the formula (B3-e) were added. The resultant mixture was stirred at 23° C. for 15 hours. The mixture obtained was washed with ion-exchanged water. To the mixture, 1.00 part of active carbon was added to stir followed by filtration. The filtrate obtained was concentrated, and to the residue obtained, 10 parts of ethyl acetate was added. The resultant mixture was stirred and then, the supernatant solution was removed from the mixture. To the residue obtained, 10 parts of tert-butyl methyl ether was added. The resultant mixture was stirred and then, the supernatant solution was removed from the mixture. The obtained residue was dissolved in chloroform, and the solution obtained was concentrated to obtain 1.82 parts of a salt represented by the formula (B3). This is called as Salt B3.

MS (ESI(+) Spectrum): M⁺ 263.1
MS (ESI(−) Spectrum): M⁻ 358.1

Example 4

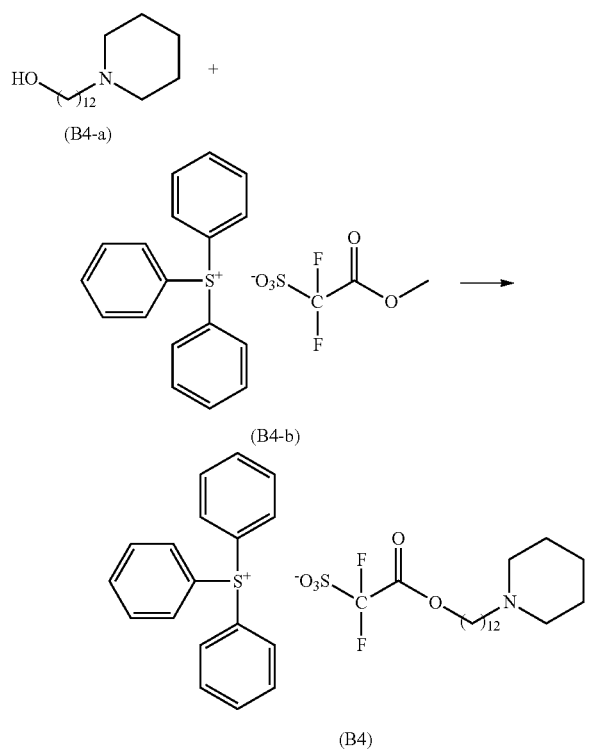

(B4)

A mixture of 10.00 parts of the salt represented by the formula (B4-b), 60.00 parts of chloroform, 7.15 parts of a compound represented by the formula (B4-a), 14.00 parts of molecular sieves (Molecular Sieves 5A available from Wako Pure Chemical Industries, Ltd.) and 0.33 part of lithium amide was refluxed at 80° C. for 24 hours. The obtained reaction mixture was filtered. To the filtrate obtained, 15 parts of 3.6% aqueous oxalic acid solution was added, and the resultant mixture was mixed and then, separated. The organic layer obtained was washed with 15 parts of ion-exchanged water. The organic layer obtained was washed five times with water. To the organic layer, 1.00 part of active carbon was added to stir at 23° C. for 30 minutes followed by filtration. The filtrate obtained was concentrated, and to the residue obtained, 100 parts of ethyl acetate was added. The resultant mixture was stirred and then, the supernatant solution was removed from the mixture. To the residue obtained, 100 parts of tert-butyl methyl ether was added. The resultant mixture was stirred and then, the supernatant solution was removed from the mixture. The obtained residue was dissolved in chloroform, and the solution obtained was concentrated to obtain 5.29 parts of a salt represented by the formula (B4). This is called as Salt B4.

MS (ESI(+) Spectrum): M⁺ 263.1
MS (ESI(−) Spectrum): M⁻ 426.2

Example 5

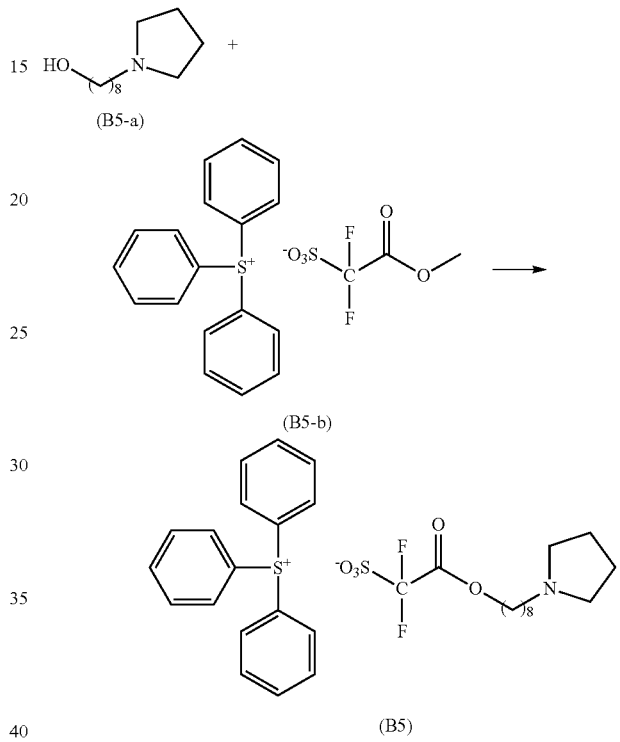

(B5)

A mixture of 10.00 parts of the salt represented by the formula (B5-b), 60.00 parts of chloroform, 5.29 parts of a compound represented by the formula (B5-a), 14.00 parts of molecular sieves (Molecular Sieves 5A available from Wako Pure Chemical Industries, Ltd.) and 0.33 part of lithium amide was refluxed at 80° C. for 24 hours. The obtained reaction mixture was filtered. To the filtrate obtained, 15 parts of 3.6% aqueous oxalic, acid solution was added, and the resultant mixture was mixed and then, separated. The organic layer obtained was washed with 15 parts of ion-exchanged water. The organic layer obtained was washed five times with water. To the organic layer, 1.00 part of active carbon was added to stir at 23° C. for 30 minutes followed by filtration. The filtrate obtained was concentrated, and to the residue obtained, 100 parts of ethyl acetate was added. The resultant mixture was stirred and then, the supernatant solution was removed from the mixture. To the residue obtained, 100 parts of tert-butyl methyl ether was added. The resultant mixture was stirred and then, the supernatant solution was removed from the mixture. The obtained residue was dissolved in chloroform, and the solution obtained was concentrated to obtain 4.19 parts of a salt represented by the formula (B5). This is called as Salt B5.

MS (ESI(+) Spectrum): M⁺ 263.1
MS (ESI(−) Spectrum): M⁻ 356.1

Example 6

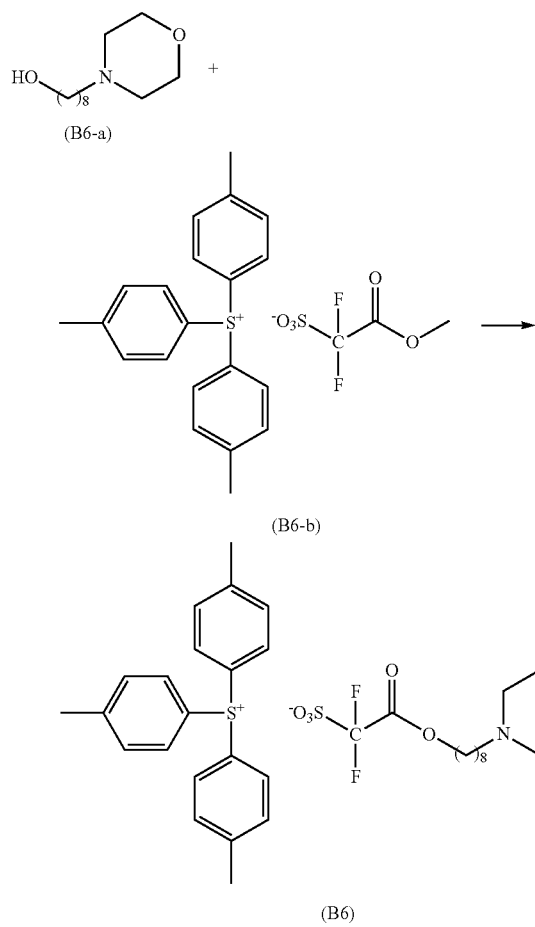

A mixture of 10.93 parts of the salt represented by the formula (B6-b), 60.00 parts of chloroform, 5.71 parts of a compound represented by the formula (B6-a), 14.00 parts of molecular sieves (Molecular Sieves 5A available from Wako Pure Chemical Industries, Ltd.) and 0.33 part of lithium amide was refluxed at 80° C. for 24 hours . The reaction mixture obtained was filtrated. To the filtrate obtained, 15 parts of 3.6% aqueous oxalic acid solution was added, and the resultant mixture was mixed and then, separated. The organic layer obtained was washed with 15 parts of ion-exchanged water. The organic layer obtained was washed six times with water. To the organic layer, 1.00 part of active carbon was added to stir at 23° C. for 30 minutes followed by filtration. The filtrate obtained was concentrated, and to the residue obtained, 100 parts of acetonitrile was added to prepare a solution. The solution obtained was concentrated. To the residue obtained, 200 parts of tert-butyl methyl ether was added. The resultant mixture was stirred for 30 minutes and then, filtrated to obtain 6.72 parts of a salt represented by the formula (B6). This is called as Salt B6.

MS (ESI(+) Spectrum): M$^+$ 305.1
MS (ESI(−) Spectrum): M$^-$ 372.1

Example 7

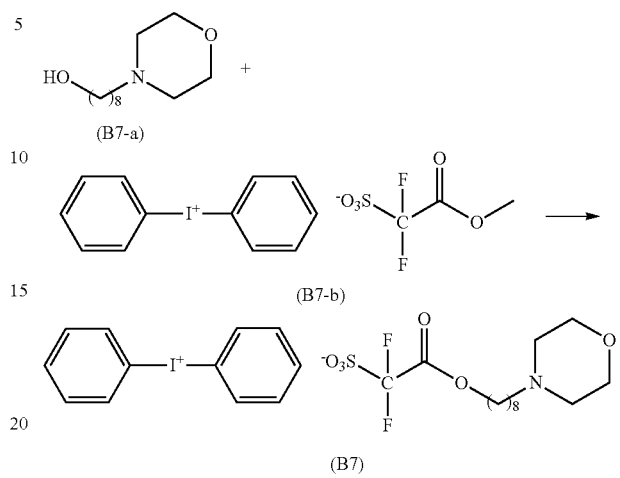

A mixture of 10.39 parts of the salt represented by the formula (B7-b), 60.00 parts of chloroform, 5.71 parts of a compound represented by the formula (B7-a), 14.00 parts of molecular sieves (Molecular Sieves 5A available from Wako Pure Chemical Industries, Ltd.) and 0.33 part of lithium amide was refluxed at 80° C. for 24 hours. The reaction mixture obtained was filtrated. To the filtrate obtained, 15 parts of 3.6% aqueous oxalic acid solution was added, and the resultant mixture was mixed and then, separated. The organic layer obtained was washed with 15 parts of ion-exchanged water. The organic layer obtained was washed six times with water. To the organic layer, 1.00 part of active carbon was added to stir at 23° C. for 30 minutes followed by filtration. The filtrate obtained was concentrated, and to the residue obtained, 100 parts of ethyl acetate was added. The resultant mixture was stirred and then, the supernatant solution was removed from the mixture. The residue obtained was dissolved in chloroform. The solution obtained was concentrated and the residue obtained was purified with silica gel column chromatography (silica gel: silica gel 60-200 mesh available from Merck KGaA, solvent: chloroform/methanol=5/1) to obtain 4.88 parts of a salt represented by the formula (B7). This is called as Salt B7.

MS (ESI(+) Spectrum): M$^+$ 281.0
MS (ESI(−) Spectrum): M$^-$ 372.1

Example 8

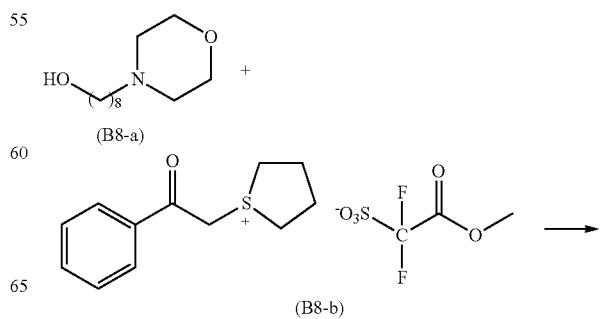

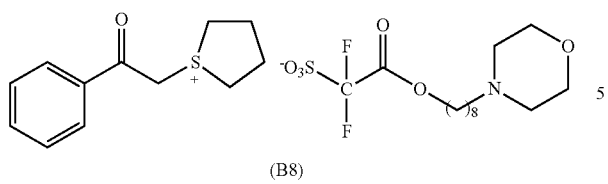

(B8)

A mixture of 8.76 parts of the salt represented by the formula (B8-b), 60.00 parts of chloroform, 5.71 parts of a compound represented by the formula (B8-a), 14.00 parts of molecular sieves (Molecular Sieves 5A available from Wako Pure Chemical Industries, Ltd.) and 0.33 part of lithium amide was refluxed at 80° C. for 24 hours. The reaction mixture obtained was filtrated. To the filtrate obtained, 15 parts of 3.6% aqueous oxalic acid solution was added, and the resultant mixture was mixed and then, separated. The organic layer obtained was washed with 15 parts of ion-exchanged water. The organic layer obtained was washed six times with water. To the organic layer, 1.00 part of active carbon was added to stir at 23° C. for 30 minutes followed by filtration. The filtrate obtained was concentrated, and to the residue obtained, 100 parts of ethyl acetate was added. The resultant mixture was stirred and then, the supernatant solution was removed from the mixture. The residue obtained was dissolved in chloroform. The solution obtained was concentrated and the residue obtained was purified with silica gel column chromatography (silica gel: silica gel 60-200 mesh available from Merck KGaA, solvent: chloroform/methanol=5/1) to obtain 2.86 parts of a salt represented by the formula (B8). This is called as Salt B8.

MS (ESI(+) Spectrum): M⁺ 207.1

MS (ESI(−) Spectrum): M⁻ 372.1

Monomers used in the following Resin Synthesis Example 1 are following monomers E, F, B, C and D.

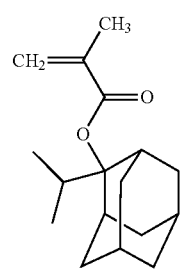

(E)

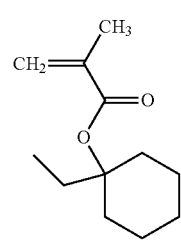

(F)

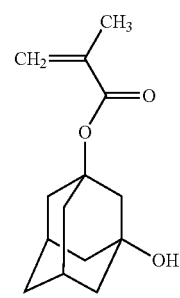

(B)

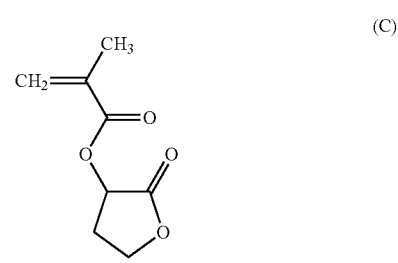

(C)

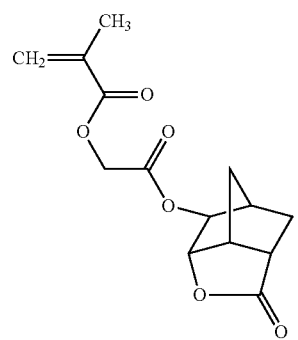

(D)

Resin Synthesis Example 1

The monomers E, F, B, C and D were mixed in a molar ratio of 30/14/6/20/30 (monomer E/monomer F/monomer B/monomer C/monomer D), and 1,4-dioxane in 1.5 times part based on total parts of all monomers was added to prepare a mixture. To the mixture, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 73° C. for about 5 hours. The reaction mixture obtained was poured into a mixture of a large amount of methanol and water (4/1) to cause precipitation, and this operation was repeated three times for purification. As a result, a resin having a weight-average molecular weight of about $8.1 \times 10^3$ was obtained in a yield of 65%. This resin is called as resin A1.

Monomers used in the following Resin Synthesis Example 2 are following monomers A, B and C.

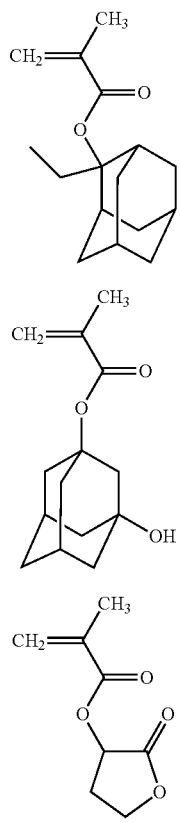

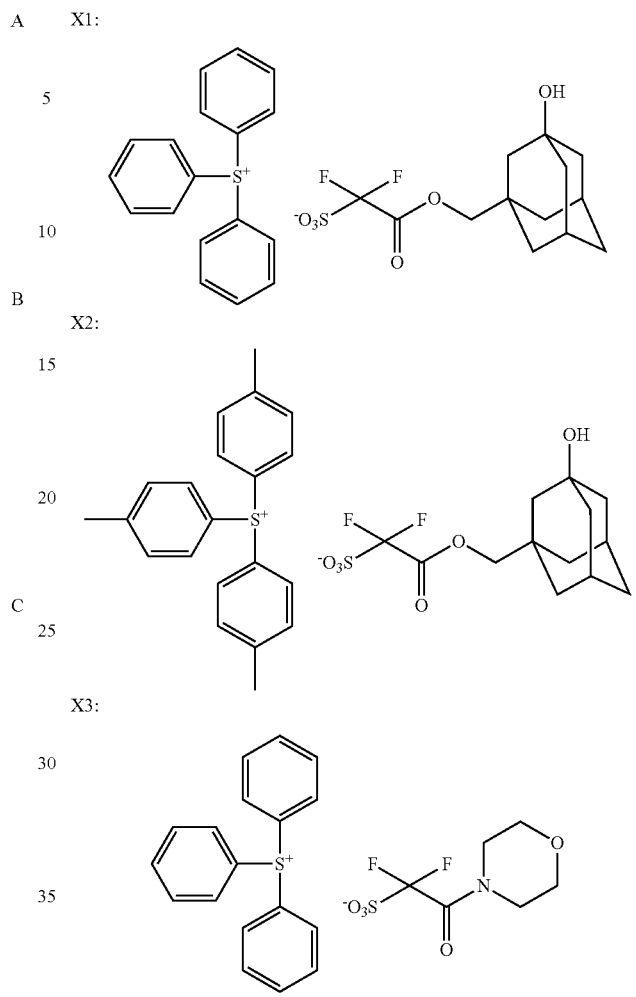

Resin Synthesis Example 2

The monomers A, B and C were mixed in a molar ratio of 50/25/25 (monomer A/monomer B/monomer C), and 1,4-dioxane in 1.5 times part based on total parts of all monomers was added to prepare a mixture. To the mixture, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 77° C. for about 5 hours. The reaction mixture obtained was poured into a mixture of a large amount of methanol and water to cause precipitation, and this operation was repeated three times for purification. As a result, a resin having a weight-average molecular weight of about $8.0 \times 10^3$ was obtained in a yield of 60%. This resin is called as resin A2.

Examples 9 to 24 and Comparative Example 1

Resin

Resin A1, A2
<Acid Generator>
Salt B1, B2, B3, B4, B5, B6, B7, B8

<Quencher>
C1: 2,6-diisopropylaniline
<Solvent>

| S1: | propylene glycol monomethyl ether acetate | 265 parts |
| | propylene glycol monomethyl ether | 20 parts |
| | 2-heptanone | 20 parts |
| | γ-butyrolactone | 3.5 parts |

The following components were mixed and dissolved, further, filtrated through a fluorine resin filter having pore diameter of 0.2 μm, to prepare photoresist compositions.
Resin (kind and amount are described in Table 1)
Acid Generator (kind and amount are described in Table 1)
Quencher (kind and amount are described in Table 1)
Solvent S1

TABLE 1

| Ex. No. | Resin (kind/amount (part)) | Acid Generator (kind/amount (part)) | Quencher (kind/amount (part)) | PB (° C.) | PEB (° C.) |
|---|---|---|---|---|---|
| Ex. 9 | A1/10 | B1/0.05 X1/0.85 | — | 100 | 100 |

TABLE 1-continued

| Ex. No. | Resin (kind/ amount (part)) | Acid Generator (kind/ amount (part)) | Quencher (kind/ amount (part)) | PB (° C.) | PEB (° C.) |
|---|---|---|---|---|---|
| Ex. 10 | A1/10 | B1/0.05 X2/0.85 | — | 100 | 100 |
| Ex. 11 | A2/10 | B1/0.05 X2/0.85 | — | 110 | 110 |
| Ex. 12 | A1/10 | B1/0.025 X2/0.85 | C1/0.07 | 100 | 100 |
| Ex. 13 | A2/10 | B1/0.025 X1/0.85 | C1/0.07 | 110 | 110 |
| Ex. 14 | A1/10 | B2/0.05 X1/0.85 | — | 100 | 100 |
| Ex. 15 | A1/10 | B2/0.05 X2/0.85 | — | 100 | 100 |
| Ex. 16 | A2/10 | B2/0.05 X2/0.85 | — | 110 | 110 |
| Ex. 17 | A1/10 | B2/0.025 X2/0.85 | C1/0.07 | 100 | 100 |
| Ex. 18 | A1/10 | B3/0.05 X2/0.85 | — | 100 | 100 |
| Ex. 19 | A1/10 | B4/0.05 X2/0.85 | — | 100 | 100 |
| Ex. 20 | A1/10 | B5/0.05 X2/0.85 | — | 100 | 100 |
| Ex. 21 | A1/10 | B6/0.05 X2/0.85 | — | 100 | 100 |
| Ex. 22 | A1/10 | B7/0.05 X2/0.85 | — | 100 | 100 |
| Ex. 23 | A1/10 | B8/0.05 X2/0.85 | — | 100 | 100 |
| Ex. 24 | A2/10 | B6/0.85 X1/0.85 | — | 110 | 110 |
| Comp. Ex. 1 | A2/10 | X3/0.05 X1/0.85 | — | 110 | 110 |

12-inch silicon wafers were each coated with "ARC-29", which is an organic anti-reflective coating composition available from Nissan Chemical Industries, Ltd., and then baked at 205° C. for 60 seconds, to form a 78 nm-thick organic anti-reflective coating. Each of the photoresist compositions prepared as above was spin-coated over the anti-reflective coating so that the thickness of the resulting film became 85 nm after drying. The silicon wafers thus coated with the respective photoresist compositions were each prebaked on a direct hotplate at a temperature shown in the column "PB" in Table 1 for 60 seconds. Using an ArF excimer stepper for immersion exposure ("XT: 1900Gi" manufactured by ASML, NA=1.35, 3/4 Annular, X-Y deflection), each wafer thus formed with the respective resist film was subjected to line and space pattern exposure, with the exposure quantity being varied stepwise.

After the exposure, each wafer was subjected to post-exposure baking on a hotplate at a temperature shown in the column "PEE" in Table 1 for 60 seconds and then to paddle development for 60 seconds with an aqueous solution of 2.38 wt % tetramethylammonium hydroxide.

Each of patterns developed on the organic anti-reflective coating substrate after the development was observed with a scanning electron microscope, the results of which are shown in Table 2.

Effective Sensitivity (ES): It was expressed as the amount of exposure that the line pattern and the space pattern of 50 nm become 1:1 after exposure and development.

Focus margin (DOF): The photoresist patterns were obtained at ES, with the focal point distance being varied stepwise. Each of patterns developed on the organic anti-reflective coating substrate after the development were observed and the focal point distances when the patterns of which line width was 47.5 nm or more and 52 . 5 nm or less were obtained were measured and the difference between the max value of the focal point distance and the minimum value of the focal point distance was calculated. When the difference is 0.15 μm or more and less than 0.17 μm, DOF is good and its evaluation is marked by "○", when the difference is 0.17 μm or more, DOF is very good and its evaluation is marked by "⊚", and when the difference is less than 0.15 μm, DOF is bad and its evaluation is marked by "X". The bigger the difference is, the better the photoresist composition is. The difference obtained was also shown in parentheses in Table 2.

TABLE 2

| Ex. No. | DOF |
|---|---|
| Ex. 9 | ⊚ (0.18 μm) |
| Ex. 10 | ⊚ (0.18 μm) |
| Ex. 11 | ○ (0.15 μm) |
| Ex. 12 | ⊚ (0.21 μm) |
| Ex. 13 | ○ (0.15 μm) |
| Ex. 14 | ⊚ (0.21 μm) |
| Ex. 15 | ⊚ (0.21 μm) |
| Ex. 16 | ○ (0.15 μm) |
| Ex. 17 | ⊚ (0.24 μm) |
| Ex. 18 | ⊚ (0.18 μm) |
| Ex. 19 | ⊚ (0.18 μm) |
| Ex. 20 | ⊚ (0.18 μm) |
| Ex. 21 | ⊚ (0.24 μm) |
| Ex. 22 | ○ (0.15 μm) |
| Ex. 23 | ○ (0.15 μm) |
| Ex. 24 | ⊚ (0.18 μm) |
| Comp. Ex. 1 | X (0.06 μm) |

12-inch silicon wafers were each coated with "ARC-29", which is an organic anti-reflective coating composition available from Nissan Chemical Industries, Ltd., and then baked at 205° C. for 60 seconds, to form a 78 nm-thick organic anti-reflective coating. Each of the photoresist compositions prepared as above was spin-coated over the anti-reflective coating so that the thickness of the resulting film became 85 nm after drying. The silicon wafers thus coated with the respective photoresist compositions were each prebaked on a direct hotplate at a temperature shown in the column -"PB" in Table 1 for 60 seconds. Using an ArF excimer stepper for immersion exposure ("XT: 1900Gi" manufactured by ASML, NA=1.35, 3/4 Annular, X-Y deflection), each wafer thus formed with the respective resist film was subjected to contact hole pattern exposure using a photomask for forming a contact hole pattern having a hole pitch of 100 nm and a hole diameter of 70 nm, with the exposure quantity being varied stepwise.

After the exposure, each wafer was subjected to post-exposure baking on a hotplate at a temperature shown in the column "PEB" in Table 1 for 60 seconds and then to paddle development for 60 seconds with an aqueous solution of 2.38 wt % tetramethylammonium hydroxide.

Each of patterns developed on the organic anti-reflective coating substrate after the development was observed with a scanning electron microscope, the results of which are shown in Table 3.

Effective Sensitivity (ES): It was expressed as the amount of exposure that the hole diameter of the contact hole pattern obtained by using a photomask for forming a contact hole pattern having a hole pitch of 100 nm and a hole diameter of 70 nm become 55 nm after exposure and development.

Focus margin (DOF): The photoresist patterns were obtained at ES, with the focal point distance being varied stepwise. Each of patterns developed on the organic anti-reflective coating substrate after the development were observed and the focal point distances when the patterns of which hole diameter was 52.2 nm or more and 57.7 nm or less were obtained were measured and the difference between the max value of the focal point distance and the minimum value of the focal point distance was calculated. When the difference is 0.15 μm or more and less than 0.17 μm, DOF is good and its evaluation is marked by "○", when the difference is 0.17 μm or more, DOF is very good and its evaluation is marked by "⊚", and when the difference is less than 0.15 μm, DOF is bad and its evaluation is marked by "X". The bigger the difference is, the better the photoresist composition is. The difference obtained was also shown in parentheses in Table 3.

TABLE 3

| Ex. No. | DOF |
|---------|-----|
| Ex. 9 | ⊚ (0.18 μm) |
| Ex. 10 | ⊚ (0.18 μm) |
| Ex. 11 | ○ (0.15 μm) |
| Ex. 12 | ⊚ (0.21 μm) |
| Ex. 13 | ○ (0.15 μm) |
| Ex. 14 | ⊚ (0.21 μm) |
| Ex. 15 | ⊚ (0.21 μm) |
| Ex. 16 | ⊚ (0.21 μm) |
| Ex. 17 | ⊚ (0.27 μm) |
| Ex. 18 | ⊚ (0.18 μm) |
| Ex. 19 | ⊚ (0.18 μm) |
| Ex. 20 | ⊚ (0.18 μm) |
| Ex. 21 | ⊚ (0.27 μm) |
| Ex. 22 | ○ (0.15 μm) |
| Ex. 23 | ⊚ (0.18 μm) |
| Ex. 24 | ⊚ (0.21 μm) |
| Comp. Ex. 1 | X (0.09 μm) |

The salt of the present invention is novel and is useful as a component of a photoresist composition, and the photoresist composition containing the salt of the present invention provides a photoresist pattern having good focus margin, and is especially suitable for ArF excimer laser lithography, KrF excimer laser lithography, ArF immersion lithography, EUV (extreme ultraviolet) lithography, EUV immersion lithography and EB (electron beam) lithography.

What is claimed is:

1. A salt represented by the formula (I):

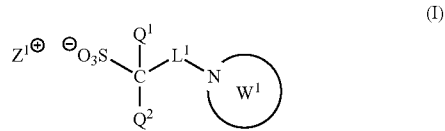

wherein $Q^1$ and $Q^2$ each independently represent a fluorine atom or a C1-C6 perfluoroalkyl group, $L^1$ represents *—CO—O—$L^a$- or *—$CH_2$—O—$L^b$-, * represents a binding position to —C($Q^1$)($Q^2$)-, $L^a$ and $L^b$ independently represent a C1-C15 divalent saturated hydrocarbon group in which one or more —$CH_2$— can be replaced by —O— or —CO—, ring $W^1$ represents a C2-C36 nitrogen-containing heterocyclic group in which one or more —$CH_2$— can be replaced by —O—, and $Z^{1\oplus}$ represents an organic counter ion.

2. The salt according to claim 1, wherein $L^1$ represents *—CO—O—$L^a$-.

3. The salt according to claim 1, wherein $Z^{1\oplus}$ is a triarylsulfonium cation.

4. An acid generator comprising the salt according to claim 1.

5. A photoresist composition comprising the acid generator according to claim 4 and a resin.

6. The photoresist composition according to claim 5, wherein the resin comprises a structural unit having an acid-labile group, being insoluble or poorly soluble in an aqueous alkali solution but becoming soluble in an aqueous alkali solution by the action of an acid.

7. The photoresist composition according to claim 5 or 6, which further contains a basic compound.

8. A process for producing a photoresist pattern comprising the following steps (1) to (5):
  (1) a step of applying the photoresist composition according to claim 5 or 6 on a substrate,
  (2) a step of forming a photoresist film by conducting drying,
  (3) a step of exposing the photoresist film to radiation,
  (4) a step of baking the exposed photoresist film, and
  (5) a step of developing the baked photoresist film with an alkaline developer, thereby forming a photoresist pattern.

* * * * *